US009420770B2

(12) United States Patent
Tector, III et al.

(10) Patent No.: US 9,420,770 B2
(45) Date of Patent: Aug. 23, 2016

(54) METHODS OF MODULATING THROMBOCYTOPENIA AND MODIFIED TRANSGENIC PIGS

(71) Applicant: Indiana University Research and Technology Corporation, Indianapolis, IN (US)

(72) Inventors: Alfred Joseph Tector, III, Carmel, IN (US); Christopher Burlak, Westfield, IN (US)

(73) Assignee: INDIANA UNIVERSITY RESEARCH & TECHNOLOGY CORPORATION, Indianapolis, IN (US)

( * ) Notice: Subject to any disclaimer, the term of this patent is extended or adjusted under 35 U.S.C. 154(b) by 0 days.

(21) Appl. No.: 14/491,183

(22) Filed: Sep. 19, 2014

(65) Prior Publication Data

US 2015/0135344 A1    May 14, 2015

Related U.S. Application Data

(63) Continuation-in-part of application No. 13/512,938, filed as application No. PCT/US2010/058406 on Nov. 30, 2010, now abandoned.

(60) Provisional application No. 61/879,735, filed on Sep. 19, 2013, provisional application No. 61/265,611, filed on Dec. 1, 2009.

(51) Int. Cl.
| | | |
|---|---|---|
| G01N 33/00 | (2006.01) |
| A01K 67/00 | (2006.01) |
| A01K 67/033 | (2006.01) |
| A01K 67/027 | (2006.01) |
| A61K 35/407 | (2015.01) |

(52) U.S. Cl.
CPC ........... *A01K 67/0276* (2013.01); *A61K 35/407* (2013.01); *A01K 2227/108* (2013.01); *A01K 2267/025* (2013.01)

(58) Field of Classification Search
CPC .................................................. A01K 67/0276
See application file for complete search history.

(56) References Cited

U.S. PATENT DOCUMENTS

| | | | |
|---|---|---|---|
| 4,965,392 A | 10/1990 | Fritzberg |
| 4,981,783 A | 1/1991 | Augenlicht |
| 5,350,840 A | 9/1994 | Call |
| 5,352,240 A | 10/1994 | Ross |
| 5,560,911 A | 10/1996 | Koren |
| 5,562,904 A | 10/1996 | Rother |
| 5,569,584 A | 10/1996 | Augenlicht |
| 5,576,201 A | 11/1996 | Mason |
| 5,580,766 A | 12/1996 | Mason |
| 5,610,043 A | 3/1997 | Webber |
| 5,624,837 A | 4/1997 | Fodor |
| 5,627,264 A | 5/1997 | Fodor |
| 5,643,770 A | 7/1997 | Mason |
| 5,651,968 A | 7/1997 | Good |
| 5,688,824 A | 11/1997 | Williams |
| 5,695,759 A | 12/1997 | Good |
| 5,705,732 A | 1/1998 | Sims |
| 5,728,812 A | 3/1998 | Koren |
| 5,736,136 A | 4/1998 | Glotz |
| 5,767,093 A | 6/1998 | Good |
| 5,807,743 A | 9/1998 | Stinchcomb |
| 5,821,117 A | 10/1998 | Sandrin |
| 5,846,715 A | 12/1998 | Purcell |
| 5,847,082 A | 12/1998 | Rother |
| 5,849,991 A | 12/1998 | d'Apice |
| 5,853,722 A | 12/1998 | Rollins |
| 5,858,963 A | 1/1999 | Hawley |
| 5,863,528 A | 1/1999 | Hawley |
| 5,871,997 A | 2/1999 | Rother |
| 5,891,645 A | 4/1999 | Rollins |
| 5,922,854 A | 7/1999 | Kumar |
| 5,980,896 A | 11/1999 | Hellstrom |
| 6,013,857 A | 1/2000 | Deboer |
| 6,040,428 A | 3/2000 | Rollins |
| 6,060,317 A | 5/2000 | Malech |
| 6,096,725 A | 8/2000 | Simon |
| 6,130,062 A | 10/2000 | Milland |
| 6,147,276 A | 11/2000 | Campbell |
| 6,166,288 A | 12/2000 | Diamond |
| 6,190,861 B1 | 2/2001 | Fishman |
| 6,245,890 B1 | 6/2001 | Zhu |
| 6,258,998 B1 | 7/2001 | Damiani |
| 6,271,436 B1 | 8/2001 | Piedrahita |
| 6,331,658 B1 | 12/2001 | Cooper |
| 6,369,294 B1 | 4/2002 | Piedrahita |
| 6,399,578 B1 | 6/2002 | Jack |

(Continued)

FOREIGN PATENT DOCUMENTS

| | | |
|---|---|---|
| AU | 711144 B2 | 10/1998 |
| EP | 0210970 A2 | 2/1987 |

(Continued)

OTHER PUBLICATIONS

Qi Hypertension, 2005, 45:1004-1011.*
Gama Sosa, Brain Struct Function, 2010, 214:91-109.*
Harris et al, 2012, Molecular Biology International, pp. 1-10.*
Paris, L.L., et al. "Reduced human platelet uptake by pig livers deficient in the asialoglycoprotein receptor 1 protein" Kenotransplantation 2015: 22: 203-210.
Arcidiacono, et al., Regulation of Xenogeneic Porcine Pancreatic Islets, Xenotransplantation, 2010, 17:329-337.
Baertschiger, et al., Xenotransplantation Literature Update Nov.-Dec., 2007, Xenotransplantation, 2008, 15:145-149.
Bioxys and Gentaur BVBA, Product Information, Copyright 2005 Gentaur BVBA, Last Modified Feb. 2007, 2 pages.
Boneva, et al., Xenotransplantation and Risks of Zoonotic Infections, Annals of Medicine, 2004, 36:504-517.
Bottino, et al., Islet Xenotransplantation: The Pig-to-Non-Human Primate Model, Xenotransplantation, 2008, 15:104-106.
Braet, et al., Structural and Functional Aspects of Liver Sinusoidal Endothelial Cell Fenestrae: A Review, Comparative Hepatology, 2002, 1:1, 17 pages.

(Continued)

*Primary Examiner* — Valarie Bertoglio
(74) *Attorney, Agent, or Firm* — Quarles & Brady LLP

(57) ABSTRACT

The application provides methods of modulating platelet uptake by liver sinusoidal endothelial cells and of modulating thrombocytopenia. Transgenic pigs modified to bind fewer platelets are provided.

6 Claims, 37 Drawing Sheets

(56) References Cited

U.S. PATENT DOCUMENTS

| | | |
|---|---|---|
| 6,399,758 B1 | 6/2002 | Sandrin |
| 6,423,316 B1 | 7/2002 | Riesbeck |
| 6,455,037 B1 | 9/2002 | Ioannou |
| 6,476,290 B1 | 11/2002 | Wright, Jr. |
| 6,479,626 B1 | 11/2002 | Kim |
| 6,482,404 B1 | 11/2002 | White |
| 6,489,455 B2 | 12/2002 | Chenchik |
| 6,489,458 B2 | 12/2002 | Hackett |
| 6,495,735 B1 | 12/2002 | White |
| 6,498,285 B1 | 12/2002 | Ebert |
| 6,534,261 B1 | 3/2003 | Cox, III |
| 6,548,741 B2 | 4/2003 | DeSousa |
| 6,551,784 B2 | 4/2003 | Fodor |
| 6,558,663 B1 | 5/2003 | Seebach |
| 6,566,102 B1 | 5/2003 | Switzer |
| 6,596,478 B1 | 7/2003 | Heneine |
| 6,607,723 B1 | 8/2003 | Good |
| 6,607,879 B1 | 8/2003 | Cocks |
| 6,607,882 B1 | 8/2003 | Cox, III |
| 6,610,501 B2 | 8/2003 | Zhu |
| 6,613,330 B1 | 9/2003 | Galili |
| 6,613,752 B2 | 9/2003 | Kay |
| 6,639,122 B1 | 10/2003 | Tu |
| 6,660,265 B1 | 12/2003 | Chen |
| 6,686,199 B2 | 2/2004 | DiTullio |
| 6,699,663 B1 | 3/2004 | Fishman |
| 6,703,209 B1 | 3/2004 | Baetscher |
| 6,743,631 B1 | 6/2004 | Mason |
| 6,746,838 B1 | 6/2004 | Choo |
| 6,794,136 B1 | 9/2004 | Eisenberg |
| 6,797,000 B2 | 9/2004 | Simpson |
| 6,824,978 B1 | 11/2004 | Cox, III |
| 6,825,395 B1 | 11/2004 | Murakami |
| 6,841,540 B1 | 1/2005 | Curiel |
| 6,849,448 B1 | 2/2005 | D'Apice |
| 6,866,997 B1 | 3/2005 | Choo |
| 6,872,541 B2 | 3/2005 | Mills |
| 6,903,185 B2 | 6/2005 | Kim |
| 6,933,113 B2 | 8/2005 | Case |
| 6,979,539 B2 | 12/2005 | Cox, III |
| 7,001,998 B2 | 2/2006 | McKenzie |
| 7,008,773 B1 | 3/2006 | Freyberg |
| 7,013,219 B2 | 3/2006 | Case |
| 7,030,215 B2 | 4/2006 | Liu |
| 7,037,790 B2 | 5/2006 | Chang |
| 7,038,107 B2 | 5/2006 | Cui |
| 7,054,342 B2 | 5/2006 | Minneman |
| 7,060,483 B1 | 6/2006 | Muramatsu |
| 7,060,783 B2 | 6/2006 | Seki |
| 7,078,230 B2 | 7/2006 | Wilkison |
| 7,078,232 B2 | 7/2006 | Konkle |
| 7,115,795 B1 | 10/2006 | Forsberg |
| 7,126,039 B2 | 10/2006 | Denning |
| 7,160,682 B2 | 1/2007 | Hackett |
| 7,166,278 B2 | 1/2007 | Zhu |
| 7,201,899 B2 | 4/2007 | d'Apice |
| 7,220,719 B2 | 5/2007 | Case |
| 7,241,573 B2 | 7/2007 | Choo |
| 7,241,574 B2 | 7/2007 | Choo |
| 7,253,334 B2 | 8/2007 | Collas |
| 7,282,556 B2 | 10/2007 | Parkos |
| 7,298,254 B2 | 11/2007 | Tracy |
| 7,321,075 B2 | 1/2008 | Campbell |
| 7,323,323 B2 | 1/2008 | Elliott |
| 7,329,796 B2 | 2/2008 | Campbell |
| 7,368,284 B2 | 5/2008 | Koike |
| 7,378,569 B2 | 5/2008 | Tu |
| 7,384,630 B2 | 6/2008 | Hammerman |
| 7,432,344 B1 | 10/2008 | Lechler |
| 7,438,905 B2 | 10/2008 | Isobe |
| 7,485,769 B2 | 2/2009 | Murakami |
| 7,511,126 B2 | 3/2009 | Rival |
| 7,514,229 B2 | 4/2009 | Jamieson |
| 7,531,715 B1 | 5/2009 | Campbell |
| 7,547,522 B2 | 6/2009 | Hawley |
| 7,547,816 B2 | 6/2009 | Day |
| 7,560,538 B2 | 7/2009 | Koike |
| 7,582,741 B2 | 9/2009 | Jones |
| 7,585,849 B2 | 9/2009 | Liu |
| 7,595,376 B2 | 9/2009 | Kim |
| 7,732,180 B2 | 6/2010 | Koike |
| 7,780,993 B2 | 8/2010 | Reisner |
| 7,795,493 B2 | 9/2010 | Phelps |
| 8,034,330 B2 | 10/2011 | Zhu |
| 8,097,598 B2 | 1/2012 | Lechler |
| 8,106,251 B2 | 1/2012 | Ayares |
| 8,173,861 B2 | 5/2012 | Madsen |
| 8,232,448 B2 | 7/2012 | Varki |
| 8,252,283 B2 | 8/2012 | Freyberg |
| 2001/0041331 A1 | 11/2001 | Leary et al. |
| 2001/0046965 A1 | 11/2001 | Ayares et al. |
| 2002/0012660 A1 | 1/2002 | Colman et al. |
| 2002/0045247 A1 | 4/2002 | Rother et al. |
| 2002/0116053 A1 | 8/2002 | Simpson et al. |
| 2002/0168352 A1 | 11/2002 | Winkler et al. |
| 2002/0168371 A1 | 11/2002 | Awwad |
| 2002/0182678 A1 | 12/2002 | Garrido Pavon et al. |
| 2003/0024002 A1 | 1/2003 | Colman et al. |
| 2003/0032003 A1 | 2/2003 | Schiestl et al. |
| 2003/0086940 A1 | 5/2003 | Costa et al. |
| 2003/0131365 A1 | 7/2003 | Cooper et al. |
| 2003/0153044 A1 | 8/2003 | Liljedahl et al. |
| 2003/0154500 A1 | 8/2003 | Hackett et al. |
| 2003/0157705 A1 | 8/2003 | Fodor et al. |
| 2003/0162163 A1 | 8/2003 | Burgess et al. |
| 2003/0165480 A1 | 9/2003 | Zhu |
| 2003/0192066 A1 | 10/2003 | Zhang et al. |
| 2003/0232410 A1 | 12/2003 | Liljedahl et al. |
| 2004/0033216 A1 | 2/2004 | Elliott et al. |
| 2004/0141944 A1 | 7/2004 | Schwarz et al. |
| 2004/0142449 A1 | 7/2004 | Tonjes et al. |
| 2004/0180041 A1 | 9/2004 | Stice et al. |
| 2004/0208846 A1 | 10/2004 | Zhang et al. |
| 2004/0253229 A1 | 12/2004 | Suzuki et al. |
| 2004/0268424 A1 | 12/2004 | Phelps |
| 2005/0042746 A1 | 2/2005 | Garkavenko |
| 2005/0120400 A1 | 6/2005 | Day et al. |
| 2005/0216964 A1 | 9/2005 | Patience |
| 2005/0260176 A1 | 11/2005 | Ayares et al. |
| 2005/0266561 A1 | 12/2005 | Wells |
| 2006/0015955 A1 | 1/2006 | Clark et al. |
| 2006/0024439 A2 | 2/2006 | Tuominen et al. |
| 2006/0053500 A1 | 3/2006 | Koike |
| 2006/0057719 A1 | 3/2006 | Denning et al. |
| 2006/0068550 A1 | 3/2006 | Chang et al. |
| 2006/0078550 A1 | 4/2006 | Levy et al. |
| 2006/0107337 A1 | 5/2006 | Cui et al. |
| 2006/0130157 A1 | 6/2006 | Wells et al. |
| 2006/0147432 A1 | 7/2006 | Moore et al. |
| 2006/0150261 A1 | 7/2006 | Drabek et al. |
| 2006/0220832 A1 | 10/2006 | Tracy et al. |
| 2006/0294610 A1 | 12/2006 | Koike |
| 2008/0026457 A1 | 1/2008 | Wells et al. |
| 2008/0127360 A1 | 5/2008 | Takahagi et al. |
| 2008/0250517 A1 | 10/2008 | Colman et al. |
| 2009/0004112 A1 | 1/2009 | Abeliovich |
| 2009/0028850 A1 | 1/2009 | Rother et al. |
| 2009/0049562 A1 | 2/2009 | Koike |
| 2009/0049563 A1 | 2/2009 | Harris et al. |
| 2009/0162381 A1 | 6/2009 | Freyberg et al. |
| 2009/0186097 A1 | 7/2009 | Ayares |
| 2009/0203140 A1 | 8/2009 | Amacher et al. |
| 2010/0068202 A1 | 3/2010 | Bell et al. |
| 2010/0077494 A1 | 3/2010 | Wells et al. |
| 2010/0105140 A1 | 4/2010 | Fahrenkrug et al. |

(56) References Cited

U.S. PATENT DOCUMENTS

| | | | |
|---|---|---|---|
| 2010/0146655 | A1 | 6/2010 | Fahrenkrug et al. |
| 2011/0038841 | A1 | 2/2011 | Ayares |
| 2011/0197290 | A1 | 8/2011 | Fahrenkrug et al. |
| 2011/0301341 | A1 | 12/2011 | Zhu |
| 2013/0024961 | A1 | 1/2013 | Burlak et al. |

FOREIGN PATENT DOCUMENTS

| | | |
|---|---|---|
| EP | 0661980 A1 | 7/1995 |
| EP | 0689597 A1 | 1/1996 |
| EP | 0755451 A1 | 1/1997 |
| EP | 0871881 A1 | 10/1998 |
| EP | 0877549 A1 | 11/1998 |
| EP | 0923606 A1 | 6/1999 |
| EP | 1185283 A1 | 3/2002 |
| EP | 1582591 A2 | 10/2005 |
| EP | 1621627 A2 | 2/2006 |
| WO | 9402602 A1 | 2/1994 |
| WO | 9510303 A1 | 4/1995 |
| WO | 9534202 A1 | 12/1995 |
| WO | 9535120 A1 | 12/1995 |
| WO | 9601120 A1 | 1/1996 |
| WO | 9603520 A1 | 2/1996 |
| WO | 9618736 A2 | 6/1996 |
| WO | 9636358 A1 | 11/1996 |
| WO | 9707669 A1 | 3/1997 |
| WO | 9711971 A1 | 4/1997 |
| WO | 9716064 A1 | 5/1997 |
| WO | 9723637 A1 | 7/1997 |
| WO | 9957266 A2 | 11/1999 |
| WO | 9961584 A1 | 12/1999 |
| WO | 0004191 A1 | 1/2000 |
| WO | 0049136 A1 | 8/2000 |
| WO | 0054786 A1 | 9/2000 |
| WO | 0071726 A1 | 11/2000 |
| WO | 0130369 A1 | 5/2001 |
| WO | 0142500 A2 | 6/2001 |
| WO | 0188096 A2 | 11/2001 |
| WO | 0236136 A2 | 5/2002 |
| WO | 2004016742 A2 | 2/2004 |
| WO | 2004022594 A2 | 3/2004 |
| WO | 2004034778 A2 | 4/2004 |
| WO | 2005081714 A2 | 9/2005 |
| WO | 2006001967 A2 | 1/2006 |
| WO | 2006016912 A2 | 2/2006 |
| WO | 2006038211 A2 | 4/2006 |
| WO | 2007002372 A2 | 1/2007 |
| WO | 2007035213 A2 | 3/2007 |
| WO | 2009049234 A2 | 4/2009 |
| WO | 2010008562 A2 | 1/2010 |
| WO | 2010008564 A2 | 1/2010 |
| WO | 2011017315 A2 | 2/2011 |
| WO | 2011068798 A1 | 6/2011 |

OTHER PUBLICATIONS

Burlak, et al., Maturation of Human Neutrophil Phagosomes Includes Incorporation of Molecular Chaperones and Endoplasmic Reticulum Quality Control Machinery, Molecular & Cellular Proteomics, 2006, 5(4):620-634.

Burlak, et al., The Fate of Human Platelets Perfused Through the Pig Liver: Implications for Xenotransplantation, Xenotransplantation, 2010, 17:350-361.

Chandrasekharan, et al., Proprietary Science, Open Science and the Role of Patent Disclosure: The Case of Zinc-Finger Proteins, Nature Biotechnology, 27(2):140-144.

Chari, et al., Brief Report: Treatment of Hepatic Failure with Ex Vivo Pig-Liver Perfusion Followed by Liver Transplantation, The New England Journal of Medicine, 1994, 331(4):234-237.

Craig, et al., TANDEM: Matching Proteins With Tandem Mass Spectra, Bioinformatics, 2004, 20(9):1466-1467.

D'Apice, et al., Gene-Modified Pigs, Xenotransplantation, 2008, 15:87-90.

Deschamps, et al., History of Xenotransplantation, Xenotransplantation, 2005, 12:91-109.

Diaz, et al., Transplantation-Mediated Alloimmune Thrombocytopenia: Guidelines for Utilization of Thrombocytopenic Donors, Liver Transplantation, 2008, 14:1803-1809.

Ekser, et al., Pig Liver Xenotransplantation as a Bridge to Allotransplantation: Which Patients Might Benefit?, Transplantation, 2009, 88(9):1041-1049.

El-Khatib, et al., Aldehyde-Treated Porcine Skin Versus Biobrane as Biosynthetic Skin Substitutes for Excised Burn Hounds: Case Series and Review of the Literature, Annals of Burns and Fire Disasters, 2007, 20(2), 8 pages.

Ellies, et al., Sialyltransferase ST3Gal-IV Operates as a Dominant Modifier of Hemostasis by Concealing Asialoglycoprotein Receptor Ligands, PNAS, 2002, 99(15):10042-10047.

Eng, et al., An Approach to Correlate Tandem Mass Spectral Data of Peptides With Amino Acid Sequences in a Protein Database, J. Am. Soc. Mass Spectrom., 1994, 5:976-989.

Estrada, et al., Swine Generated by Somatic Cell Nuclear Transfer Have Increased Incidence of Intrauterine Growth Restriction (IUGR), Cloning and Stem Cells, 2007, 9(2):229-236.

Fishman, et al., Xenotransplantation: Infectious Risk Revisited, American Journal of Transplantation, 2004, 4:1383-1390.

Fredrickson, He's All Heart . . .and a Little Pig Too: A Look at the FDA Draft Xenotransplant Guideline, Food and Drug Law Journal,1997, 52:429-451.

Galli, et al., Human Natural Anti-a-Galactosyl IgG. II. The Specific Recognition of a(1-3)-linked Galactose Residues, J. Exp. Med., 1985, 162:573-582.

Galli, et al., Genetic Engineering Including Superseding Microinjection: New Ways to Make GM Pigs, Xenotransplantation, 2010, 17(6):397-410.

Gama Sosa, et al., Animal Transgenesis: An Overview, Brain Struct. Funct., 2010, 214:91-109.

Grewal, et al., The Ashwell Receptor Mitigates the Lethal Coagulopathy of Sepsis, Nat. Med., 2008, 14(6):648-655.

Harris, et al., ASGR1 and ASGR2, the Genes that Encode the Asialoglycoprotein Receptor (Ashwell Receptor), Are Expressed in Peripheral Blood Monocyctes and Show Interindividual Differences in Transcript Profile, Molecular Biology International, 2012, vol. 2012, Article ID 283974, 10 pages.

Hauschild, et al., Efficient Generation of a Biallelic Knockout in Pigs Using Zinc-Finger Nucleases, PNAS, 2011, 108 (29):12013-12017.

Herrera, et al., Isolation and Characterization of a Stem Cell Population from Adult Human Liver, Stem Cells, 2006, 24:2840-2850.

Hirano, et al., Evaluation of RNA Interference in Developing Porcine Granulosa Cells Using Fluorescence Reporter Genes, Journal of Reproduction and Development, 2004, 50(5):599-603.

Hoffmeister, et al., The Clearance Mechanism of Chilled Blood Platelets, Cell, 2003, 112:87-97.

Jager, et al., Simultaneous Detection of 15 Human Cytokines in a Single Sample of Stimulated Peripheral Blood Mononuclear Cells, Clinical and Diagnostic Laboratory Immunology, 2003, 10(1):133-139.

Jenke, et al., The Nonviral Episomal Replicating Vector pEPI-1 Allows Long-Term Inhibition of bcr-abl Expression by shRNA, Human Gene Therapy, 2005, 16:533-539.

Josefsson, et al., The Macrophage aMB2 Integrin aM Lectin Domain Mediates the Phagocytosis of Chilled Platelets, Journal of Biological Chemistry, 2005, 280(18):18025-18032.

Khandoga, et al., CD4+ T Cells Contribute to Postischemic Liver Injury in Mice by Interacting With Sinusoidal Endothelium and Platelets, Hepatology, 2006, 43:306-315.

Koike, et al., Functionally Important Glycosylransferase Gain and Loss During Catarrhine Primate Emergence, PNAS, 2007, 104(2):559-564.

Kuehnel, et al., Physiological Function of Stentless Aortic Valves is Altered by Trimming and Removal of Aortic Wall Components, Interactive CardioVascular and Thoracic Surgery, 2007, 6:182-187.

Kurihara, et al., SIRP-a-CD47 System Functions as an Intercellular Signal in the Renal Glomerulus, Am. J. Physiol. Renal. Physiol., 2010, 299:F517-F527.

Kurome, et al., Production Efficiency and Telomere Length of the Cloned Pigs Following Serial Somatic Cell Nuclear Transfer,

(56) References Cited

OTHER PUBLICATIONS

Advance Publication by J-Stage, Journal of Reproduction and Development, Published Online: May 19, 2008, 25 pages.
Lanza, et al., Xenotransplantation, Scientific American, 7/97, 5 pages.
Laurencin, et al., Xenotransplantation in Orthopaedic Surgery, Journal of the American Academy of Orthopaedic Surgeons, 2008, 16(1):4-8.
Lee, et al., A Comparative Study on the Efficiency of Two Enucleation Methods in Pig Somatic Cell Nuclear Transfer: Effects of the Squeezing and the Aspiration Methods, Anim. Biotechnol., 2008, 19(2):71-79.
Lesney, Xenotransplantation—A Long Road Still Traveled, Thoracic Surgery News, Sep. 2009, 1 page.
Li, Establishment of Tumor Cell Lines by Transient Expression of Immortalizing Genes, Gene Ther. Mol. Biol., 1999, 4:261-274.
Li, et al., Efficient Generation of Genetically Distinct Pigs in a Single Pregnancy Using Multiplexed Single-Guide RNA and Carbohydrate Selection, Xenotransplantation, 2015, 22:20-31.
Lin, et al., Coagulation Dysregulation as a Barrier to Xenotransplantation in the Primate, Transpl. Immunol., 2009, 21(2):75-80.
Louz, et al., Reappraisal of Biosafety Risks Posed by PERVs in Xenotransplantation, Rev. Med. Virol., 2008, 18:53-65.
Manzini, et al., Genetically Modified Pigs Produced With a Nonviral Episomal Vector, PNAS, 2006, 103 (47)17672-17677.
March, et al., Microenvironmental Regulation of the Sinusoidal Endothelial Cell Phenotype In Vitro, Hepatology, 2009, 50:920-928.
Margawati, Transgenic Animals: Their Benefits to Human Welfare, Actionbioscience, Jan. 2003, 5 pagesL.
Matou-Kovd, et al., Healing Effect of Recombined Human/Pig Skin on Dermal Defects, Ann. Medit. Burns Club, 1994, 7(3):143.
McCurry, et al., Transgenic Expression of Human Complement Regulatory Proteins in Mice Results in Diminished Complement Deposition During Organ Xenoperfusion, Transplantation, 1995, 59(8):1177-1182.
Meier, et al., Crystal Structure of the Carbohydrate Recognition Domain of the H1 Subunit of the Asialoglycoprotein Receptor, J. Mol. Biol., 2000, 300:857-865.
Meng, Swine Hepatitis E Virus: Cross-Species Infection and Risk in Xenotransplantation, Current Topics in Microbiology and Immunology, 2003, 278:185-216.
Nagashima, et al., Transplantation of Porcine Blastomere Nuclei Into Oocytes Collected From Prepubertal Gilts, Journal of Reproduction and Development, 1992, 38(1):73-78.
Nakagami, et al., Adipose Tissue-Derived Stromal Cells as a Novel Option for Regenerative Cell Therapy, Journal of Atherosclerosis and Thrombosis, 2006, 13(2):77-81.
Nedredal, et al., Liver Sinusoidal Endothelial Cells Represents an Important Blood Clearance System in Pigs, comparative Hepatology, 2003, 2:1, 14 pages.
Niemann, Transgenic Pigs Expressing Plant Genes, PNAS, 2004, 101(19):7211-7212.
O'Connell, The Rationale and Practical Issues for the Maintenance of Clean Herds for Clinical Islet Xenotransplantation, Xenotransplantation, 2008, 15:91-92.
Pereboom, et al., Transmission of Idiopathic Thrombocytopenic Purpura During Orthotopic Liver Transplantation, European Society for Organ Transplantation, 2010, 23:236-238.
Pierson, Current Status of Xenotransplantation, JAMA, 2009, 301(9):967-969.
Prather, et al., Nuclear Transplantation in Early Pig Embryos, Biology of Reproduction, 1989, 41:414-418.
Qi, et al., A New Transgenic Rat Model of Hepatic Steatosis and the Metabolic Syndrome, Hypertension, 2005, 45:1004-1011.
Rudenko, et al., The US FDA and Animal Cloning: Risk and Regulatory Approach, Theriogenology, 2007, 57:198-206.
Rumjantseva, et al., Dual Roles for Hepatic Lectin Receptors in the Clearance of Chilled Platelets, Nature Medicine, 2009, 15(11):1273.
Rumjantseva, et al., Novel and Unexpected Clearance Mechanisms for Cold Platelets, Transfusion and Apheresis Science, 2010, 42:63-70.
Schuurman, et al., Regulatory Aspects of Pig-to-Human Islet Transplantation, Xenotransplantation, 2008, 15:116-120.
Slichter, et al., Evidence-Based Platelet Transfusion Guidelines, Hematology, 2007, pp. 172-178.
Smedsrod, et al., Hepatic Sinusoidal Cells in Health and Disease: Update from the 14th International Symposium, Liver International, 2009, pp. 490-501.
Sorensen, et al., Role of Sialic Acid for Platelet Life Span: Exposure of B-Galactose Results in the Rapid Clearance of Platelets from the Circulation by Asialoglycoprotein Receptor-Expressing Liver Macrophages and Hepatocytes, Blood, 2009, 114:1645-1654.
St. Louis, et al., Effects of Warm Ischemia Following Harvesting of Allograft Cardiac Valves, European Journal of Cardiothoracic Surgery, 1991, 5:458-465.
Stone, et al., Porcine Cartilage Transplants in the Cynomolgus Monkey. III. Transplantation of Alpha-Galactosidase-Treated Porcine Cartilage, Transplantation, 1998, 65(12):1577-1583.
Stone, et al., Replacement of Human Anterior Cruciate Ligaments with Pig Ligaments: A Model for Anti-Non-Gal Antibody Response in Long-Term Xenotransplantation, Transplantation, 2007, 83(2)211-219.
Strowig, et al., Transgenic Expression of Human Signal Regulatory Protein Alpha in Rag2_/_yc_/_Mice Improves Engraftment of Human Hematopoietic Cells in Humanized Mice, PNAS, 2011, 108(32):13218-13223.
Sun, et al., Quantitative Imaging of Gene Induction in Living Animals, Gene Therapy, 2001, 8:1572-1579.
Swindle, et al., Swine in Biomedical Research: Management and Models, ILAR News, 1994, 36(1):1-5.
Taylor, et al., Immune Thrombocytopenic Purpura Following Liver Transplantation: A Case Series and Review of the Literature, Liver Transplantation, 2006, 12:781-791.
Terraube, et al., Factor VIII and von Willebrand Factor Interaction: Biological, Clinical and Therapeutic Importance, Haemophilia, 2010, 16:3-13.
Transplantation Society of Australia & New Zealand, Newsletter, Aug. 2009, 18 pages.
Tuschl, et al., Small Interfering RNAs: A Revolutionary Tool for the Analysis of Gene Function and Gene Therapy, Molecular Interventions, 2002, 2:158-167.
Usui, et al., Tissue Factor Expression Demonstrates Severe Sinusoidal Endothelial Cell Damage During Rejection After Living-Donor Liver Transplantation, J. Hepatobiliary Pancreat Surg., Apr. 17, 2009, [Epub ahead of print].
Vargiolu, et al., In Vitro Production of Multigene Transgenic Blastocysts Via Sperm-Mediated Gene Transfer Allows Rapid Screening of Constructs to be Used in Xenotransplantation Experiments, Transplantation Proceedings, 2010, 42:2142-2145.
Vetere, et al., Synthesis and Characterization of a Novel Glycopolymer with Protective Activity Toward Human Anti-a-Gal Antibodies, Glycobiology, 2002, 12(4):283-290.
Vollmar, et al., the Hepatic Microcirculation: Mechanistic Contributions and Therapeutic Targets in Liver Injury and Repair, Physiol. Rev., 2009, 89:1269-1339.
Wilson, Porcine Endogenous Retroviruses and Xenotransplantation, Cellular and Molecular Life Sciences, 2008, 55:3399-3412.
Yamanouchi, et al., Hepatic Irradiation Augments Engraftment of Donor Cells Following Hepatocyte Transplantation, Hepatology, 2009, 49:258-267.
GenBank: AK233544.1, Sus Scrofa mRNA, Clone:LVRM10170B03, Expressed in Liver.

(56) References Cited

OTHER PUBLICATIONS

GenBank Accession No. NW_001886449: Sus Scrofa Chromosome 7 Genomic Contig, Reference Assembly, Complete Sequence.

PCT International Search Report and Written Opinion, PCT/US2010/058406, May 2, 2011.

PCT International Preliminary Report on Patentability, PCT/US2010/058406, Jun. 5, 2012.

European Patent Office, Extended European Search Report, Application No. 10835005.9, Jun. 18, 2013.

European Patent Office, Partial European Search Report, Application No. 13198948.5, Feb. 26, 2014.

European Patent Office, Extended European Search Report, Application No. 13198948.5, Jun. 18, 2014.

* cited by examiner

Panel A

ASGR1 KO

```
WT          TTCGAGGTCTAGCCAGCCTTAGCATGACAAAGGAATATCAGGATCTGCA (SEQ ID NO:14)
Cell for NT TTCG--------------------------------AGGAATATCAGGATCTGCA
Fetus       TTCG--------------------------------AGGAATATCAGGATCTGCA
Piglet 1-5  TTCG--------------------------------AGGAATATCAGGATCTGCA
```

FIG. 19

Panel B

GGTA1-CMAH-iGb3S triple knockout

```
GGTA1-wt  GAGAAAATAATGAATGTCAAAGGAAGA (SEQ ID NO:16)
Fetus 3   GAGAAAATAATGAATGT CAAAGGAAGA   +1bp CMAH-wt   GAGTAAGGTACGTGATCTGTTGG (SEQ ID NO:17)
Fetus 3   GAGTAAGG-----------TTGG    -11bp
          GAGTAAGGTA--------TGTTGG   -7bp iGb3S-wt  GCGCTGGCAGGACGTGTCCATGGCGCGCATGCGCGGCGCTGCACCCGGCGCTCGGGGGGGC
          (SEQ ID NO:18)
Fetus 3   GCGCTGGCAGGA---------------------------------------------CGC
```

FIG. 19 (continued)

```
                         SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Primer Sequence ASGR1 Forward

<400> SEQUENCE: 1
gcgagcacag acgccaaggt                                              20

<210> SEQ ID NO 2
<211> LENGTH: 20
<212> TYPE: DNA
<213> ORGANISM: Artificial Sequence
<220> FEATURE:
<223> OTHER INFORMATION: Primer Sequence ASGR1 reverse

<400> SEQUENCE: 2
gtgggcacag tcctcgccac                                              20

<210> SEQ ID NO 3
<211> LENGTH: 20
<212> TYPE: DNA
<213> ORGANISM: Artificial Sequence
<220> FEATURE:
<223> OTHER INFORMATION: Primer Sequence CD31 forward

<400> SEQUENCE: 3
acctggtcac cgtgagggaa                                              20

<210> SEQ ID NO 4
<211> LENGTH: 20
<212> TYPE: DNA
<213> ORGANISM: Artificial Sequence
<220> FEATURE:
<223> OTHER INFORMATION: Primer Sequence CD31 reverse

<400> SEQUENCE: 4
atttccggga acgactgggc                                              20
```

-continued

```
<210> SEQ ID NO 5
<211> LENGTH: 20
<212> TYPE: DNA
<213> ORGANISM: Artificial Sequence
<220> FEATURE:
<223> OTHER INFORMATION: Primer Sequence CD105 forward

<400> SEQUENCE: 5
accagctctt cctctgggca                                                   20

<210> SEQ ID NO 6
<211> LENGTH: 20
<212> TYPE: DNA
<213> ORGANISM: Artificial Sequence
<220> FEATURE:
<223> OTHER INFORMATION: Primer Sequence CD105 reverse

<400> SEQUENCE: 6
catgtccttg cggggttcca                                                   20

<210> SEQ ID NO 7
<211> LENGTH: 20
<212> TYPE: DNA
<213> ORGANISM: Artificial Sequence
<220> FEATURE:
<223> OTHER INFORMATION: Primer Sequence beta-actin forward

<400> SEQUENCE: 7
tccctggaga agagctacga                                                   20

<210> SEQ ID NO 8
<211> LENGTH: 20
<212> TYPE: DNA
<213> ORGANISM: Artificial Sequence
<220> FEATURE:
<223> OTHER INFORMATION: Primer Sequence beta actin reverse

<400> SEQUENCE: 8
tgttggcgta gaggtccttc                                                   20

<210> SEQ ID NO 9
<211> LENGTH: 1348
<212> TYPE: DNA
<213> ORGANISM: Sus scrofa
<220> FEATURE:
<221> NAME/KEY: CDS
<222> LOCATION: (218)..(1078)
<223> OTHER INFORMATION: porcine ASGR1

<400> SEQUENCE: 9
gggcagacgc acagggctca gggcccgcgt atggaccctg cccctccgc tcccactttc         60 cagggctgtc cgcgcaccct aattctccag ccttcggccg ctctcccagc cgggcatctg       120
cacagcagtg agggacccag gagtccacct tgagaccttc agcaacctca gccttaacct       180
tggcggtgac ctggttcgag gtctagccag ccttagc atg aca aag gaa tat cag        235
                                        Met Thr Lys Glu Tyr Gln
                                          1               5 gat ctg cag cat ctg gac aat gag gag aat gac cag cag cac aga aaa        283
Asp Leu Gln His Leu Asp Asn Glu Glu Asn Asp Gln Gln His Arg Lys
          10                  15                  20 ggg cca cct cct caa ccg tca ctc ctt cgg cgt ctc tgc tcg gga ccc        331
Gly Pro Pro Pro Gln Pro Ser Leu Leu Arg Arg Leu Cys Ser Gly Pro
      25                  30                  35 tgc ctc ctc ctg att tcc atg ggc ctt agc ctc ctg ctg gta gtt        379
Cys Leu Leu Leu Ile Ser Met Gly Leu Ser Leu Leu Leu Val Val
```

```
                40              45              50
gtc tgt gtg atc gga tcc cag aac tcc aag ctg cag gag gag ctg cag      427
Val Cys Val Ile Gly Ser Gln Asn Ser Lys Leu Gln Glu Glu Leu Gln
 55              60              65              70 gcc ctg aga gag acc ttc agc aac ctc acc gcg agc aca gac gcc aag      475
Ala Leu Arg Glu Thr Phe Ser Asn Leu Thr Ala Ser Thr Asp Ala Lys
                 75              80              85 gtc aag acc ctc agc atg cag gga gga aat gtg ggc aga aag atg aag      523
Val Lys Thr Leu Ser Met Gln Gly Gly Asn Val Gly Arg Lys Met Lys
             90              95             100 tcc ctg gag tcc cag ctg gag aaa cag caa cag gac ctg agt gaa gat      571
Ser Leu Glu Ser Gln Leu Glu Lys Gln Gln Gln Asp Leu Ser Glu Asp
         105             110             115 cac tcc agc ttg ctg ctc cac gtg aag cag ttt gtg tcc gac ctg cgg      619
His Ser Ser Leu Leu Leu His Val Lys Gln Phe Val Ser Asp Leu Arg
     120             125             130 agc ctc agc tgt cag atg gct gtc ctc cag ggc aat ggc tct gaa agg      667
Ser Leu Ser Cys Gln Met Ala Val Leu Gln Gly Asn Gly Ser Glu Arg
135             140             145             150 acc tgc tgc ccg gtt aac tgg gtg ggc tat gaa ggc agc tgc tac tgg      715
Thr Cys Cys Pro Val Asn Trp Val Gly Tyr Glu Gly Ser Cys Tyr Trp
                155             160             165 ttt tcc cgc tct ggg aag ccc tgg ccg gag gcc gag aag tac tgc cag      763
Phe Ser Arg Ser Gly Lys Pro Trp Pro Glu Ala Glu Lys Tyr Cys Gln
            170             175             180 ctg gag aat gcc cac ctc gtg gtg gtg ggc tcc tgg gag gag cag aaa      811
Leu Glu Asn Ala His Leu Val Val Val Gly Ser Trp Glu Glu Gln Lys
        185             190             195 ttt atc cag cac cac gtg ggc cct gtg aac tcc tgg atc ggc ctc act      859
Phe Ile Gln His His Val Gly Pro Val Asn Ser Trp Ile Gly Leu Thr
    200             205             210 gat cag agc ggg ccc tgg aag tgg gtg gat ggc acc gac tac gag tcg      907
Asp Gln Ser Gly Pro Trp Lys Trp Val Asp Gly Thr Asp Tyr Glu Ser
215             220             225             230 ggc ttc aag aac tgg aga ccc gag cag ccg gat gac tgg tac ggg cat      955
Gly Phe Lys Asn Trp Arg Pro Glu Gln Pro Asp Asp Trp Tyr Gly His
                235             240             245 ggg ctc ggg ggt ggc gag gac tgt gcc cac ttt acg gag gac ggc ggc     1003
Gly Leu Gly Gly Gly Glu Asp Cys Ala His Phe Thr Glu Asp Gly Gly
            250             255             260 tgg aac gat gac atc tgc cag agg ccc tac cgc tgg gtc tgc gag aca     1051
Trp Asn Asp Asp Ile Cys Gln Arg Pro Tyr Arg Trp Val Cys Glu Thr
        265             270             275 cag cgg gac agg gac agc ggc agc tag gagtctcctc tccctctaat           1098
Gln Arg Asp Arg Asp Ser Gly Ser
    280             285 ttatgtcctc aatgctttta cctgccacgg gggtcttggt tggggaccc tcccctctgg    1158 gtgcttccgg attttcacct cggatttga gggaagggag aagggtgggg tctgaggaat    1218
ggagagtgat gtttggaggg gtggggagtt tgaaacgcct gccagtttct gtagtttgca   1278
gggtattatt gtcaactttt tttttttaag agtaaaaaga agtgaaatat acaaaaaaaa   1338
aaaaaaaaaa                                                          1348

<210> SEQ ID NO 10
<211> LENGTH: 286
<212> TYPE: PRT
<213> ORGANISM: Sus scrofa

<400> SEQUENCE: 10
```

```
Met Thr Lys Glu Tyr Gln Asp Leu Gln His Leu Asp Asn Glu Glu Asn
1               5                   10                  15

Asp Gln Gln His Arg Lys Gly Pro Pro Gln Pro Ser Leu Leu Arg
            20                  25                  30

Arg Leu Cys Ser Gly Pro Cys Leu Leu Leu Ile Ser Met Gly Leu Ser
            35                  40                  45

Leu Leu Leu Leu Val Val Val Cys Val Ile Gly Ser Gln Asn Ser Lys
50                  55                  60

Leu Gln Glu Glu Leu Gln Ala Leu Arg Glu Thr Phe Ser Asn Leu Thr
65                  70                  75                  80

Ala Ser Thr Asp Ala Lys Val Lys Thr Leu Ser Met Gln Gly Gly Asn
            85                  90                  95

Val Gly Arg Lys Met Lys Ser Leu Glu Ser Gln Leu Glu Lys Gln Gln
            100                 105                 110

Gln Asp Leu Ser Glu Asp His Ser Ser Leu Leu Leu His Val Lys Gln
            115                 120                 125

Phe Val Ser Asp Leu Arg Ser Leu Ser Cys Gln Met Ala Val Leu Gln
            130                 135                 140

Gly Asn Gly Ser Glu Arg Thr Cys Cys Pro Val Asn Trp Val Gly Tyr
145                 150                 155                 160

Glu Gly Ser Cys Tyr Trp Phe Ser Arg Ser Gly Lys Pro Trp Pro Glu
                165                 170                 175

Ala Glu Lys Tyr Cys Gln Leu Glu Asn Ala His Leu Val Val Val Gly
                180                 185                 190

Ser Trp Glu Glu Gln Lys Phe Ile Gln His His Val Gly Pro Val Asn
            195                 200                 205

Ser Trp Ile Gly Leu Thr Asp Gln Ser Gly Pro Trp Lys Trp Val Asp
            210                 215                 220

Gly Thr Asp Tyr Glu Ser Gly Phe Lys Asn Trp Arg Pro Glu Gln Pro
225                 230                 235                 240

Asp Asp Trp Tyr Gly His Gly Leu Gly Gly Gly Glu Asp Cys Ala His
                245                 250                 255

Phe Thr Glu Asp Gly Gly Trp Asn Asp Asp Ile Cys Gln Arg Pro Tyr
                260                 265                 270

Arg Trp Val Cys Glu Thr Gln Arg Asp Arg Asp Ser Gly Ser
            275                 280                 285

<210> SEQ ID NO 11
<211> LENGTH: 21
<212> TYPE: DNA
<213> ORGANISM: Artificial Sequence
<220> FEATURE:
<223> OTHER INFORMATION: siRNA sense sequence

<400> SEQUENCE: 11
cagcaugcag ggaggaaauu u                                           21

<210> SEQ ID NO 12
<211> LENGTH: 21
<212> TYPE: DNA
<213> ORGANISM: Artificial Sequence
<220> FEATURE:
<223> OTHER INFORMATION: siRNA ASGR1 antisense sequence

<400> SEQUENCE: 12
auuuccuccc ugcaugcugu u                                           21
```

<210> SEQ ID NO 13
<211> LENGTH: 33
<212> TYPE: PRT
<213> ORGANISM: Homo sapiens

<400> SEQUENCE: 13

Arg Pro Glu Gln Pro Asp Asp Trp Tyr Gly His Gly Leu Gly Gly Gly
1               5                   10                  15

Glu Asp Cys Ala His Phe Thr Asp Asp Gly Arg Trp Asn Asp Val
            20                  25                  30

Cys

<210> SEQ ID NO 14
<211> LENGTH: 49
<212> TYPE: DNA
<213> ORGANISM: Sus scrofa
<220> FEATURE:
<221> NAME/KEY: misc_feature
<222> LOCATION: (0)..(0)
<223> OTHER INFORMATION: Portion of ASGR1 wildtype sequenc
<220> FEATURE:
<221> NAME/KEY: misc_feature
<222> LOCATION: (0)..(0)
<223> OTHER INFORMATION: Portion of ASGR1 wildtype sequenc

<400> SEQUENCE: 14
ttcgaggtct agccagcctt agcatgacaa aggaatatca ggatctgca         49

<210> SEQ ID NO 15
<211> LENGTH: 26
<212> TYPE: DNA
<213> ORGANISM: Sus scrofa
<220> FEATURE:
<221> NAME/KEY: misc_feature
<222> LOCATION: (0)..(0)
<223> OTHER INFORMATION: deleted region of ASGR1
<220> FEATURE:
<221> NAME/KEY: misc_feature
<222> LOCATION: (0)..(0)
<223> OTHER INFORMATION: deleted region of ASGR1

<400> SEQUENCE: 15
aggtctagcc agccttagca tgacaa                                  26

<210> SEQ ID NO 16
<211> LENGTH: 27
<212> TYPE: DNA
<213> ORGANISM: Sus scrofa
<220> FEATURE:
<221> NAME/KEY: misc_feature
<222> LOCATION: (0)..(0)
<223> OTHER INFORMATION: portion of alpha-Gal sequence

<400> SEQUENCE: 16
gagaaaataa tgaatgtcaa aggaaga                                 27

<210> SEQ ID NO 17
<211> LENGTH: 23
<212> TYPE: DNA
<213> ORGANISM: Sus scrofa
<220> FEATURE:
<221> NAME/KEY: misc_feature
<222> LOCATION: (0)..(0)
<223> OTHER INFORMATION: portion of CMAH sequence

<400> SEQUENCE: 17
gagtaaggta cgtgatctgt tgg                                     23

```
<210> SEQ ID NO 18
<211> LENGTH: 60
<212> TYPE: DNA
<213> ORGANISM: Sus scrofa
<220> FEATURE:
<221> NAME/KEY: misc_feature
<222> LOCATION: (0)..(0)
<223> OTHER INFORMATION: Portion of iGB3S sequence

<400> SEQUENCE: 18
gcgctggcag gacgtgtcca tggcgcgcat gcgcgcgctg cacccggcgc tcggggggcg    60

<210> SEQ ID NO 19
<211> LENGTH: 19
<212> TYPE: DNA
<213> ORGANISM: Artificial Sequence
<220> FEATURE:
<223> OTHER INFORMATION: iG3BS primer

<400> SEQUENCE: 19
tggcacactt cctggagac                                                 19

<210> SEQ ID NO 20
<211> LENGTH: 20
<212> TYPE: DNA
<213> ORGANISM: Artificial Sequence
<220> FEATURE:
<223> OTHER INFORMATION: iG3BS primer

<400> SEQUENCE: 20
cgcatggtag tagaggtcgc                                                20
```

METHODS OF MODULATING THROMBOCYTOPENIA AND MODIFIED TRANSGENIC PIGS

CROSS-REFERENCE TO RELATED APPLICATIONS

This application is continuation-in-part of co-pending Ser. No. 13/512,938 filed on Oct. 10, 2012 which was a National Stage Application of PCT/US2010/058406 filed on Nov. 30, 2010 which claimed priority to, and the benefit of U.S. Provisional Patent Application No. 61/265,611, entitled "METHODS OF MODULATING THROMBOCYTOPENIA AND MODIFIED TRANSGENIC PIGS", filed on Dec. 1, 2009; and claims benefit of U.S. Provisional Patent Application 61/879,735, entitled "Transgenic Pigs Suitable for Xenograft" filed on Sep. 19, 2013 all of which are incorporated herein by reference in their entirety.

STATEMENT REGARDING FEDERALLY SPONSORED RESEARCH OR DEVELOPMENT

Not applicable.

FIELD OF THE INVENTION

The invention relates to the field of modulating thrombocytopenia, developing compounds for modulating thrombocytopenia, and developing transgenic pigs with reduced propensity to cause thrombocytopenia in xenotransplant.

BACKGROUND OF THE INVENTION

It is well known that transplants from one animal into another animal of the same species, such as human to human, are a routine treatment option for many serious conditions including kidney, heart, lung, liver and other organ disease and skin damage such as severe burn disease. However, it is well known that there are not enough suitable organs available for transplant to meet current or expected clinical demands for organ transplants. More than 18,000 human patients are on the UNOS liver transplant national waiting list, yet less than 7,000 transplants are performed annually in the United States. In patients with kidney failure, dialysis increases the length of time the patient can wait for a transplant. There is no system comparable to dialysis available for patients with liver disease or liver failure.

Xenotransplantation, the transplant of organs, tissues or cells from one animal into another animal of a different species, such as the transplantation of a pig organ into a human recipient has the potential to reduce the shortage of organs available for transplant, potentially helping thousands of people worldwide. However, xenotransplantation using standard, unmodified pig tissue into a human or other primate is accompanied by severe rejection of the transplanted tissue. The rejection may be a hyperacute rejection, an acute rejection, a chronic rejection or may involve survival limiting thrombocytopenia coagulopathy. The human hyperacute rejection response to pig antibodies present on transplanted tissue is so strong that the transplant tissue is typically damaged by the human immune system within minutes or hours of transplant into the human. Attempts have been made to transplant human patients with livers from other organisms such as pigs; however, immediately upon reperfusion of the liver xenotransplant, the patient begins to undergo survival limiting thrombocytopenia coagulopathy. The mechanism by which the thrombocytopenia occurs is unknown; although in 1983 it was reported that hepatocytes bind the platelets causing the thrombocytopenia. Thrombocytopenia or thrombopenia is an abnormal decrease in the platelet number of a patient that also occurs in multiple hemorrhagic conditions.

Many strategies have been employed to address the rejection response including removing porcine genes encoding $\alpha(1,3)$ galactosyltransferase and CMAH to prevent expression of the enzymes. However, progress in this field is critically dependent upon the development of genetically modified pigs. Unfortunately, developing homozygous knockout pigs is a slow process, requiring as long as three years using traditional methods of homologous recombination in fetal fibroblasts followed by somatic cell nuclear transfer (SCNT), and then breeding of heterozygous knockout animals to yield a homozygous knockout pig. The development of new knockout pigs for xenotransplantation has been hampered by the lack of pluripotent stem cells, relying instead on the fetal fibroblast as the cell upon which genetic engineering was carried out. For instance, the production of the first live pigs lacking any functional expression of $\alpha(1,3)$ galactosyltransferase (GTKO) was first reported in 2003. U.S. Pat. No. 7,795,493 to Phelps et al describes a method for the production of a pig that lacks any expression of functional $\alpha$Gal.

Profound thrombocytopenia has been transmitted to recipients in cases where a donor liver was procured from an individual suffering from idiopathic thrombocytopenic purpura (ITP). The thrombocytopenia in the recipients was refractory to treatment and only alleviated once the ITP donor liver was removed and the patient retransplanted with another liver. Patients with preexisting ITP who received liver transplants for other diseases have experienced alleviation of the ITP (Taylor et al (2006) *Liver Transplant* 12(5):781-791; Diaz et al (2008) *Liver Transplant* 14(12):1803-1809; and Pereboom et al (2009) *Transpl Int*, herein incorporated by reference in their entirety.

Platelets survive in the human/baboon circulation for 7-10 days and are removed by the liver and spleen. Cold stored platelets are rapidly cleared from the circulation, forcing exogenous platelets to be used for transfusion to be stored at room temperature. Storage at room temperature reduces platelet shelf live to 5 days. Cold-stored platelets have been thought to be removed from the circulation by a mechanism involving the Kupffer cells and hepatocytes. Mac-1 receptors on Kupffer cells irreversibly recognize clustered $\beta$-GlcNac-terminating immature glycans on GPIb receptors on short term (<4 hours) cooled (0° C.) platelets. See Hoffmeister et al (2003), *Cell* 112:87-97 and Josefsson et al (2005) *J. Biol. Chem* 280:18025-18032, herein incorporated by reference in their entirety.

SUMMARY OF THE INVENTION

Compositions and methods for modulating platelet uptake and thrombocytopenia are provided. The compositions and methods are based on the discovery that liver sinusoidal endothelial cells and Kupffer cells function in platelet uptake. The methods and compositions allow identification of platelet uptake modulating compounds; liver sinusoidal endothelial cell platelet uptake modulating compounds and platelet binding related proteins.

In an embodiment, methods of identifying a liver sinusoidal endothelial cell (LSEC) platelet uptake modulating compound are provided. The methods comprise the steps of providing liver sinusoidal endothelial cells, incubating a compound of interest with a first aliquot of liver sinusoidal endothelial cells, incubating a labeled platelet with the first aliquot of liver sinusoidal endothelial cells and a second aliquot of untreated liver sinusoidal endothelial cells, monitoring platelet uptake by the first and second aliquots of liver sinusoidal endothelial cells, comparing platelet uptake by liver sinusoidal endothelial cells in the first and second aliquots, and identifying a compound of interest as a liver sinusoidal endothelial cell platelet uptake modulating compound when there is a significant difference in platelet uptake by liver sinusoidal endothelial cells between the first and second aliquots.

In an embodiment, methods of identifying a liver sinusoidal endothelial cell (LSEC) platelet uptake modulating compound are provided. The methods comprise the steps of providing liver sinusoidal endothelial cells, incubating a compound of interest with a first aliquot of liver sinusoidal endothelial cells, incubating a polymer particle coated with human platelet membranes with the first aliquot of liver sinusoidal endothelial cells and a second aliquot of untreated liver sinusoidal endothelial cells, monitoring uptake of a polymer particle coated with human platelet membranes by the first and second aliquots of liver sinusoidal endothelial cells, comparing uptake of the polymer particle by liver sinusoidal endothelial cells in the first and second aliquots, and identifying a compound of interest as a liver sinusoidal endothelial cell platelet uptake modulating compound when there is a significant difference in uptake of the polymer particle by liver sinusoidal endothelial cells in the first and second aliquots.

In an embodiment, methods of modulating platelet uptake by liver sinusoidal endothelial cells are provided. The methods involve the steps of providing a subject at risk for platelet uptake by liver sinusoidal endothelial cells and administering a liver sinusoidal endothelial cell platelet uptake modulating compound. In an aspect, the modulating compound is administered to the subject. In an aspect, the subject is at risk because of exogenous platelet introduction. In an aspect, the liver sinusoidal endothelial cell platelet uptake modulating compound is incubated with the exogenous platelets prior to or concomitant with introduction into the subject. In an aspect, the subject is at risk because of a liver transplant.

In an embodiment methods of identifying a platelet binding related protein are provided. The methods involve the steps of providing an isolated liver sinusoidal endothelial cell, incubating a polymer particle coated with human platelet membranes with the isolated liver sinusoidal endothelial cells, harvesting a phagosome comprising a polymer particle from the liver sinusoidal endothelial cells, isolating the polymer particles from the phagosomes, analyzing a protein complex associated with the polymer particle, evaluating the origin of the proteins in the protein complex and identifying the proteins in a protein complex that comprises a protein of platelet origin and a protein of liver sinusoidal endothelial cell origin as platelet binding related proteins.

In an embodiment methods of identifying a thrombocytopenia modulating compound are provided. The methods comprise the steps of providing liver sinusoidal endothelial cells, incubating a compound of interest with a first aliquot of liver sinusoidal endothelial cells, incubating a labeled platelet with a first aliquot of liver sinusoidal endothelial cells and a second aliquot of liver sinusoidal endothelial cells, monitoring platelet uptake into the liver sinusoidal endothelial cells, comparing platelet uptake by the liver sinusoidal endothelial cells in the first and second aliquots and identifying the compound of interest as a thrombocytopenia modulating compound when there is a significant difference in platelet uptake by the liver sinusoidal endothelial cells in the first and second aliquots.

Methods of modulating the asialoglycoprotein receptor-ligand interaction comprising the step of administering an asialoglycoprotein receptor modulating compound are provided. In an embodiment an asialoglycoprotein receptor modulating compound is selected from the group comprising an isolated double-stranded ribonucleic acid (dsRNA) molecule comprising a first strand of nucleotides that is substantially identical to 19 to 25 nucleotides set forth in SEQ ID NO:9 and an isolated double-stranded ribonucleic acid (dsRNA) molecule comprising a first strand of nucleotides comprising a sequence set forth in SEQ ID NO:11 and a second strand of nucleotides comprising a sequence substantially complementary to the first strand.

Methods of identifying an asialoglycoprotein receptor modulating compound are provided. The methods comprise the steps of providing liver sinusoidal endothelial cells, incubating a compound of interest with a first aliquot of liver sinusoidal endothelial cells, incubating a labeled platelet with said first aliquot of liver sinusoidal endothelial cells and a second aliquot of liver sinusoidal endothelial cells, monitoring platelet uptake into the liver sinusoidal endothelial cells, comparing platelet uptake by the liver sinusoidal endothelial cells in the first and second aliquots and identifying the compound of interest as an asialoglycoprotein receptor modulating compound when there is a significant difference in platelet uptake by the liver sinusoidal endothelial cells of the first and second aliquots.

Methods of modulating liver sinusoidal endothelial cell platelet uptake comprising the steps of providing a subject at risk for liver sinusoidal endothelial cell platelet uptake and administering an asialoglycoprotein receptor modulating compound are provided. In an aspect of the methods, the asialoglycoprotein receptor modulating compound is selected from the group comprising an isolated double-stranded ribonucleic acid (dsRNA) molecule comprising a first strand of nucleotides that is substantially identical to 19 to 25 consecutive nucleotides set forth in SEQ ID NO:9 and an isolated double-stranded ribonucleic acid molecule comprising a first strand of nucleotides comprising a sequence set forth in SEQ ID NO:11 and a second strand of nucleotides comprising a sequence substantially complementary to the first strand.

Methods of modulating thrombocytopenia comprising the steps of providing a subject at risk for thrombocytopenia and administering an asialoglycoprotein modulating compound to the subject are provided.

Methods of modulating liver sinusoidal endothelial cell platelet uptake comprising the steps of providing a transgenic animal with altered expression of the asialoglycoprotein receptor gene are provided. The transgenic animal may be a mammal selected from the group comprising simian, porcine, ovine, canine, equine, bovine, caprine, feline and lapine mammals, particularly a porcine mammal. In an aspect, the transgenic animal exhibits reduced expression of the asialoglycoprotein receptor. In an aspect, the liver sinusoidal endothelial cell platelet uptake by a transgenic liver from the transgenic animal is reduced as compared to liver sinusoidal endothelial cell platelet uptake by a non-transgenic liver. In an aspect, the disrupted ASGR1 encodes a polypeptide having an amino acid sequence wherein the amino acid sequence of said polypeptide is selected from the group comprising an amino acid sequence that differs by at least one amino acid from the amino acid sequence set forth in SEQ ID NO:10, an amino acid sequence having an amino acid sequence other than glycine at position 262 of SEQ ID NO:10, an amino acid sequence having an arginine residue at position 262 of SEQ ID NO:10 and an amino acid sequence that differs by at least 1-20 amino acid residues from the amino acid sequence set forth in SEQ ID NO:10. In an aspect the transgenic animal comprises an expression cassette comprising an isolated nucleic acid molecule that is transcribed into a short hairpin RNA.

A transgenic animal with an altered asialoglycoprotein receptor gene wherein the animal exhibits altered expression of the asialoglycoprotein receptor and altered liver sinusoidal endothelial cell platelet uptake is provided. A transgenic animal with a disrupted asialoglycoprotein receptor (ASGR1) gene in the nuclear genome of at least one cell wherein the animal exhibits expression of an asialoglycoprotein receptor polypeptide with an altered amino acid sequence, particularly a polypeptide with amino acid sequence having an amino acid residue other than glycine at amino acid at position 262, more particularly having an arginine at position 262. In an aspect the transgenic animal is a transgenic pig.

A porcine organ, tissue or cell obtained from the knockout pig is provided. A porcine organ, tissue or cell may be selected from the group consisting of skin, heart, liver, kidneys, lung, pancreas, thyroid, small bowel and components thereof. In an aspect, when tissue from the knockout pig is transplanted into a human, a hyperacute rejection related symptom is improved as compared to when tissue from a wild-type pig is transplanted into a human. In an aspect, when tissue from the knockout pig is transplanted into a human, thrombocytopenia is decreased as compared to when tissue from a wild-type pig is transplanted into a human. In an aspect, when a liver from the knockout pig is exposed to human platelets, the liver exhibits reduced uptake of human platelets as compared to when a liver from a wild-type pig is exposed to human platelets.

In an embodiment, a skin related product obtained from a knockout pig comprising a disrupted ASGR1 gene in the nuclear genome of at least one cell of the pig and wherein expression of ASGR1 is decreased as compared to a wild-type pig is provided. In an aspect of the application the skin related product exhibits reduced premature separation from a wound, particularly from a human skin wound.

Methods of preparing transplant material for xenotransplantation into a human are provided. The methods comprise providing a knockout pig of the application as a source of the transplant material and wherein the transplant material is selected from the group consisting of organs, tissues, and cells and wherein the transplant material has reduced levels of ASGR1 expression.

Methods of increasing the duration of the period between when a human subject is identified as a subject in need of a human liver transplant and when said human liver transplant occurs are provided. The methods involve providing a liver from a knockout pig comprising disrupted ASGR1 gene wherein expression of ASGR1 is decreased as compared to a wild-type pig and surgically attaching a liver from the knockout pig to the human subject in a therapeutically effective manner. In an aspect, the liver is surgically attached internal to the human subject. In an aspect, the liver is surgically attached external to the human subject. The liver may be directly or indirectly attached to the subject.

Methods of reducing premature separation of a skin related product from a human subject are provided. The methods involve the steps of providing a knockout pig comprising disrupted ASGR1 genes and preparing a skin related product from the knockout pig. Expression of ASGR1 in the knockout pig is decreased as compared to a wild-type pig.

Methods of improving a hyperacute rejection related symptom in a patient are provided. The methods involve transplanting porcine transplant material having a reduced level of ASGR1 into a subject. A hyperacute rejection related symptom is improved as compared to when porcine transplant material from a wild-type pig is transplanted into a human.

A knockout pig comprising a disrupted ASGR1 gene in the nuclear genome of at least one cell of the pig is provided. The disruption of the ASGR1 gene is a homozygous deletion of 26 base pairs. A liver from the pig exhibits altered platelet uptake. In an aspect, the homozygous deletion disrupts the ASGR1 gene at a region of the wild-type gene having the nucleotide sequence set forth as AGGTCTAGCCAGCCT-TAGCATGACAA (SEQ ID NO:2). In an aspect, the disrupted ASGR1 gene encodes a polypeptide having an amino acid sequence that differs by at least 1-9 amino acid residues from the wild-type amino acid sequence.

Methods of modulating platelet uptake comprising the step of providing a liver isolated from a knockout pig comprising a disrupted ASGR1 gene and surgically attaching the liver from the knockout pig to a human subject in a therapeutically effective manner are provided by the application. In an aspect platelet uptake by a transgenic liver from the knockout animal is reduced as compared to platelet uptake by a non-transgenic porcine liver.

Methods of modulating thrombocytopenia comprising the steps of providing a subject at risk for thrombocytopenia and administering a Mac-1 inhibitor to the subject are provided.

Methods of modulating liver sinusoidal endothelial cell platelet uptake comprising the steps of providing a transgenic animal comprising a disrupted ASGR1 gene are provided. The transgenic animal comprises a disrupted ASGR1 gene in the nuclear genome of at least one cell of the animal wherein the disrupted ASGR1 gene is homozygous and the animal exhibits altered platelet uptake. In the methods the transgenic animal may be a mammal selected from the group comprising simian, porcine, ovine, caprine, equine, bovine, canine, feline, and lapine mammals, particularly porcine mammals. In an embodiment the animal exhibits reduced expression of ASGR1. In an embodiment platelet uptake by a transgenic liver from a transgenic animal provided herein is reduced as compared to platelet uptake by a non-transgenic liver.

Transgenic pigs comprising a disrupted ASGR1 gene in the nuclear genome of at least one cell of the pig are provided. The disrupted ASGR1 gene is homozygous and the pig exhibits altered platelet uptake.

Transgenic pigs comprising a disrupted ASGR2 gene in the nuclear genome of at least one cell of the pig are provided. The disrupted ASGR2 gene is homozygous and the pig exhibits altered platelet uptake.

Transgenic pigs comprising a disrupted Mac1 gene in the nuclear genome of at least one cell of the pig are provided. The disrupted Mac1 gene is homozygous and the pig exhibits altered platelet uptake.

Isolated double-stranded ribonucleic acid molecules comprising a first strand of nucleotides that is substantially identical to 19-25 consecutive nucleotides set forth in SEQ ID NO:9 and a second strand of nucleotides that is substantially complementary to the first strand or "siRNA" molecules that inhibit expression of a nucleic acid molecule encoding ASGR1 are provided. Isolated double-stranded ribonucleic acid molecules comprising a first strand of nucleotides having a nucleotide sequence set forth in SEQ ID NO:11 are provided and a second strand of nucleotides that is substantially complementary to the first strand. Isolated nucleic acid molecules comprising an expression control sequence operably linked to a nucleotide sequence that is a template for one or both strands of the siRNA molecule that inhibits expression of a nucleic acid molecule encoding ASGR1 are provided.

Isolated nucleic acid molecules comprising an expression control sequence operably linked to a nucleotide sequence that is a template for a short hairpin RNA that inhibits expression of a nucleic acid are provided. Transgenic pigs comprising an isolated nucleic acid molecule comprising an expression control sequence operably linked to a nucleotide sequence that is a template for one or both strands of a siRNA molecule that inhibits expression of a nucleic acid molecule encoding ASGR1, wherein a transgenic liver from said pig exhibits reduced platelet uptake.

Isolated siRNA molecules that inhibit expression of a nucleic acid molecule encoding ASGR2 are provided. Isolated nucleic acid molecules comprising an expression control sequence operably linked to a nucleotide sequence that is a template for one or both strands of the siRNA molecule that inhibits expression of a nucleic acid molecule encoding ASGR2 are provided. Transgenic pigs comprising an isolated nucleic acid molecule comprising an expression control sequence operably linked to a nucleotide sequence that is a template for one or both strands of a siRNA molecule that inhibits expression of a nucleic acid molecule encoding ASGR2, wherein a transgenic liver from said pig exhibits reduced platelet uptake are provided.

Isolated siRNA molecules that inhibit expression of a nucleic acid molecule encoding MAC1 are provided. Isolated nucleic acid molecules comprising an expression control sequence operably linked to a nucleotide sequence that is a template for one or both strands of the siRNA molecule that inhibits expression of a nucleic acid molecule encoding MAC1 are provided. Transgenic pigs comprising an isolated nucleic acid molecule comprising an expression control sequence operably linked to a nucleotide sequence that is a template for one or both strands of a siRNA molecule that inhibits expression of a nucleic acid molecule encoding MAC1, wherein a transgenic liver from said pig exhibits reduced platelet uptake.

Isolated nucleic acid molecules comprising a nucleotide sequence selected from the group comprising the nucleotide sequence set forth in SEQ ID NO:9; a nucleotide sequence that encodes a polypeptide having the amino acid sequence set forth in SEQ ID NO:10; a nucleotide sequence that encodes a polypeptide having an amino acid sequence that differs by at least one amino acid from the amino acid sequence set forth in SEQ ID NO:10; a nucleotide sequence that encodes a polypeptide having an amino acid sequence having an amino acid other than glycine at position 262 of SEQ ID NO:10; and a nucleotide sequence that encodes a polypeptide having an amino acid sequence having an arginine residue at position 262 of SEQ ID NO:10 are provided.

Human platelets (high intensity, bright regions) are phagocytosed by pig LSEC in vitro. Panel B shows the colocalization of the lysosomal marker (CD107a) with CFSE stained platelets. Panel C shows co-localization of human platelets and lysosomes beneath the endothelial cell surface (horizontal line) after Z-series analysis of the cells shown in panel B.

Figure 9:
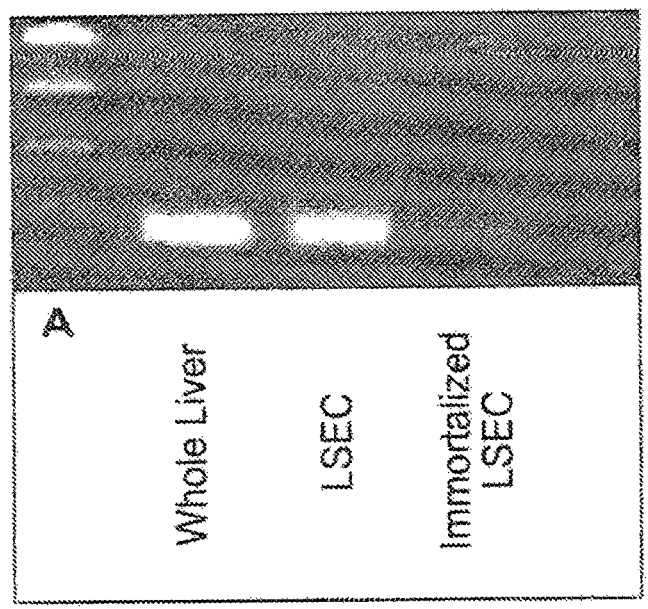
Figure 9:
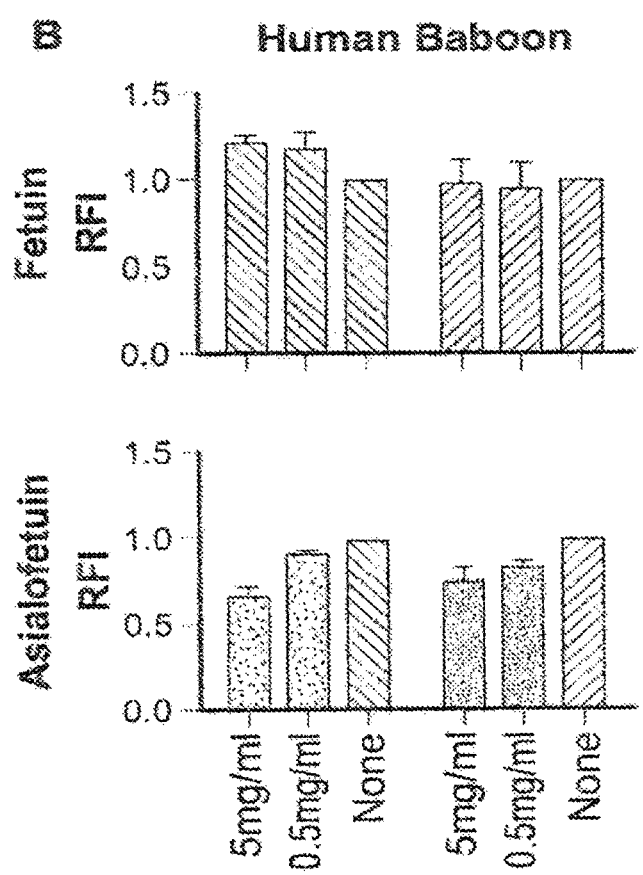
Figure 9:
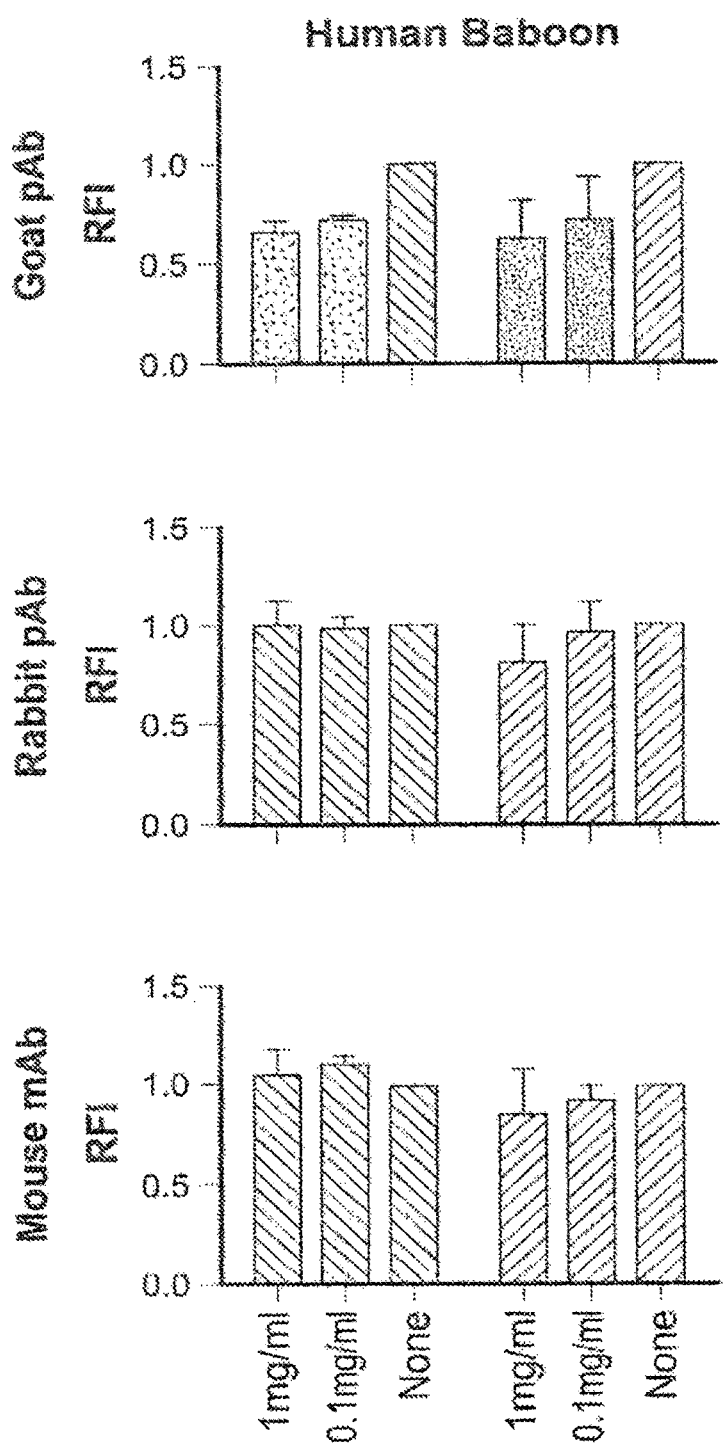
Figure 9:
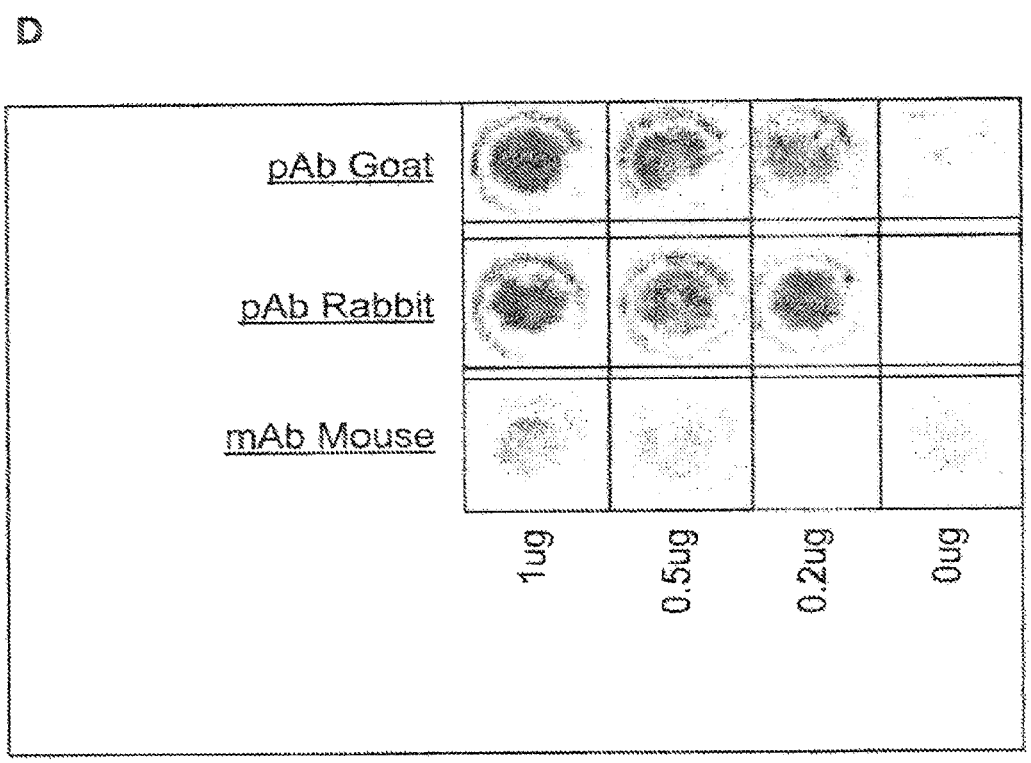

FIG. 9 provides asialoglycoprotein receptor analysis information. Panel A provides a gel showing PCR expression results for the ASGR1 gene in a whole liver sample, early stage LSEC (LSEC) and immortalized, non-phagocytosing LSEC (immortalized LSEC). ASGR1 is expressed at a higher level in whole liver and primary LSECs than in immortalized, non-phagocytosing LSECs. Panel B presents results of an ELISA based fluorescent assay indicating that asialofeutin but not feutin inhibits binding of human (left 3 bars) and baboon (right 3 bars) platelets. The compound of interest was administered to the cells at the indicated concentration (5 mg/ml, 0.5 mg/ml, or none). The RFI is indicated on the y-axis. Panel C presents results of a titration of monoclonal (mouse mAb), polyclonal (rabbit pAb) and (goat pAb) raised against human ASGR1 in a high-throughput phagocytosis assay using human (left 3 bars) and baboon (right 3 bars) platelets. Antibody was administered at 1 mg/ml, 0.1 mg/ml or no antibody control (none). Goat polyclonal antibody inhibits human and baboon platelet binding. Panel D presents results of in-cell immunoblots for antibodies bound to primary pig LSECs. 0 µg, 0.2 µg, 0.5 µg or 1 µg goat polyclonal antibody, rabbit polyclonal antibody, and mouse monoclonal antibody were titrated against primary pig LSECs as indicated. The density of antibodies bound to the pig LSEC correlates with the pattern of platelet inhibition by the three antibodies.

Figure 10:
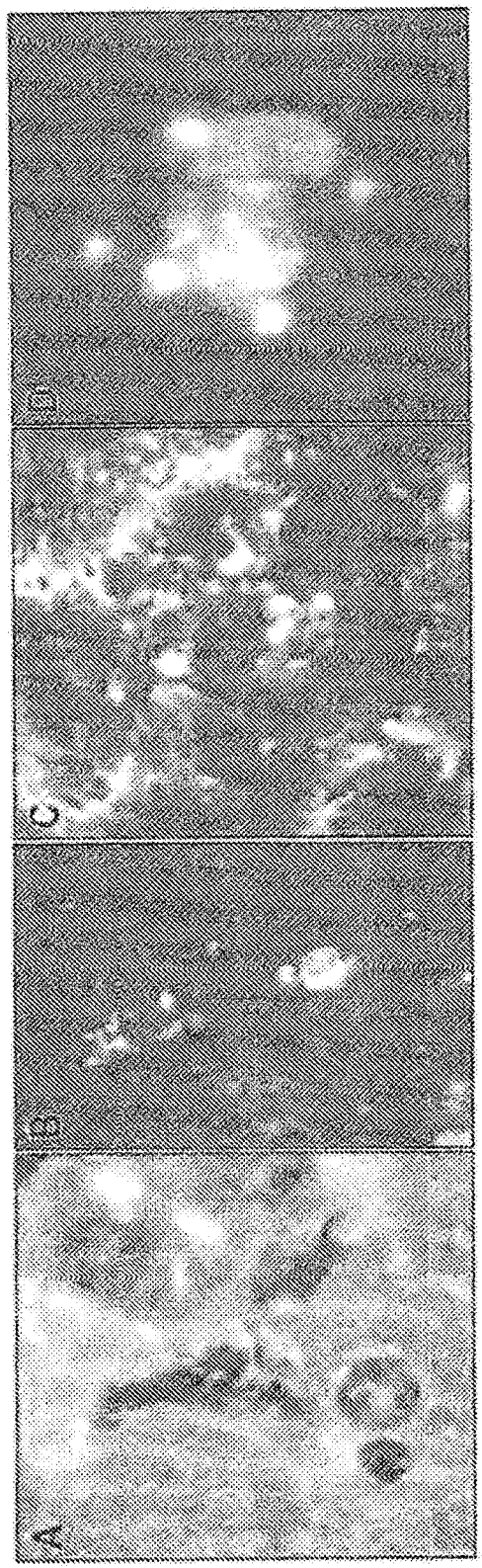

FIG. 10, panel A presents Giemsa staining of ex vivo perfusion biopsies indicating human platelets bound and phagocytosed by sinusoidal Kupffer cells. Panels B, C, and D presents confocal microscopy results. Panel B is a biopsy obtained from ex vivo liver perfused with an anti-Mac1 antibody and platelets. The anti-Mac1 antibody colocalizes with platelets phagocytosed by Kupffer cells. Panel C shows binding specificity of the Mac-1 antibody to Kupffer cells, not LSECs. Panel D shows Mac1 antibody and baboon platelet colocalization in enriched Kupffer cell populations in vitro.

Figure 11:
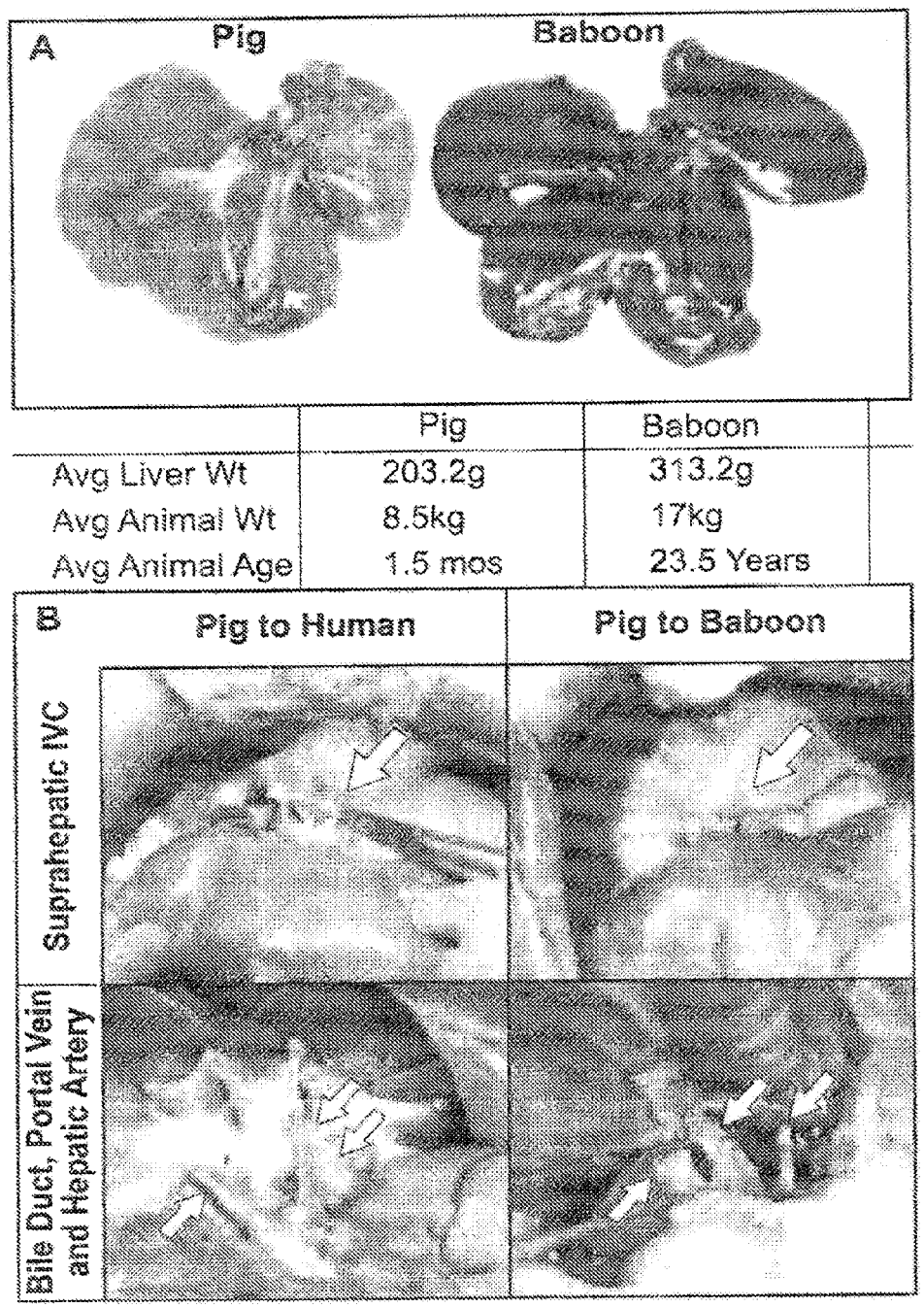

FIG. 11 presents information pertaining to pig to baboon and pig to human liver xenotransplants. Panel A provides size comparisons of pig and baboon mass and liver mass. Donor pigs should weigh approximately 50% of the recipient baboon to avoid development of abdominal compartment syndrome. Panel B details similarities of the surgical procedures between human and baboon suprahepatic IVC, portal vein, hepatic artery and bile duct anastomoses.

Figure 12:
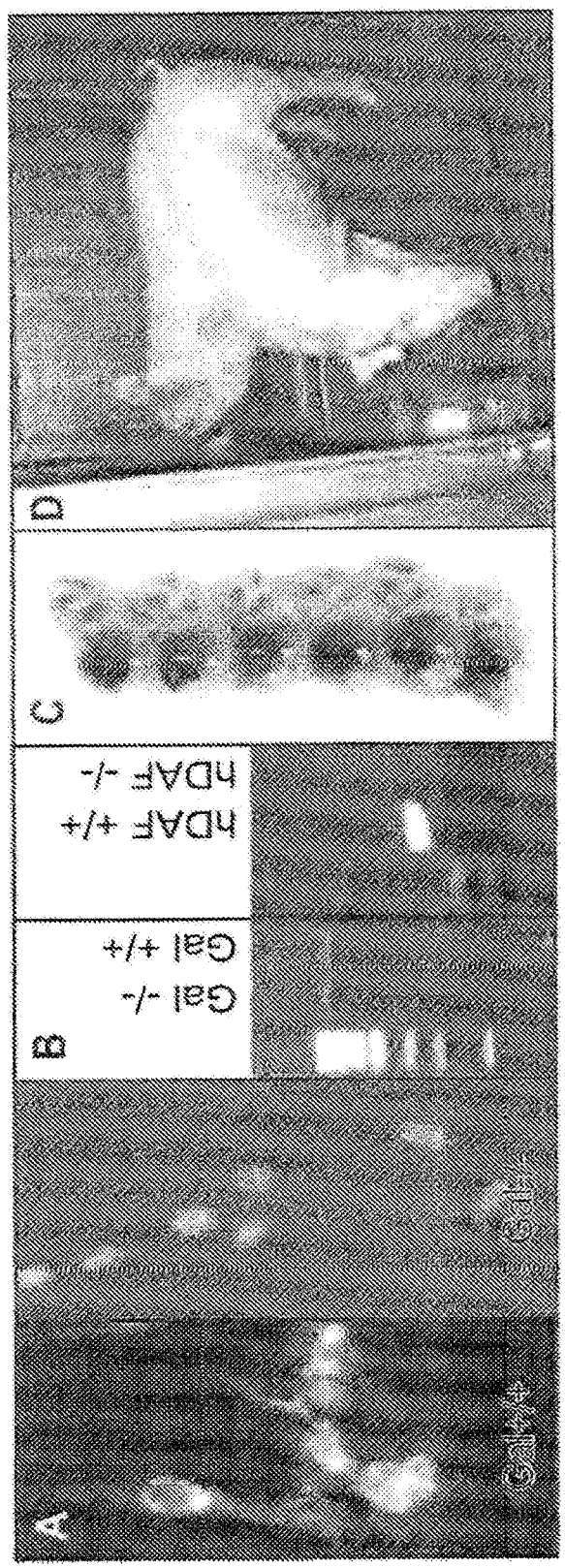

FIG. 12, panel A presents confocal analysis of IB4 lectin labeled gal+/+ and gal−/− fibroblasts. Panel B presents PCR analysis of Gal and hDAF expression. Panel C shows GTKO/hDAF positive pig fetuses produced by SCNT. Panel D shows GTKO/hDAF positive piglets produced by SCNT.

Figure 13:
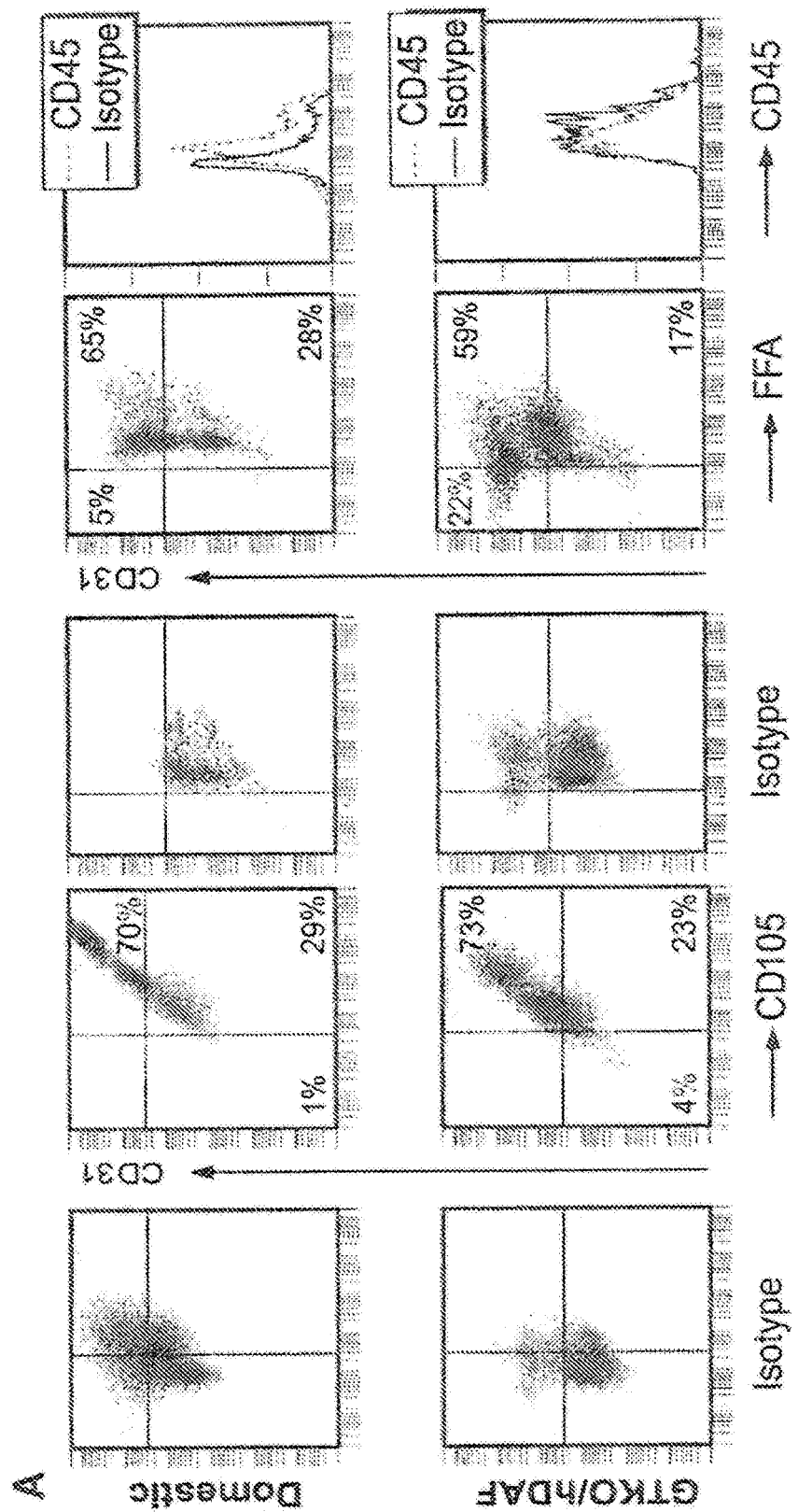
Figure 13:
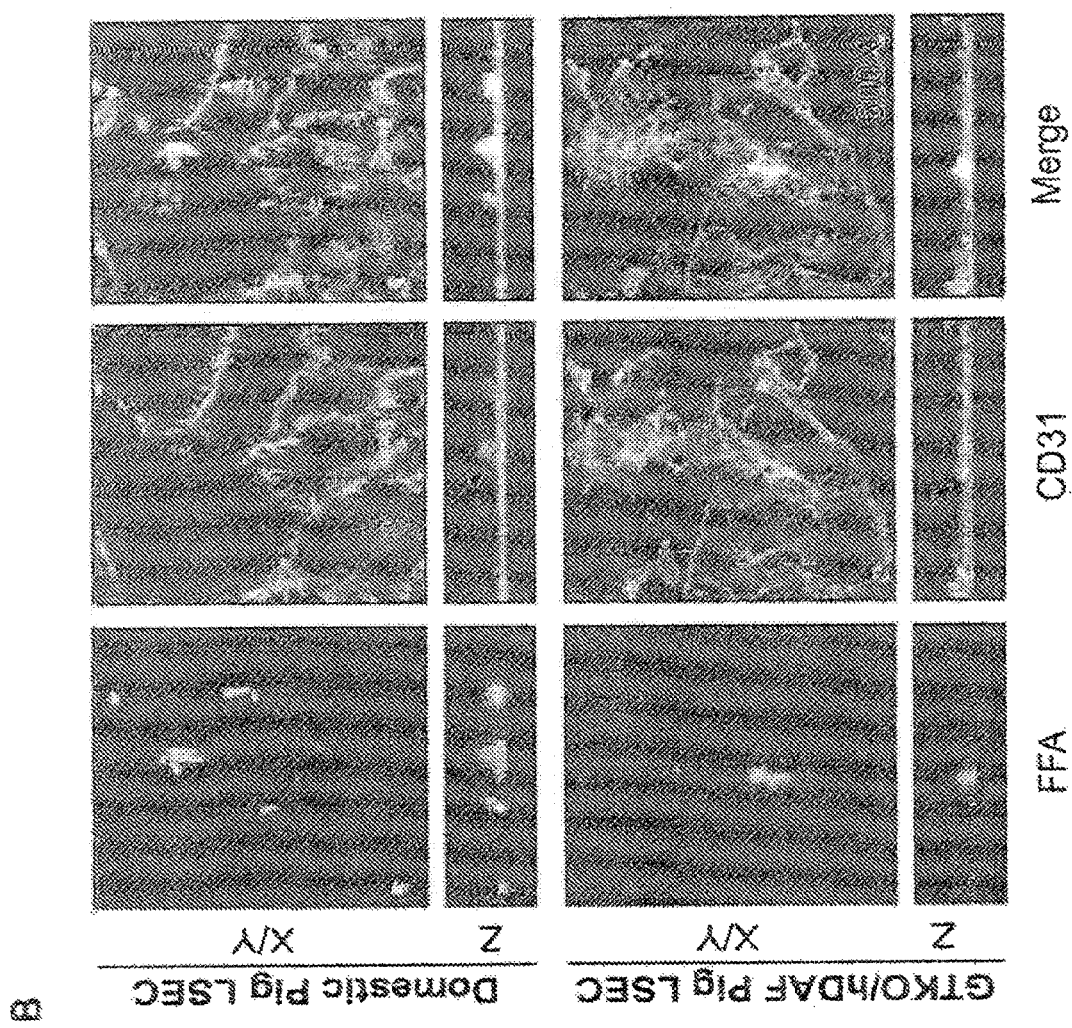

FIG. 13, panel A presents flow cytometry plots of GTKO/hDAF (lower graphs) and domestic (upper graphs) porcine primary LSECs analyzed for CD31 and CD105 (two endothelial cell markers) on the cell surface. Percentages of cells positive for both CD31 and CD105 are indicated on the plots. The middle graphs present data obtained from LSECs incubated with fluorescently labeled FFA-TRITC for 1 hour and examined for cell surface CD31. In the experiment shown, cells positive for FFA comprised 85-95% of the total cell population for both domestic and GTKO/hDAF porcine LSEC cultures. FFA/CD31 double positive cells comprised 60-70% of the total cell population. On average, hepatocytes labeled with cytokeratin 18 constituted less than 5% of the primary cells. The histograms on the right indicate little or no CD45 (dashed line) is present on the porcine primary LSECS; isotype is indicated with a contiguous line. FIG. 13, panel B presents a series of micrographs of GTKO/hDAF (lower rows, GTKO/hDAF pig LSEC) and domestic (upper rows, domestic pig LSEC) porcine primary LSECs. Micrographs of an X/Y section are indicated by X/Y; micrographs of Z axis indicated by Z were obtained by stacking and deconvoluting approximately 30 X/Y sections. Cells were examined for FFA fluorescence (FFA), CD31 expression (CD31) and FFA, CD31 and DAPI staining of nucleic acids (merge). Arrows indicate FFA and CD31 co-localization and indicate that FFA is inside the cell. Images are representative of three experiments. Panels A and B indicate that four day old primary LSEC cultures contain primarily CD31 and CD105 positive, CD45 negative, FFA phagocytosing LSECs.

Figure 14:
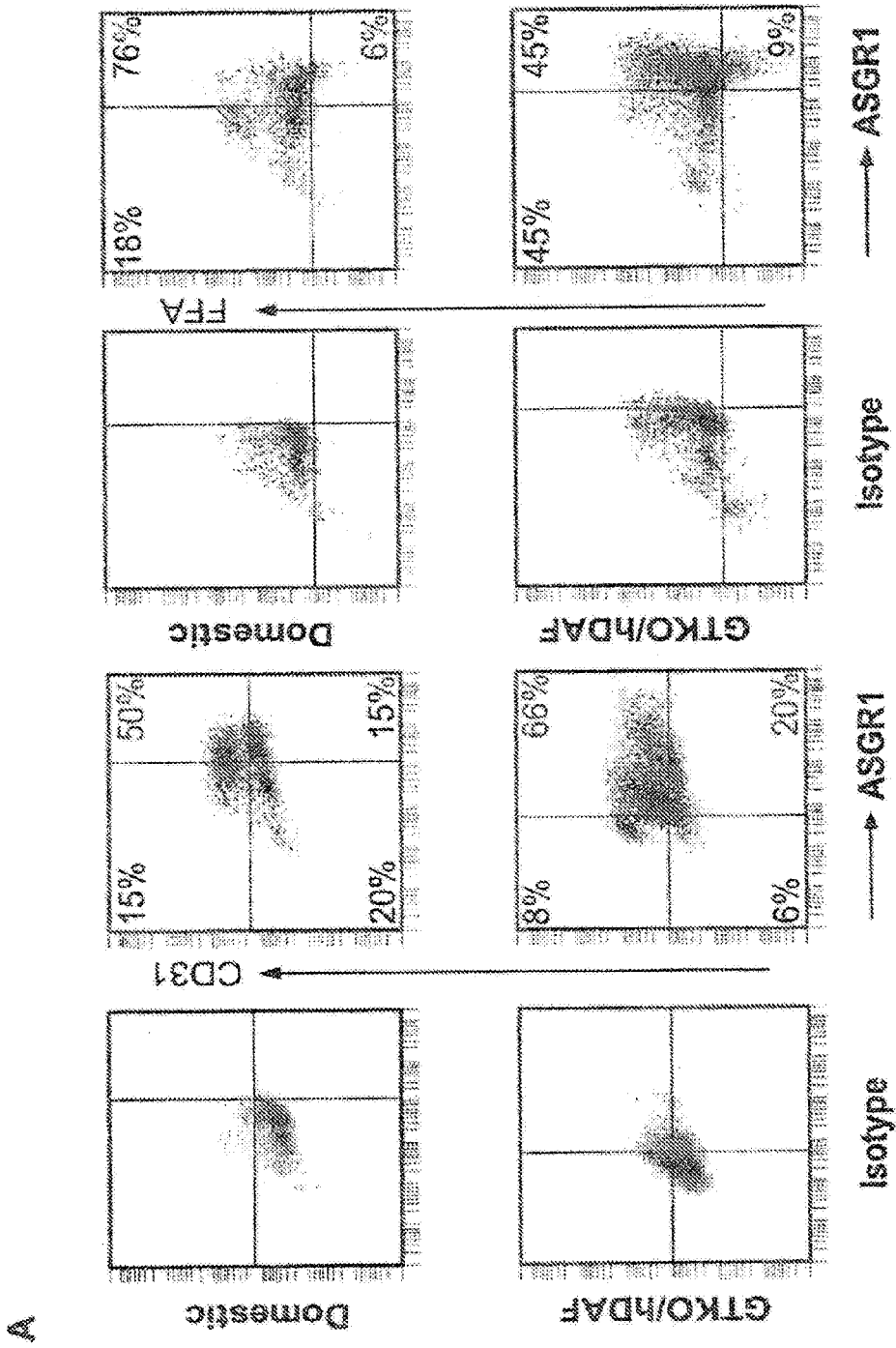
Figure 14:
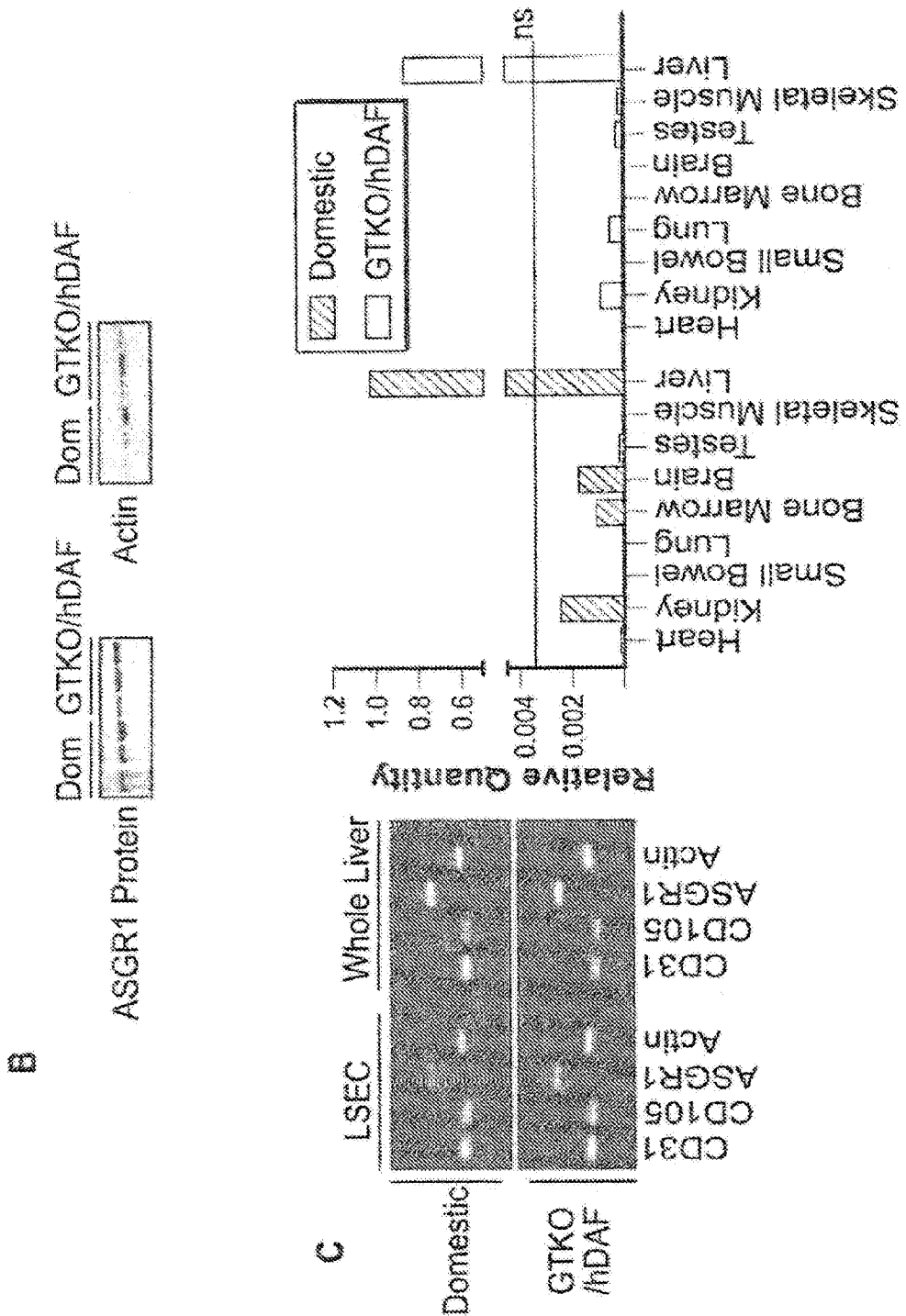
Figure 14:
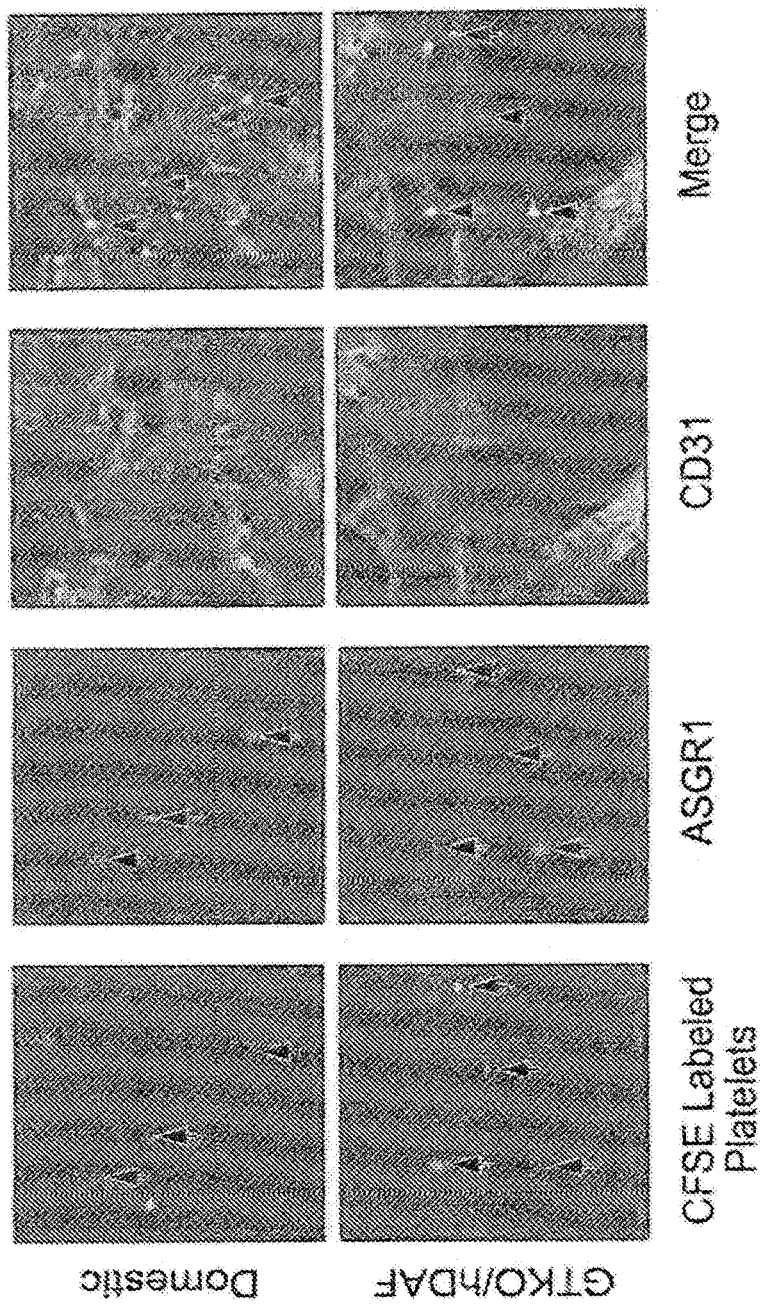

FIG. 14 presents a collection of results from experiments evaluating ASGR1 expression in porcine livers and LSECs. Panel A presents results of flow cytometry analysis of domestic (four upper dot plots) or GTKO/hDAF (four lower dot plots) porcine primary LSECs probed for ASGR1 and either CD31 (left four dot plots) or FFA uptake (right four dot plots). Results from isotype controls are shown in the dot plots on the left of each group. LSEC cultured for four days were predominantly ASGR1/CD31 double positive and ASGR1/FFA double positive. Representatives from three experiments are shown. Panel B presents immunoblots of whole cell lysates obtained from primary domestic and GTKO/hDAF cell cultures. Three individual samples from domestic LSEC cultures (DOM) and three individual samples from GTKO/hDAF cultures (GTKO/hDAF) were prepared and subjected to immunoblot analysis as described elsewhere herein. The membranes were incubated with either anti-ASGR1 antibodies (ASGR1 protein) or anti-β actin antibodies (actin).

Panel C presents results of PCR analysis of porcine LSECS and tissues. The left images are of PCR reaction products resolved on a gel. The products in the top image were obtained from PCR amplification of mRNA from domestic LSECs (four left lanes) or whole liver tissue templates (four right lanes). The products in the lower image were obtained from PCR amplification of GTKO/hDAF LSECs (four left lanes) or whole liver tissue templates (four right lanes). Lanes indicated by CD31, CD105, ASGR1, and β-actin contain reaction product from CD31, CD105, ASGR1 and β-actin specific primers, respectively. ASGR1 is amplified from both domestic and GTKO/hDAF porcine LSECs and whole liver tissue. The graph on the right depicts the results of quantitative PCR amplification of ASGR1 from mRNA obtained from the indicated tissues: heart, kidney, small bowel, lung, bone marrow, brain, testes, skeletal muscles and liver. Results from domestic pig tissue are indicated with lined bars; results from GTKO/hDAF pig tissue are indicated with empty bars. The bars indicate ASGR1 expression relative to β-actin expression. The line indicates the threshold for a significant level of cycle time. The results are the mean of three biological replicates. ASGR1 relative expression in liver tissue from domestic and GTKO/hDAF pigs is significantly higher than in other tissues. Panel D presents confocal images obtained from domestic (top) and GTKO/hDAF (bottom) primary LSEC cultures incubated for 1 hour with CFSE-labeled human platelets then probed for ASGR-1 and CD31. The left panes show CFSE-labeled platelets, the middle left panes show ASGR1, the middle right panes show CD31, and the right panes show a merge of the images. Arrows indicate co-localization of porcine ASGR1 with human platelets in LSECs. Cells positive for CD31 staining and CFSE-labeled human platelet uptake were also ASGR1 positive.

Figure 15:
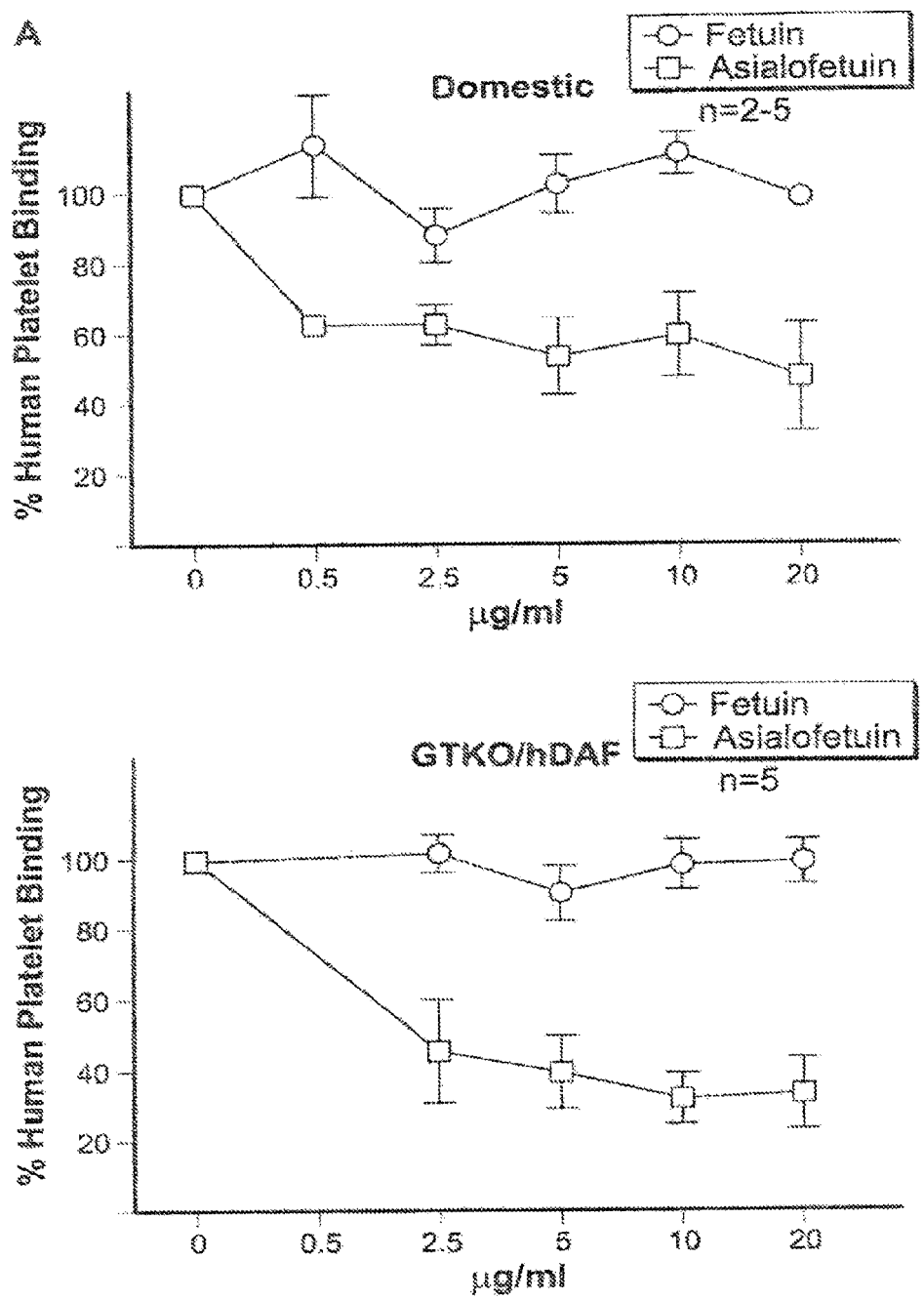
Figure 15:
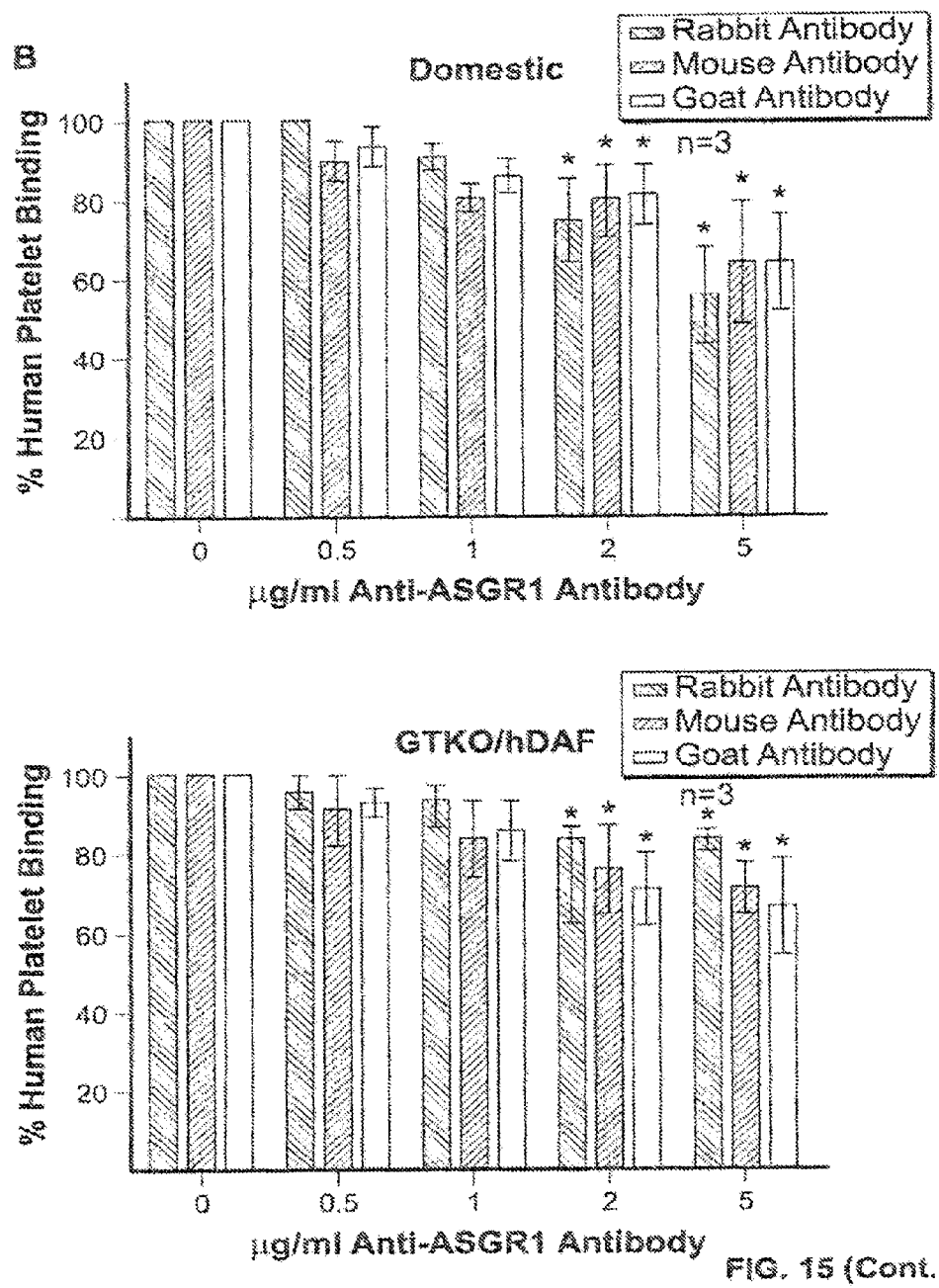

FIG. 15 panel A presents graphs depicting the impact of asialofetuin on platelet binding by LSECs. The percent of human platelet binding by LSECs cultured from either domestic (top) or GTKO/hDAF (bottom) pigs is indicated on the y-axis. The concentration of the compound of interest added to the cultures is indicated on the x-axis (μg/ml). Results obtained after incubation with fetuin are indicated with circles. Results obtained after incubation with asialofetuin are indicated with squares. Error bars indicate the standard deviation about the mean; n=2-5 for domestic pigs and n=5 for GTKO/hDAF pigs. Platelet binding after incubation with asialofetuin is significantly reduced.

Panel B presents graphs depicting the impact of anti-ASGR1 antibodies on platelet binding by LSECs. The percent of human platelet binding by LSECs cultured from either domestic (top) or GTKO/hDAF (bottom) pigs is indicated on the y-axis. The antibody concentration is indicated on the x-axis. Results obtained after incubation with rabbit anti-ASGR1 polyclonal antibodies (rabbit antibody) are indicated with slashed bars; results obtained after incubation with mouse monoclonal anti-ASGRI (mouse antibody) are indicated with hatched bars; results obtained after incubation with goat anti-ASGR1 polyclonal antibodies are indicated with empty bars. Bars indicate the mean±standard deviation from n=3. Asterisks indicate a significance of P≤0.05 when compared to no antibody control as analyzed by Anova and Dunnett's post hoc test. Goat and rabbit polyclonal anti-ASGR1 antibodies at 5.0 μg/ml resulted in statistically significant inhibitions to levels ranging between 63.9%-66.7% and 56.1%-83.5% of untreated controls, respectively. Mouse monoclonal anti-ASGR1 antibody with reactivity toward ASGR1 and ASGR2 resulted in statistically significant inhibitions of platelet binding to levels ranging between 64.1%-71.2% of untreated controls.

Figure 16:
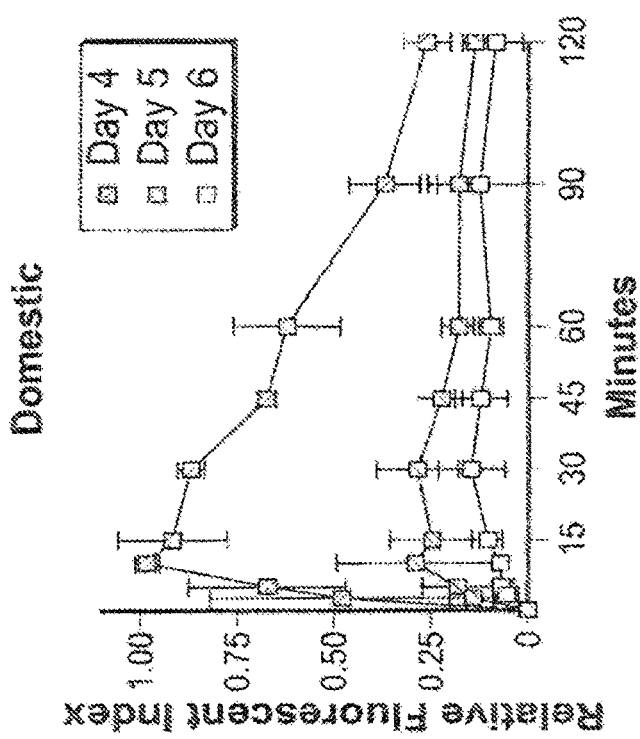
Figure 16:
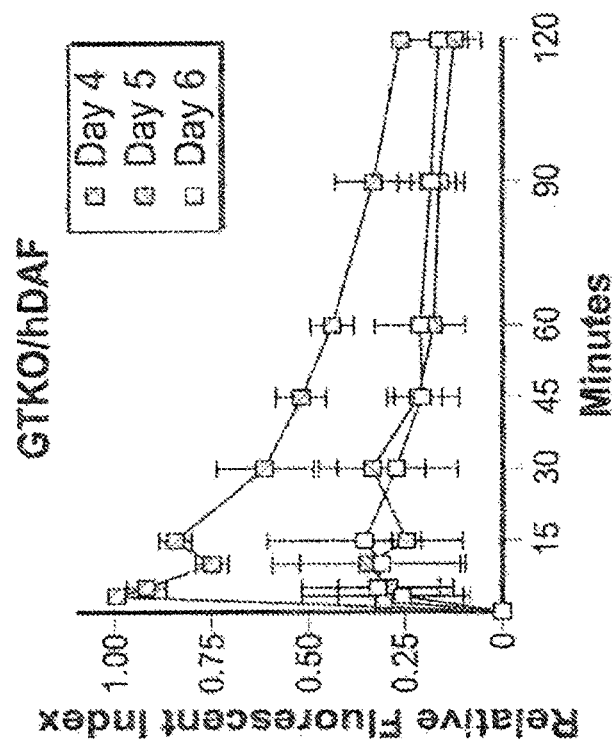
Figure 16:
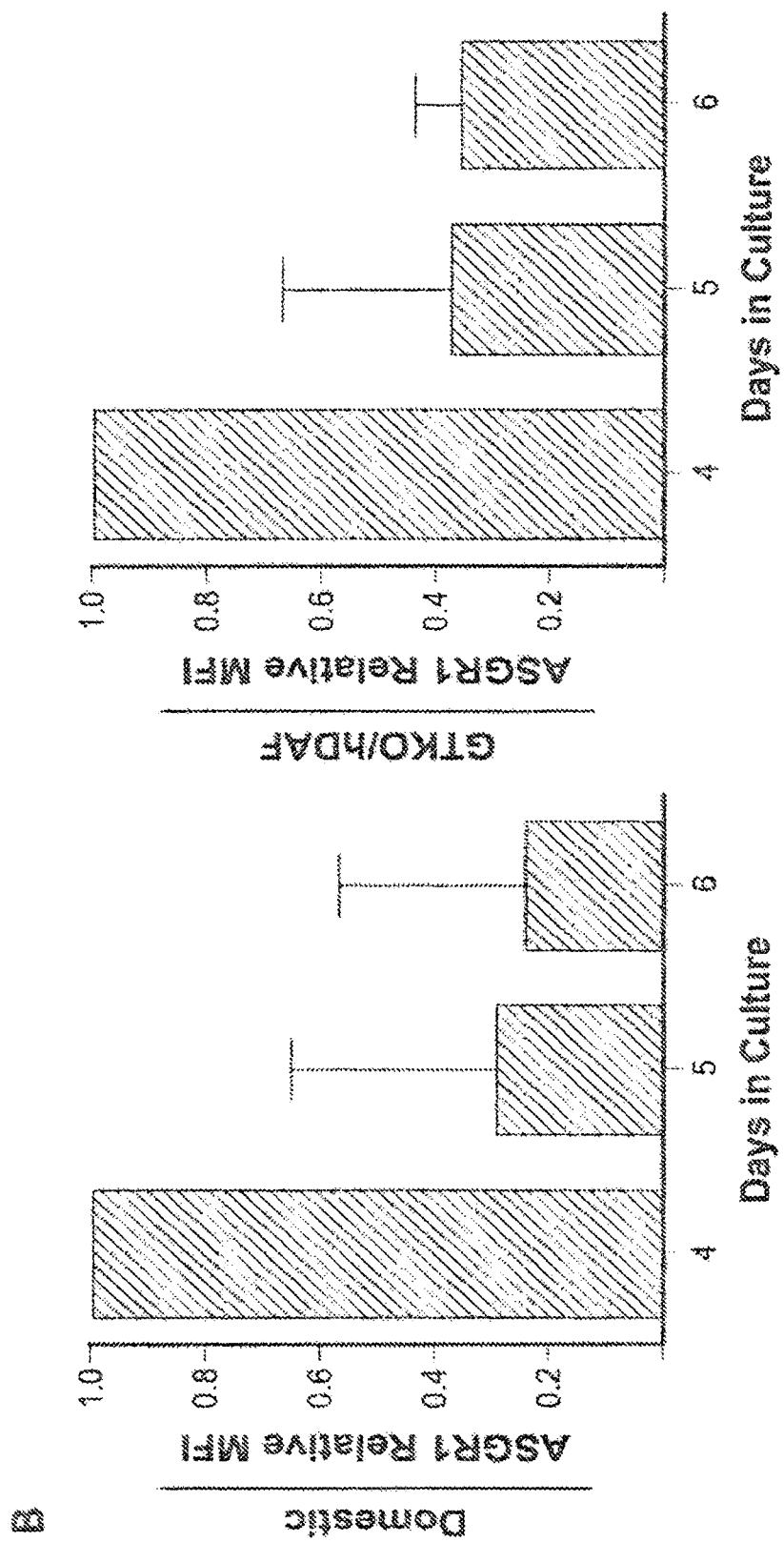
Figure 16:
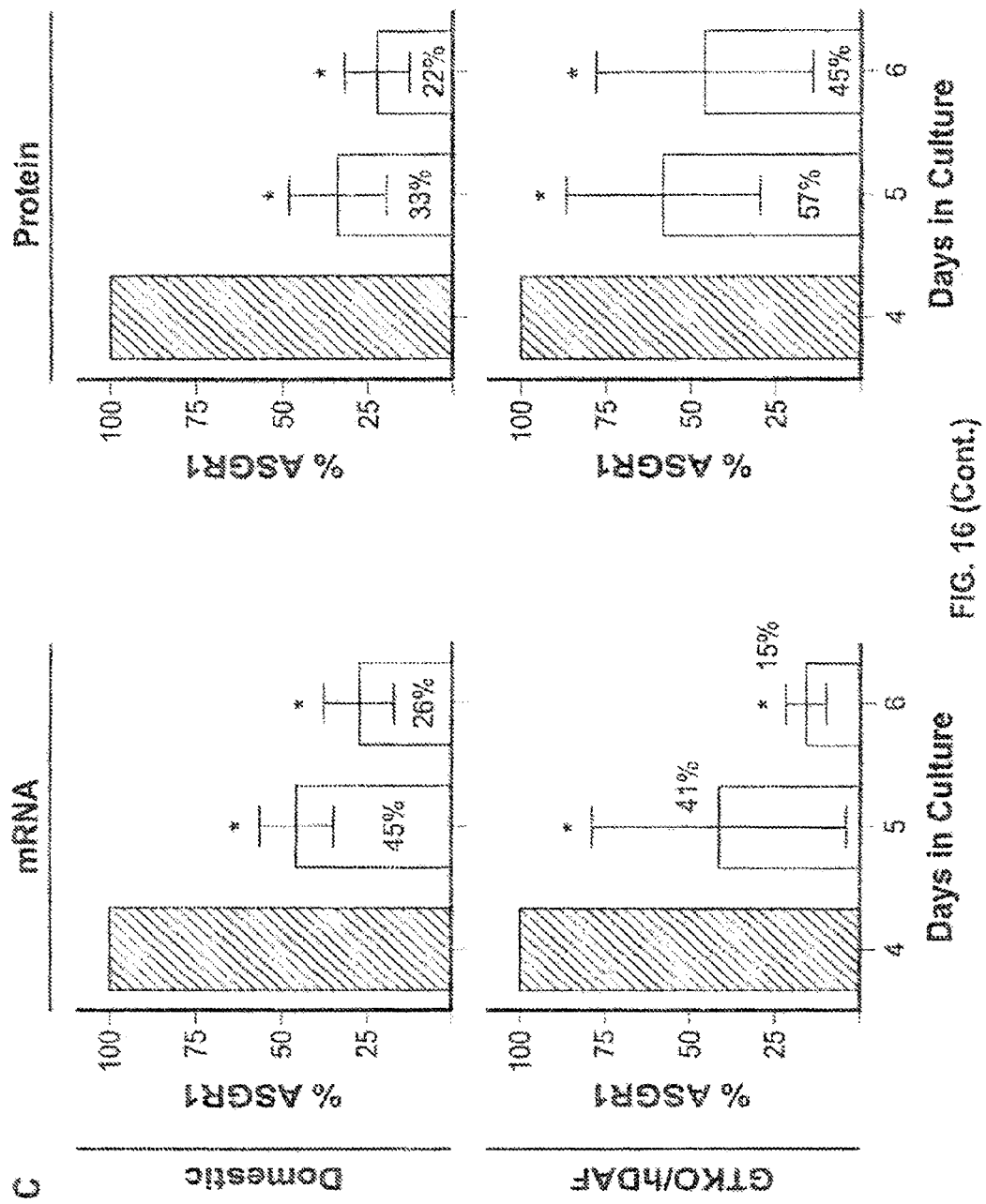

FIG. 16 presents panels pertaining to loss of ASGR1 expression and loss of platelet phagocytosis. Panel A presents the mean relative fluorescent index (y-axis) of domestic (left) and GTKO-hDAF (right) primary LSECs at the indicated timepoint (x-axis) after addition of CFSE-labeled human platelets. Platelet binding by LSECs cultured for four days (slashed squares), five days (hatched squares), or six days (empty squares) is shown on the graph. LSECs cultured for five or six days exhibit significantly reduced platelet binding when compared to LSECs cultured for four days. Panel B presents results of flow cytometry analysis of ASGR1 cell surface expression. The relative mean fluorescence index of domestic (left) and GTKO-hDAF (right) primary LSECs is indicated on the y-axis. RFI of LSECS cultured for four days (4), five days (5) or six days (6) are indicated. ASGR1 expression in primary LSECs cultured for five or six days is significantly lower than ASGR1 expression in primary LSECs cultured for four days. Panel C presents four graphs depicting the percent of ASGR1 expression in primary LSECs isolated from domestic (top graphs) and GTKO/hDAF (bottom graphs). The left graphs present results of quantitative PCR on mRNA obtained from primary LSECs cultured for four (hatched bars), five or six days. ASGR1 mRNA levels in domestic LSECs cultured for five days and six days were 45% and 26% respectively of cells cultured for four days. ASGR1 mRNA levels in GTKO/hDAF LSECs cultured for five and six days were 41% and 15% respectively of cells cultured for four days. The right graphs present results of protein expression analysis using immunoblots of proteins obtained from primary LSECs cultured for four, five or six days. ASGR1 protein levels in domestic LSECs cultured for five days and six days were 33% and 22% respectively of cells cultured for four days. ASGR1 protein levels in GTKO/hDAF LSECs cultured for five and six days were 57% and 45% respectively of cells cultured for four days. The graphs show the mean of three experiments with error bars indicating standard deviation. Asterisks indicate a significance of P≤0.05 as analyzed by ANOVA and Dunnett's post hoc test.

Figure 17:
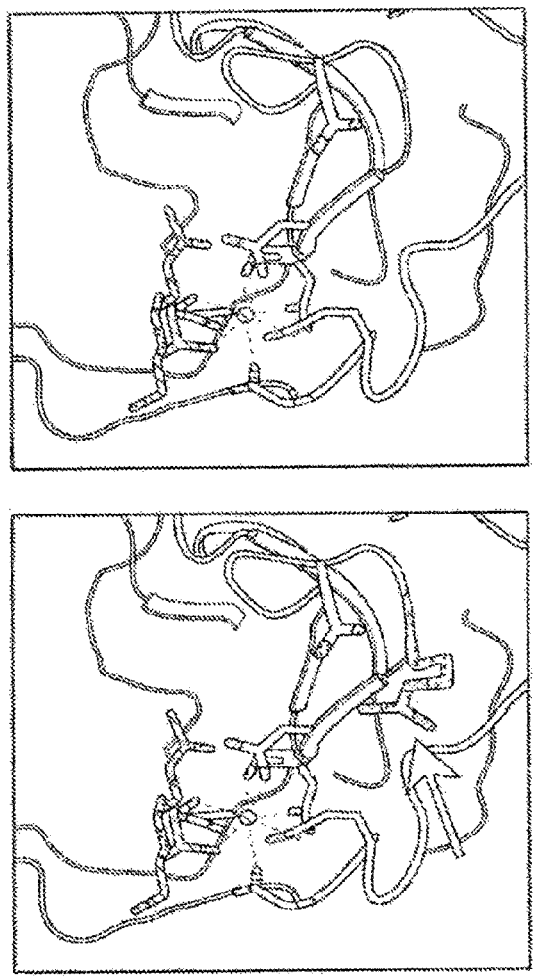
Figure 17:
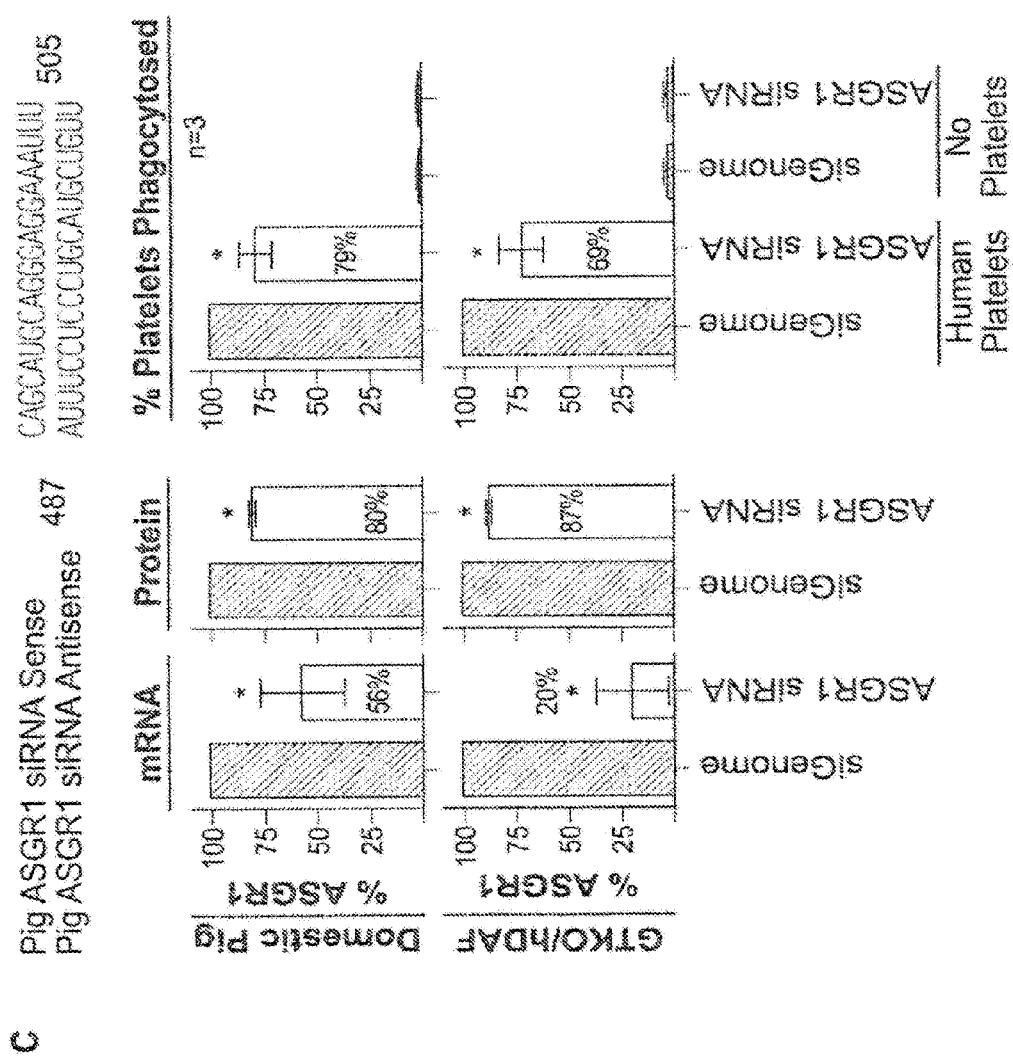

FIG. 17, panel A presents an amino acid sequence alignment of human and pig ASGR1 saccharide binding sites. The human ASGR1 saccharide binding site is set forth in SEQ ID NO:13; the porcine ASGR1 saccharide binding site comprises amino acid residues 236 to 268 of SEQ ID NO: 10. The human and porcine amino acid sequences differ by three residues including an arginine in the human sequence that is a glycine in the porcine sequence (indicated by a box). Panel B presents ribbon and stick models of the human and predicted porcine ASGR1 binding sites with an N-acetylglucosamine in the binding site modeled by the Pymol Molecular Graphics System. An arrow indicates the arginine at amino acid position 262 (A262) in the human ASGR1 amino acid sequence that is a glycine (G262) in the porcine ASGR1 near the saccharide binding site.

Panel C presents information obtained from ASGR1 double-stranded RNA siRNA sense (SEQ ID NO:11) and antisense (SEQ ID NO:12) oligonucleotides utilized in ASGR1 siRNA experiments. Porcine primary LSECs established from Domestic (top graphs) and GTKO/hDAF (bottom graphs) were transfected with ASGR1 siRNA coated transfection beads or non-specific siGENOME coated transfection beads. The graphs on the left present the results of quantitative PCR and immunoblotting performed on LSECs 48 hours after siRNA treatment (mean±standard deviation). ASGR1 mRNA levels in LSECs post ASGR1 siRNA treatment (empty bars) were 56% (domestic) or 20% (GTKO/hDAF) that of non-specifically treated cells (siGenome, slashed bars). ASGR1 protein levels in LSECs post ASGR1 siRNA treatment were 80% (domestic) or 87% (GTKO/hDAF) that of non-specifically treated cells (siGenome, slashed bars). Asterisks indicate significantly different levels; n=3. The graphs on the right present the percent of platelets phagocytosed by LSECs 48 hours after siRNA treatment as compared to the percent of platelets phagocytosed by LSECs 48 hours after transfection with non-specific siGenome oligonucleotides. Data from non-specifically treated LSECs (siGenome) are indicated by slashed bars; data from anti-ASGR1 siRNA treated LSECs are indicated by empty bars (mean±standard deviation, n=3). Subsequent to anti-ASGR1 siRNA treatment, domestic LSECs exhibited 79% platelet phagocytosis and GTKO/hDAF LSECs exhibited 69% platelet phagocytosis. Asterisks indicate significantly different levels; P≤0.05 when compared to siGenome controls as analyzed by the Anova and Dunnett's post hoc test. The middle right and far right bars indicate background fluorescence of cells not exposed to CFSE-labeled platelets (No platelets).

Figure 18:
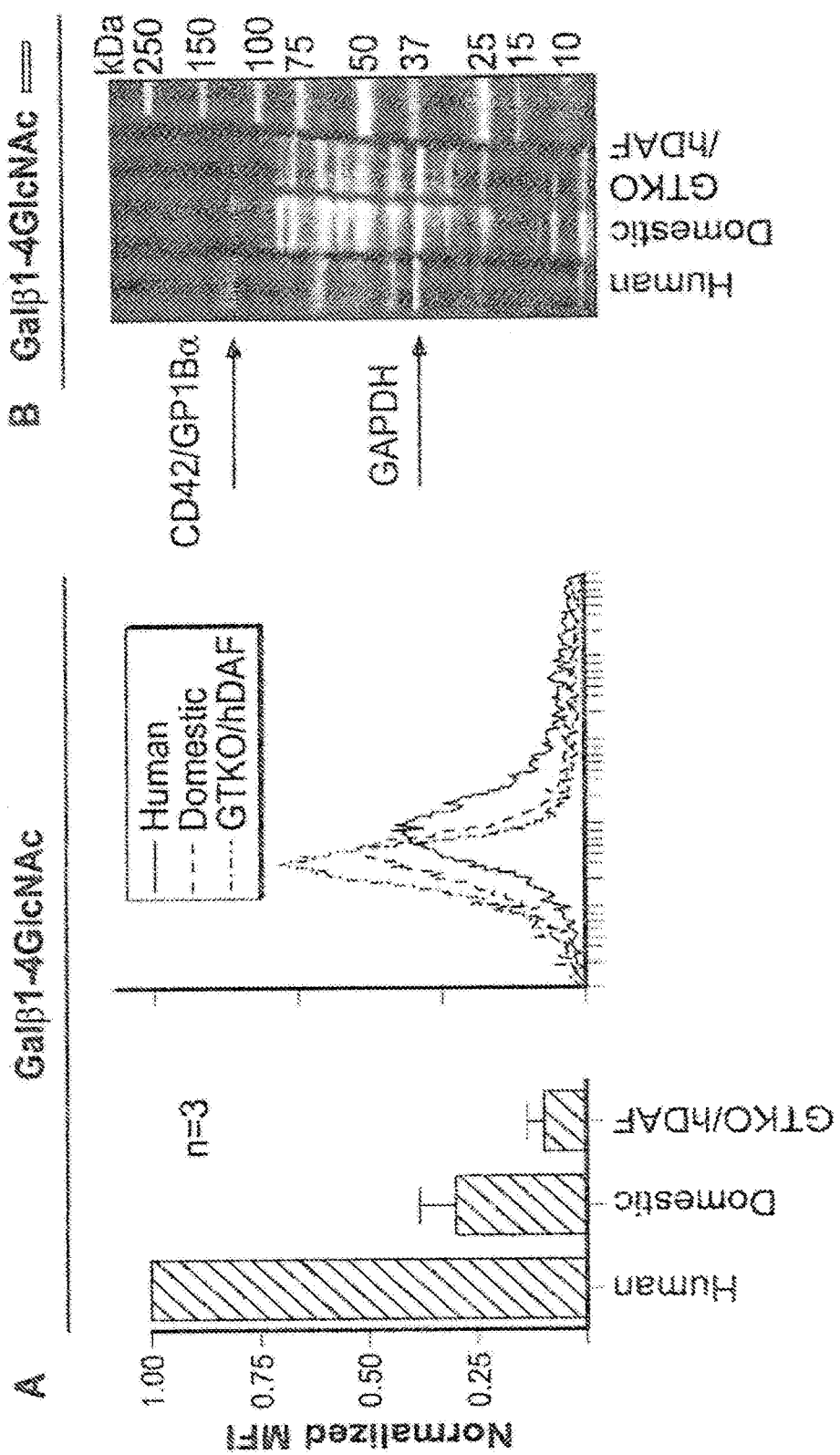
Figure 18:
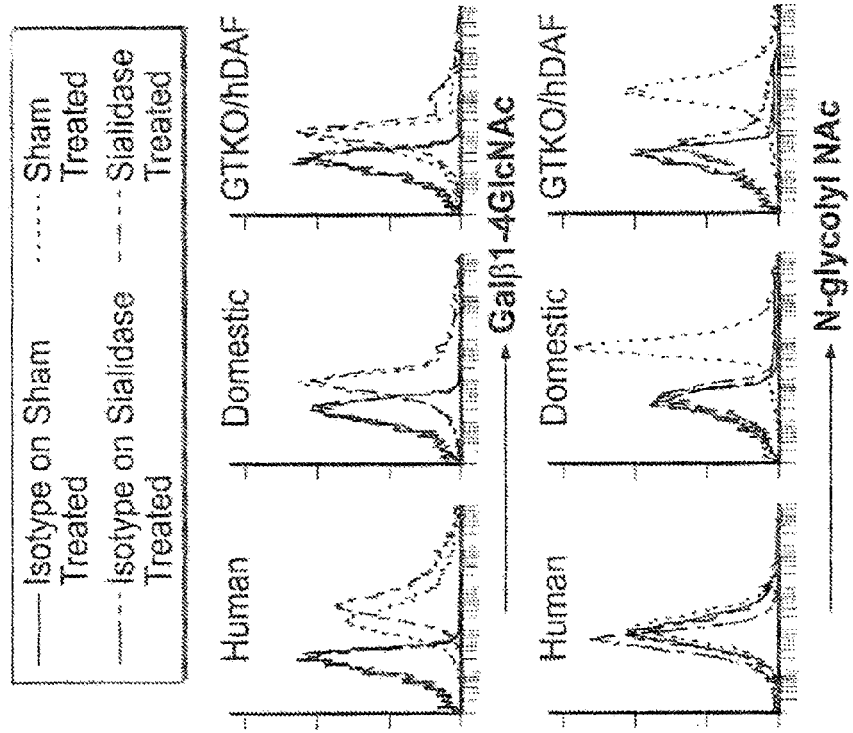
Figure 18:
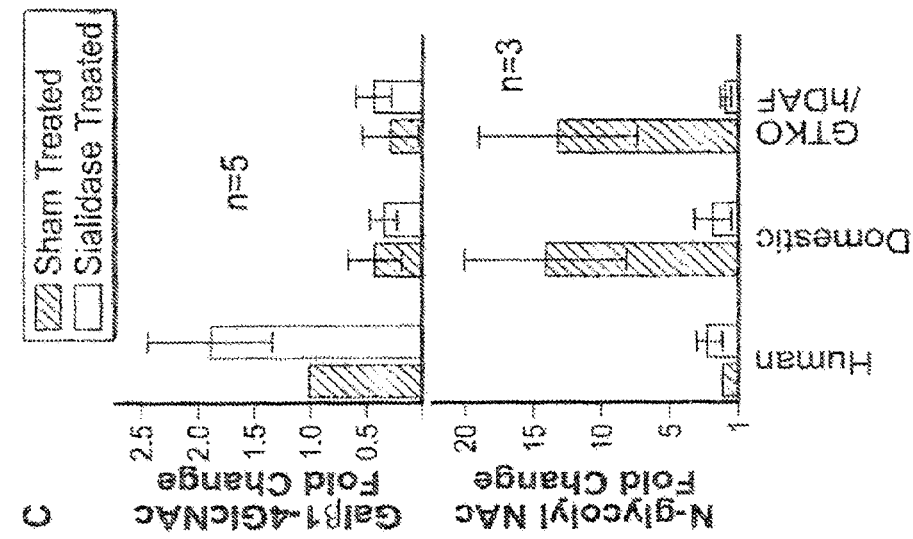
Figure 18:
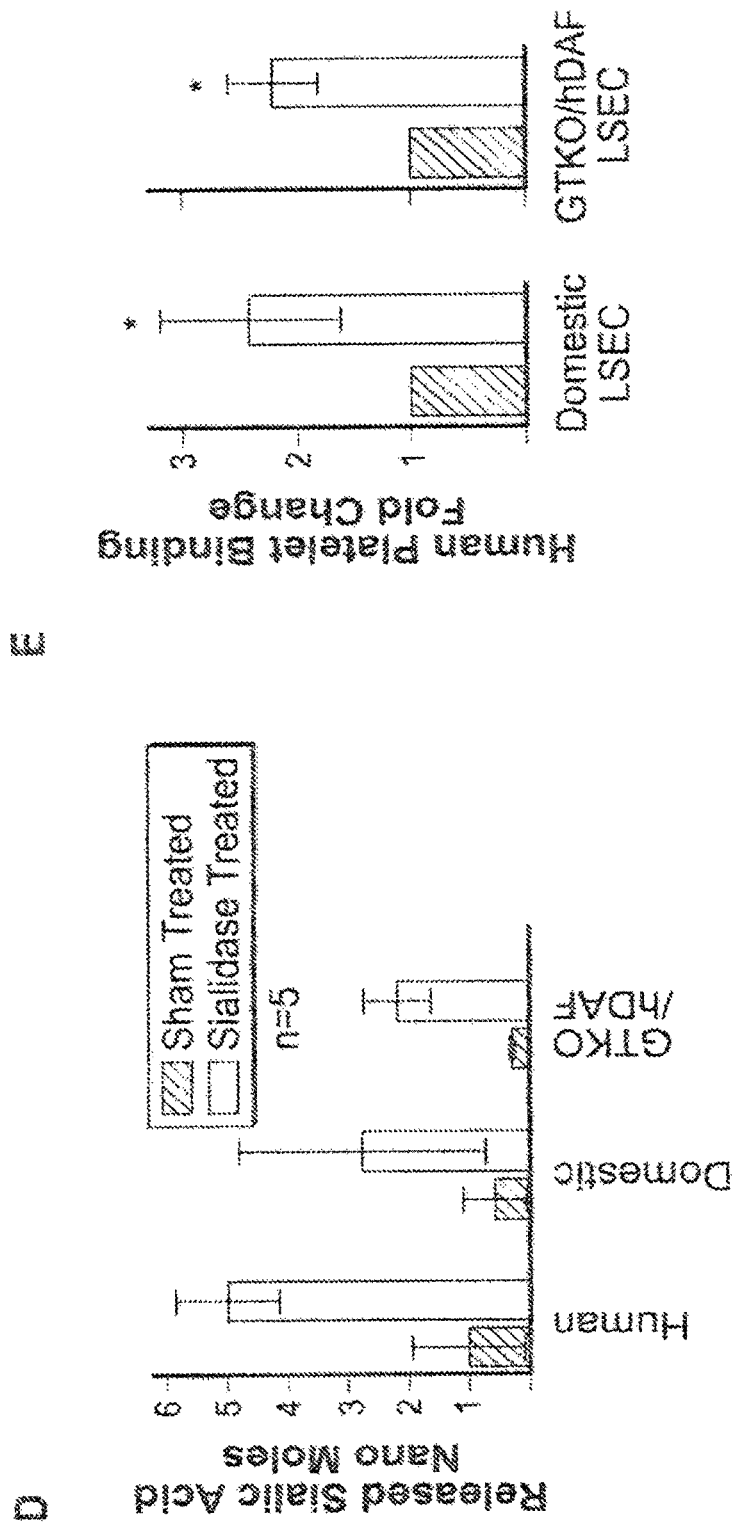

FIG. 18 presents a series of panels with data obtained from investigations analyzing Galβ1,4 glcNAc. Panel A depicts a bar graph showing mean fluorescence index (MFI) of human, domestic and GTKO/hDAF porcine platelets after incubation with ECA-PE, n=3. The MFI of human platelets is significantly higher than porcine platelets, indicating a higher level of exposed Galβ oligosaccharide. The MFI of porcine platelets decreases compared to human platelets', indicating a lower level of exposed Galβ oligosaccharide. A representative histogram is shown on the right. Data from human platelets is presented with a solid line, data from domestic platelets is presented with a dashed line, and data from GTKO/hDAF platelets is presented with dash-dot line. Panel B depicts an immunoblot/lectin blot. Human platelet lysate is in the left lane, porcine domestic platelet lysate (domestic) is in the second lane, GTKO/hDAF porcine platelet lysate is in the third lane and a molecular weight marker is in the fourth lane. Arrows indicate GAPDH and CD42/GP1Bα. Terminal Galβ oligosaccharides are present on numerous proteins in each platelet lysate.

The graphs in panel C indicate the fold change in either Galβ1,4 glcNAc levels (top graph, n=5) or N-glycolyl neuraminic acid (N-glycolyl NA, bottom graph, n=3). Data from sham-treated platelets are indicated by slashed bars; data from sialadase A treated platelets are indicated by empty bars. Error bars indicate standard deviation. The left pair of bars presents data obtained from human platelets (human), the middle pair of bars presents data obtained from domestic porcine platelets (domestic) and the right pair of bars presents data obtained from GTKO/hDAF porcine platelets (GTKO/hDAF). Sialadase A treatment removes N-glycolyl neuraminic acid from porcine platelets. Representative histograms of human, domestic and GTKO/hDAF platelets are shown on the right. The isotype on sham treated platelets trace is continuous; isotype on sialadase treated platelet trace is dash dot; the sham treated platelets trace is dots; the sialadase treated platelets trace is dashed.

Panel D depicts a graph of the sialic acid molecules released into the supernatant after treatment of human, domestic and GTKO/hDAF platelets with sialadase. The concentration of released sialic acid molecules (nmoles/$5 \times 10^8$ platelets) is indicated on the y-axis. Results from sham-treated platelets are indicated with slashed bars; results from sialadase-treated platelets are indicated with empty bars. The platelet type is indicated on the x-axis: human, domestic porcine or GTKO/hDAF. Error bars indicate standard deviation, n=5. In this experiment, the concentration of sialic acid in the supernatant was 5 nmol/$5 \times 10^8$ human platelets, 2.8 nmol/$5 \times 10^8$ domestic porcine platelets, and 2.2 nmol/$5 \times 10^8$ GTKO/hDAF platelets. Panel E presents results of a platelet phagocytosis assay performed using CSFE-labeled sham treated (slashed bars) or desialated (empty bars) human platelets and domestic porcine LSECs (domestic, left) or GKTO/hDAF porcine LSECs (GTKO/hDAF, right). Binding and phagocytosis of desialated CFSE labeled human platelets relative to sham treated platelets is indicated on the y-axis. Porcine LSECS, from both domestic and GTKO/hDAF, exhibited approximately a two-fold increase in binding and phagocytosis of desialated human platelets as compared to untreated human platelets. In this experiment, the increase in platelet binding and the increase in exposed Galβ post treatment are proportional.

FIG. 19 depicts a schematic of the sequence alterations in exemplary knockout pigs. Panel A presents portions of the wild-type and disrupted ASGR1 nucleotide sequences. A portion of the wild-type ASGR1 nucleotide sequence (WT) is shown in the top line (SEQ ID NO:14). The same region of the ASGR1 nucleotide sequence from a cell line used for nuclear transfer (NT), a porcine fetus (Fetus), and five viable piglets (Piglet 1-5) are shown in the three bottom lines. The disrupted ASGR1 nucleotide sequence from the depicted example is a 26 nucleotide deletion (SEQ ID NO:15). Dashes indicate the portion of the nucleotide sequence where the deleted nucleotides would occur in the wild-type sequence.

Figure 20:
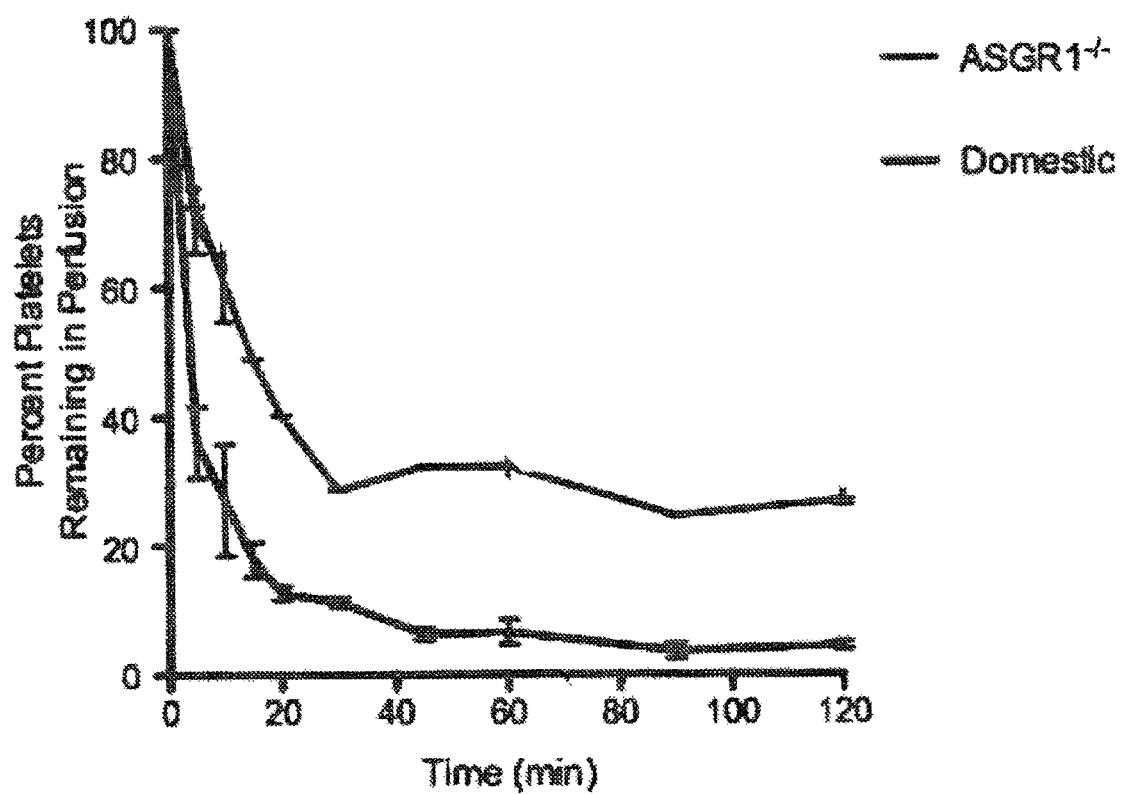
Figure 20:
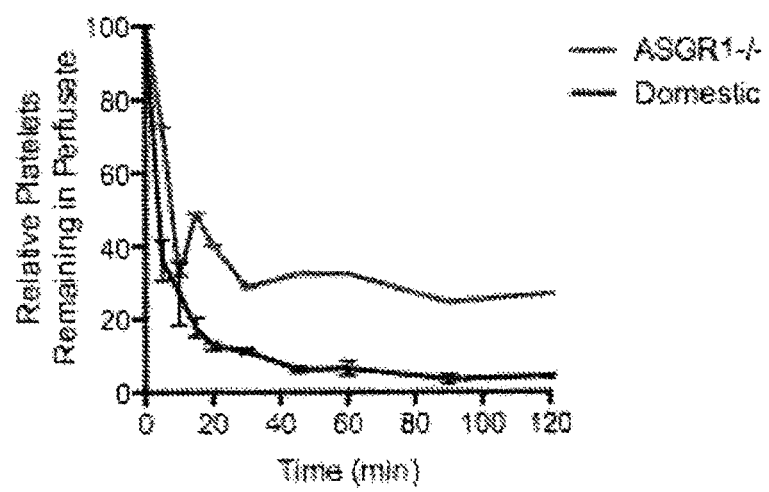

FIG. 20 depicts a graph of data obtained from perfusion experiments involving porcine livers perfused with human platelets. The post-perfusion initiation time in minutes is indicated on the x-axis (Time); the percent of human platelets remaining in the perfusion solution is indicated on the y-axis (Percent Platelets Remaining in Perfusion). Average results obtained from wild-type pig livers (Domestic) are plotted on the graph. Results obtained from an ASGR1 single knockout pig liver (ASGR1-/-) are plotted on the graph.

DETAILED DESCRIPTION OF THE INVENTION

The present application relates to the discovery that liver sinusoidal endothelial cells and Kupffer cells in a pig liver phagocytose human platelets. While not being limited by mechanism it is possible that the liver sinusoidal endothelial cells interact with hepatocytes to facilitate the disposal of the phagocytosed platelets. Again while not being limited by mechanism, receptors on the LSEC and Kupffer cells may mediate binding to the platelets. Possible receptors may include the ASGR1 and ASGR2 receptors on liver sinusoidal endothelial cells and Mac1 on the Kupffer cells. While not being limited by mechanism, receptors on the LSEC and Kupffer cells may interact with a ligand on the platelet membrane; possible ligands may include β-GlcNAc-terminating immature glycans on GPIb receptors and Galβ epitopes on a variety of proteins. The present application provides knockout pigs and porcine organs, tissues and cells for transplantation into a human that do not express the indicated pig genome encoded products and methods of making and using the same. In an embodiment, the application provides a knockout pig comprising a disrupted ASGR1 gene, wherein expression of ASGR1 in the knockout pig is decreased as compared to a wild-type pig.

The word "identifying" is intended to encompass determining, ascertaining, finding, verifying, characterizing, categorizing, labeling, or indicating. The word "providing" is intended to encompass preparing, procuring, getting ready, making ready, supplying, or furnishing. It is recognized that methods of providing a cell may differ from methods of providing a subject and that methods of providing a liver may differ from methods of providing a pig.

Liver sinusoidal endothelial cells (LSECs) are endothelial cells obtained from the endothelium or endothelial lining of liver sinusoids. Liver sinusoidal endothelial cells are characterized by a fenestrae-forming ability, bristle-coated micropinocytotic vesicles, lysosome-like vacuoles in the perikaryon and low PECAM-1 levels. See Braet & Wisse, (2002) *Comparative Hepatology* 1:1, herein incorporated by reference in its entirety. Kupffer cells are large, phagocytic, stellate or pyramidal cells obtained from the lining of liver sinusoids. LSECs for use in the present methods may be isolated by any means known in the art. See Nedredal et al (2003) *Comparative Hepatology* 2:1, herein incorporated by reference in its entirety.

Platelets, also known as thrombocytes, are enucleate fragments of megakaryocytes involved in blood coagulation, hemostasis and blood thrombus formation. Human platelets are routinely isolated through a variety of methods including, but not limited to, platelet apheresis, plateletpheresis, and ultracentrifugation. Human platelet membranes are prepared from human platelets. Membranes are separated from the platelets and adhered to a substrate such as a polymer particle.

The phrase "platelet uptake" is intended to encompass the incorporation of a platelet into a liver or liver cell. While not being limited by mechanism, such uptake may occur through a phagocytic process. Platelet uptake may be monitored by any platelet uptake monitoring assay known in the art. Such assays include but are not limited to immunological methods, western blots, immunoblotting, microscopy, confocal microscopy, transmission electron microscopy, and phagosome isolation. It is recognized that the appropriate platelet uptake monitoring assay may depend upon the type of label used. Platelet uptake may be measured as percentage of total platelets absorbed, percentage of total platelets not absorbed, a ratio of absorbed to unabsorbed platelets, percentage of cells absorbing at least one platelet, percentage of cells not absorbing a platelet, or number of platelets absorbed per cell. Liver sinusoidal endothelial cell platelet uptake is the incorporation of at least one platelet into a LSEC. Kupffer cell platelet uptake is the incorporation of at least one platelet into a Kupffer cell. It is recognized that platelet uptake by more than one cell type may contribute to the total platelet uptake of the liver. Total platelet uptake by an animal liver may include platelet uptake by liver sinusoidal endothelial cells, platelet uptake by Kupffer cells, platelet uptake by LSECs and Kupffer cells, and platelet uptake by additional cell types. It is recognized that platelet uptake by different cell types may contribute similar or disparate fractions of the total platelet uptake by a liver. Thus an alteration, inhibition, reduction, decrease, or lowering of platelet uptake by a liver comprises an alteration, inhibition, reduction, decrease, or lowering of platelet uptake by one or more liver cell types. An alteration, inhibition, reduction, decrease, or lowering of platelet uptake may involve an alteration, inhibition, reduction, decrease or lowering of LSEC platelet uptake; an alteration, inhibition, reduction, decrease or lowering of Kupffer cell platelet uptake; inhibition, reduction, decrease or lowering of LSEC and Kupffer cell platelet uptake; and inhibition, reduction, decrease or lowering of a non-LSEC or Kupffer cell platelet uptake.

Phagocytosis is characterized by the formation of an endosome, which by the fusion of lysosomes containing degradative enzymes becomes a phagosome. While not being limited by mechanism, platelet uptake may occur through phagocytosis by LSEC and Kupffer cells.

The word "assaying" is intended to encompass measuring, quantifying, scoring, or detecting a particular biological activity. Methods of assaying biological activities are known in the art. It is recognized that a method of assaying one type of biological activity, such as a platelet binding, may not be suitable for assaying another type of biological activity, such as a cellular replication. It is recognized that methods of assaying a biological activity include direct measurements and indirect measurements. One skilled in the art would be able to select an appropriate method of assaying a particular biological activity. Methods of assaying platelet binding include but are not limited to, platelet clearance assays, platelet affinity binding, immunoassays, ELISAs, confocal microscopy, MALDITOF/TOF, and platelet uptake assays.

Expression of a gene product is decreased when total expression of the gene product is decreased, a gene product of an altered size is produced or when the gene product exhibits an altered functionality. Thus if a gene expresses a wild-type amount of product but the product has an altered enzymatic activity, altered size, altered cellular localization pattern, altered receptor-ligand binding or other altered activity, expression of that gene product is considered decreased. Expression may be analyzed by any means known in the art including, but not limited to, RT-PCR, Western blots, Northern blots, microarray analysis, immunoprecipitation, radiological assays, polypeptide purification, spectrophotometric analysis, Coomassie staining of acrylamide gels, ELISAs, 2-D gel electrophoresis, in situ hybridization, chemiluminescence, silver staining, enzymatic assays, ponceau S staining, multiplex RT-PCR, immunohistochemical assays, radioimmunoassay, colorimetric analysis, immunoradiometric assays, positron emission tomography, fluorometric assays, fluorescence activated cell sorter staining of permeabilized cells, radioimmunosorbent assays, real-time PCR, hybridization assays, sandwich immunoassays, flow cytometry, SAGE, differential amplification, or electronic analysis. See, for example, Ausubel et al, eds. (2002) Current Protocols in Molecular Biology, Wiley-Interscience, New York, New York; Coligan et al (2002) Current Protocols in Protein Science, Wiley-Interscience, New York, New York; Sun et al. (2001) *Gene Ther.* 8:1572-1579; de Jager et al. (2003). *Clin. & Diag. Lab. Immun.* 10:133-139; U.S. Pat. Nos. 6,489, 4555; 6,551,784; 6,607,879; 4,981,783; and 5,569,584; herein incorporated by reference in their entirety.

Expression may be analyzed directly or indirectly. Indirect expression analysis may include but is not limited to, analyzing levels of a product catalyzed by an enzyme to evaluate expression of the enzyme. See for example, Ausubel et al, eds (2013) Current Protocols in Molecular Biology, Wiley-Interscience, New York, N.Y. and Coligan et al (2013) Current Protocols in Protein Science, Wiley-Interscience New York, N.Y. Gene expression assays for porcine ASGR1 are commercially available (Applied Biosystems™, Carlsbad Calif.).

Any method of performing mass spectrometry (MS) known in the art may be utilized in embodiments of the methods. See for example McMaster 2005, LCMS a Practical User's Guide, Wiley Interscience; McMaster, 2008, GCMS a Practical User's Guide, Wiley Interscience; Ham, 2008 *Even Electron Mass Spectrometry with Biomolecule Applications*, Wiley Interscience, Eidhammer et al (2008) *Computational Methods for Mass Spectrometry Proteomics*, Wiley Interscience; herein incorporated by reference in their entirety.

Methods of identifying a liver sinusoidal endothelial cell platelet uptake modulating compound are provided. By LSEC platelet uptake modulating compound is intended an agent that modulates liver sinusoidal endothelial cell platelet uptake. Methods of identifying a Kupffer cell platelet uptake modulating agent are provided. By Kupffer cell platelet uptake modulating compound is intended an agent that modulates Kupffer cell platelet uptake. Modulation may be an increase or decrease in platelet uptake. A platelet uptake modulating agent will modulate platelet uptake by at least 1%, 5%, preferably 10%, 20%, more preferably 30%, 40%, 50%, 60%, yet more preferably 70%, 80%, 90%, or 100% as compared to an untreated or placebo treatment effect. The word "modulating" is intended to encompass changing, increasing or decreasing, altering, improving, ameliorating or reducing.

Compounds of interest include, but are not limited to, a nucleic acid molecule, a polypeptide, a peptide, a glycoprotein, a transcription factor, an antibody, a small molecule, a receptor inhibitor, asialofeutin, an antigenic fragment, siRNAs, short hairpin siRNAs, ASGR1 modulating agents, ASGR2 modulating agents, MAC1 modulating agents, siacylic acid, siacylic acid like compounds, siacylic acid modulating agents, calcium, chelating agents, monoclonal antibodies, polyclonal antibodies, Mac1 agonists, NPC-15669 (AnaSpec, Inc.), Mac1 antagonists, ASGR1 agonists, ASGR1 antagonists, ASGR2 agonists and ASGR2 antagonists. NPC-15669, an organic molecule, an N-FMOC leucine has been characterized as a Mac1 agonist and an anti-inflammatory molecule. See Noronha-Blob et al (1993) *J. Pharmacol Exp. Ther.* 267:664-669; Serebruany et al (1995) *J. Thromb. Thrombolysis* 1:171-178; and Serebruany et al (1999) *Life Sci* 65:1503-1513; herein incorporated by reference in their entirety.

Incubating two or more substances such as a compound of interest with a cell or a platelet or coated polymer particle with a cell is known in the art. Incubating may involve mild agitation, rocking, mixing, or rotating of the substances. One skilled in the art is capable of determining appropriate incubation durations which may range from 10 seconds to 1 minute; 1 minute to 10 minutes, 10 minutes to 1 hour, 1 hour to 2 hours, 2 hour to 4 hours, 4 hours to 24 hours, 24 hours to 48 hours, or more. The incubation temperature may vary; one skilled in the art is capable of determining suitable incubation temperatures. Further incubating two or more substances may involve providing additional components to improve, ameliorate or facilitate the desired outcome.

Cells such as platelets may be labeled, marked, tagged, or traced with a variety of labels. Biological labels suitable for platelets include, but are not limited to, radiolabels and fluorescent labels such as carboxyfluorescein diacetate succinimidyl ester (CFSE). See for example *The Handbook: A Guide to Fluorescent Probes and Labeling Technologies* $10^{th}$ Ed. (2005), herein incorporated by reference in its entirety.

Polymer particles useful for the methods are known in the art and include but are not limited to latex beads. See for example, Burlak et al (2006) *Molecular & Cellular Proteomics* 5:620-643, herein incorporated by reference in its entirety. By "coated" is intended that 10%, 15%, 20%, 25%, 30%, 35%, 40%, 45%, 50%, 55%, 60%, 65%, 70%, 75%, 80%, 85%, 90%, 95% or up to 100% of the surface area of the coated object, such as a polymer particle, is covered, contacted or connected with the coating component. It is recognized that concentration of the coating component may be evenly dispersed on the polymer particle or unevenly dispersed on the polymer particle.

"As compared to" is intended encompass comparing something to a similar but different thing, such as comparing a data point obtained from an experiment with a knockout pig to a data point obtained from a similar experiment with a wild-type pig. The word "comparing" is intended to encompass examining the character, qualities, values, quantities or ratios in order to discover resemblances or differences between that which is being compared. Comparing may reveal a significant difference in that which is being compared. By "significant difference" is intended a statistically significant difference in results obtained for multiple groups, such as the results for a first aliquot and a second aliquot. Generally, statistically significance is assessed by a statistical significance test such as but not limited to the student's t-test, Chi-square, one-tailed t-test, two-tailed t-test, ANOVA, Dunett's post hoc test, Fisher's test and z-test. A significant difference between the two results may be results with a $p<0.1$, $p<0.05$, $p<0.04$, $p<0.03$, $p<0.02$, or $p<0.01$ or greater.

The methods provided herein make use of an "aliquot", "sample", or "portion". The methods may make use of a first aliquot, second aliquot, third aliquot, fourth aliquot, fifth aliquot or more. Multiple aliquots of something are similar in composition, concentration, and volume.

Subjects suitable for use in the present methods are mammals including but not limited to human, bovine, canine, feline, equine, lapine, ovine, caprine, and simian mammals, particularly humans, baboons, monkeys, chimpanzees and dogs. Subjects at risk for an event or disorder include subjects exhibiting at least one symptom or attribute of such disorder, subjects with a family history of such a disorder, subjects with a medical condition or status for which a treatment increases the risk of an event or disorder and subjects with a history of a treatment that increases the risk of an event or disorder. Subjects at risk for thrombocytopenia may include subjects exhibiting a thrombocytopenia related disorder, subjects exhibiting a thrombocytopenia related symptom, subjects who have received exogenous platelets, subjects who are at risk for introduction of exogenous platelets, subjects who are recipients of exogenous platelets, subjects who are recipients of a liver transplant and subjects at risk for a liver transplant, particularly subjects at risk for a xenograft liver transplant. Subjects at risk for liver sinusoidal endothelial cell platelet uptake may include subjects with a disparity between liver type and platelet type, such a disparity may result from liver transplant, particularly a xenograft liver transplant, or exogenous platelet introduction; subjects exhibiting a thrombocytopenia related disorder, and subjects exhibiting a thrombocytopenia related symptom. Exogenous platelets are platelets not produced by the subject.

Thrombocytopenia is a quantity of platelets below the normal range of 140,000 to 440,000/µl. When thrombocytopenia occurs as a result of a medical or trauma-related condition other than transplant it may be treated by platelet transfusions or splenectomy. Thrombocytopenia related symptoms include, but are not limited to, internal hemorrhage, intracranial bleeding, hematuria, hematemesis, bleeding gums, abdominal distention, melena, prolonged menstruation, epistaxis, ecchymosis, petechiae, or purpura. Uptake of human platelets by pig livers contributes to the development of thrombocytopenia in xenograft recipients.

Pig cells express ASGR1 on liver sinusoidal endothelial cells; liver sinusoidal endothelial cells are involved with non-native platelet uptake and thrombocytopenia Thrombocytopenia related disorders include, but are not limited to, thrombocytopenia coagulopathy, alcohol-induced thrombocytopenia, thrombocytopenia in megaloblastic anemias, HIV-associated thrombocytopenia, idiopathic thrombocytopenic purpura, some myelodysplastic syndromes, cirrhosis, post-transfusion purpura, drug-induced thrombocytopenia, neonatal alloimmune thrombocytopenia, and Bernard-Soulier Syndrome.

Methods of identifying a thrombocytopenia modulating compound are provided. By thrombocytopenia modulating compound is intended is an agent that modulates thrombocytopenia. Modulation of thrombocytopenia may be an increase or decrease in platelet number, platelet concentration, rate of platelet loss, or percentage of platelet loss or other platelet related characteristic. A thrombocytopenia modulating agent will modulate thrombocytopenia by at least 1%, 5%, preferably 10%, 20%, more preferably 30%, 40%, 50%, 60%, yet more preferably 70%, 80%, 90%, or 100% as compared to an untreated or placebo treatment effect. A thrombocytopenia modulating compound may modulate one or more cells involved in platelet uptake.

The term "administering" is used in its broadest sense and includes any method of introducing a compound into a subject. This includes producing directly administering the compound and indirectly administering the compound. Indirect administration of the compound encompasses administering the compound to a liver or to platelets prior to or concomitant with introduction of the liver or platelets to the subject. Further examples of indirect administration include but are not limited to instances in which a medical professional may direct, advise, counsel, order, or instruct another member of the medical profession, a member of the medically related arts, an affiliate thereof, a subject, a subject's caretaker or a subject's care-provider to administer a compound to a subject. Methods of administering include, but are not limited to, intravenous, intramuscular, oral, intraperitoneal, transmucosal, and transdermal administration.

The phrase "platelet binding-related protein" is intended to encompass a protein occurring or originating on either a platelet or liver sinusoidal endothelial cell or Kupffer cell that is preferentially involved in the interaction between or binding of the platelet by the liver sinusoidal endothelial cell or the interaction between or binding of the platelet by the Kupffer cell, respectively. By the word "preferentially" involved is intended that the protein is found 5%, 10%, 15%, 20%, 25%, 30%, 35%, 40%, 45%, 50%, 55%, 60%, 65%, 70%, 75%, 80%, 85%, 90%, 95%, or 100% more frequently in the binding between a platelet and a LSEC than in the interaction between a LSEC and another cell type or the binding between a platelet and a Kupffer cell than in the interaction between a Kupffer cell and another cell type. A platelet binding related protein is a component of the platelet binding and platelet uptake process. Platelet binding proteins may occur in protein complexes comprising at least one protein of platelet origin and at least one protein of LSEC origin and protein complexes comprising at least one protein of platelet origin and at least one protein of Kupffer cell origin. A protein of platelet origin is a protein that is or was a component of the platelet. A protein of liver sinusoidal endothelial cell (LSEC) origin is or was a component of a LSEC. A protein of Kupffer cell origin is or was a component of a Kupffer cell. Platelet binding related proteins may include, but are not limited to, the asialoglycoprotein receptor, ASGR1 polypeptide, ASGR2 polypeptide, and Mac1 polypeptide.

Methods of analyzing proteins and protein complexes are known in the art and include, but are not limited to, mass-spectrometry (MS), HPLC, protein affinity, CD, immunoassays, ELISAs, peptide sequencing, affinity chromatograpy, 2-D gel electrophoresis, silver staining, SDS-polyacrylamide gel electrophoresis (SDS-PAGE), electron spray mass spectroscopy, NMR, sedimentation equilibrium, flow cytometry, tandem mass spectrometry, FRET, liquid crystal-MS (LC-MS), MALDI, MALDI-TOV, MALDI-MS, microassays, ion-exchange, reverse phase HPLC, peptide mass fingerprinting (PMF), 2-D DIGE, and microscale solution isoelectrofocusing (MicroSol IEF). Analyzing encompasses identification of the compound and may encompass determining or assessing the origin of the polypeptide such as but not limited to a protein of platelet origin and a protein of liver sinusoidal endothelial cell origin.

The word "isolated" is intended to encompass an entity that is physically separated from another entity or group. An isolated cell is physically separated from another group of cells. Examples of a group of cells include, but are not limited to, a developing cell mass, a cell culture, a cell line, a tissue, and an animal. The word "isolating" is intended to encompass physically separating an entity from another entity or group. Examples include physically separating a cell from other cells and physically separating a cell component from the remainder of the cell. An isolated cell or cell component is separated from 10%, 15%, 20%, 25%, 30%, 35%, 40%, 45%, 50%, 55%, 60%, 65%, 70%, 75%, 80%, 85%, 90%, 95%, 96%, 97%, 98%, 99%, up to 100% of other naturally occurring cells or cell components. Methods for isolating one or more cells from another group of cells are known in the art. See for example, Freshney (Ed) *Culture of Animal Cells*: a manual of basic techniques ($3^{rd}$ Ed) 1994, Wilely-Liss Inc; Spector et al (Eds) (1998) *Cells: a Laboratory Manual* (vol. I) Cold Spring Harbor Laboratory Press; and Darling et al (1994) *Animal Cells: culture and media*, John Wiley & Sons; herein incorporated by reference in their entirety. Methods of isolating a tissue or an organ from an animal are known in the art and vary depending on the tissue or organ to be isolated and the desired method of transplanting the tissue or organ.

A "skin related product" encompasses products isolated from skin and products intended for use with skin. Skin related products isolated from skin or other tissues may be modified before use with skin. Skin related products include but are not limited to replacement dressings, burn coverings, dermal products, replacement dermis, dermal fibroblasts, collagen, chondroitin, connective tissue, keratinocytes, cell-free xenodermis, cell-free pig dermis, composite skin substitutes and epidermis and temporary wound coverings. See for example Matou-Kovd et al (1994) *Ann Med Burn Club* 7:143, herein incorporated by reference in its entirety.

The attachment period of a skin related product is the time between application of the skin related product to a human subject and natural separation of the skin related product from the human subject. When a human subject's skin wound has sealed, a skin related product may be removed by natural separation or mechanical separation. However natural separation of a skin related product from a human subject may occur prematurely. Premature natural separation occurs before separation is desired by a medical practitioner. By way of example and not limitation, premature natural separation may occur before the wound has been sealed. Premature natural separation may also be termed "sloughing", "shedding", or "flaking". Clinical management of premature natural separation may include reapplication of a skin related product, dressing application, bandage application, administering antibiotic, and administering fluids. A skin wound may be sealed by any means known in the art including but not limited to by growth of the subject's skin and by skin grafting. Reduced premature separation encompasses a decreased, lower, less frequent, diminished, smaller amount of natural separation of a skin related product before separation is desired by a medical practitioner. The reduced premature separation may relate to a lower number of complete, a lower number of partial premature separation events, and involvement of a smaller portion of the skin related product in a partial premature separation event than compared to a skin related product obtained from a wild-type pig. A skin related product of the instant application may also exhibit an increased, lengthened, improved, extended, or expanded attachment period. Use of a skin related product of the instant application may increase the duration of the attachment period.

A skin wound encompasses any injury to the integument including but not limited to an open wound, burn, laceration, ulcer, leg ulcer, foot ulcer, melanoma removal, cancer removal, plastic surgery, and bite.

By "surgically attaching" is intended joining, combining, uniting, attaching, fastening, connecting, joining or associating through any surgical method known in the art.

The phrase "asialoglycoprotein receptor" is intended to encompass a polypeptide or polypeptide complex comprising one or more polypeptides encoded by a nucleotide sequence selected from the group comprising the ASGR1 gene (also known as the Ashwell receptor or the asialoglycoprotein receptor) and the ASGR2 gene. Methods of identifying an asialoglycoprotein receptor modulating compound are provided. The phrase "asialoglycoprotein receptor modulating compound" is intended to encompass a compound that modulates an asialoglycoprotein receptor activity such as but not limited to, ligand range, receptor-ligand affinity, asialoglycoprotein receptor concentration, and asialoglycoprotein expression level. An asialoglycoprotein receptor modulating compound will modulate an asialoglycoprotein receptor activity by at 1%, 5%, preferably 10%, 20%, more preferably 30%, 40%, 50%, 60%, yet more preferably 70%, 80%, 90%, or 100% as compared to an untreated or placebo treatment effect. Asialoglycoprotein receptor modulating compounds may include inhibitors such as, but not limited to, asialofeutin and siRNA.

The asialoglycoprotein receptor (Ashwell receptor, ASGR1) gene encodes a calcium dependent lectin involved with binding asialoglycoproteins. The asialoglycoprotein receptor is a calcium dependent lectin. Monoclonal and polyclonal anti-human asialoglycoprotein receptor antibodies are commercially available. Ligands for ASGR1 include, but are not limited to, galactose-β1,3(4)-n-acetyl glucosamine (Galβ1,4 NAc). Feutin has numerous galactose-β1,3(4)-n-acetyl glucosamine oligosaccharides covered by terminal sialic acids. Asialofeutin lacks the sialic acids that occur in feutin and has exposed carbohydrate epitopes.

An asialoglycoprotein receptor modulating compound alters the interaction between asialoglycoprotein receptor and a ligand. Such an alteration may increase or decrease any aspect of the asialoglycoprotein receptor ligand interaction such as but not limited to the binding efficiency, $k_D$, association, dissociation, or downstream activity of the receptor-ligand complex. The modulating compound may block, inhibit, decrease, lower, or prevent the receptor-ligand interaction.

Methods of modulating liver sinusoidal endothelial cell platelet uptake comprising providing a transgenic animal with an altered asialoglycoprotein receptor gene are provided. Transgenic animals are animals with a stably incorporated isolated nucleic acid molecule or a targeted disruption of a gene in the nuclear genome of at least one cell of the animal, preferably in the nuclear genome of some cells of the animal, more preferably in the nuclear genome of a plurality of the animal's cells, yet more preferably in the nuclear genome of a majority of the animal's cells. Methods of making various transgenic animals are known in the art. The phrase "disrupted gene" is intended to encompass insertion, interruption or deletion of a nucleotide sequence of interest wherein said disrupted gene either encodes a polypeptide having an altered amino acid sequence from the endogenous sequence, encodes a polypeptide having less amino acid residues than the endogenous amino acid sequence, or does not encode a polypeptide. A disrupted gene may be the gene of interest or a target site for introduction of a gene of interest modulating compound. Exemplary target sites include, but are not limited to, porcine Rosa26. Transgenic animals of interest include, but are not limited to, bovine, canine, feline, equine, lapine, ovine, caprine, and simian mammals. The term "porcine" as used herein can refer to any animal of the family Suidae. A porcine animal can refer to swine of any sort including, but not limited to, wild boar, domestic swine, miniswine, warthog, peccary and barboosa. For examples of miniswine see e.g., Bustand & McClellan, 1968 Lab Anim. Care. 18:280-287 and England and Panepinto, 1986, *Swine in Biomedical Research* Plenum Press NY pp 17-22; each of which is herein incorporated by reference in its entirety. A non-transgenic animal is a wild-type animal or animal with an unaltered nuclear genome. A transgenic animal of the present application exhibits reduced expression of the asialoglycoprotein receptor, reduced expression of ASGR1, reduced expression of ASGR2, reduced expression of MAC1, or expression of an ASGR1 polypeptide with an altered amino acid sequence.

Transgenic animals suitable for use in xenotransplantation and methods of producing mammals suitable for use in xenotransplantation are provided. Specifically, the present application describes the production of homozygous knockout pigs with decreased expression of asialoglycoprotein receptor (ASGR1). In embodiments of the present invention, pigs and porcine organs, tissues and cells therefrom are provided in which the ASGR1 gene is rendered inactive, such that the resultant ASGR1 products can no longer function. In an alternative embodiment the ASGR1 genes can be inactivated in such a way that no transcription of the gene occurs. In various embodiments multiple ASGR1 knockout pigs were made. Methods of making transgenic pigs, and the challenges thereto, are discussed in Galli et al 2010 *Xenotransplantation* 17(6) p. 397-410, herein incorporated by reference. Methods and cell cultures of the invention are further detailed below herein.

The term "knockout mammal" refers to a transgenic mammal wherein a given gene has been altered, removed or disrupted. It is to be emphasized that the term is to be intended to include all progeny generations. Thus, the founder animal and all F1, F2, F3 and so on progeny thereof are included, regardless of whether progeny were generated by somatic cell nuclear transfer (SCNT) from the founder animal or a progeny animal or by traditional reproductive methods. By "single knockout" is meant a transgenic mammal wherein one gene has been altered, removed or disrupted. By "double knockout" is meant a transgenic mammal wherein two genes have been altered, removed or disrupted. By "triple knockout" is meant a transgenic mammal wherein three genes have been altered, removed or disrupted. By "quadruple knockout" is meant a transgenic mammal wherein four genes have been altered, removed or disrupted.

In principle knockout animals may have one or both copies of the gene sequence of interest disrupted. In the case where only one copy or allele of the nucleic acid sequence of interest is disrupted, the knockout animal is termed a "heterozygous knockout animal". The term "null" mutation encompasses both instances in which the two copies of a nucleotide sequence of interest are disrupted differently but for which the disruptions overlap such that some genetic material has been removed from both alleles, and instances in which both alleles of the nucleotide sequence of interest share the same disruption.

The term "chimera", "mosaic" or "chimeric mammal" refers to a transgenic mammal with a knockout in some of its genome-containing cells.

The term "heterozygote" or "heterozygotic mammal" refers to a transgenic mammal with a disruption on one of a chromosome pair in all of its genome containing cells.

The term "homozygote" or "homozygotic mammal" refers to a transgenic mammal with a disruption on both members of a chromosome pair in all of its genome containing cells. A "homozygous alteration" refers to an alteration on both members of a chromosome pair.

A "non-human mammal" of the application includes mammals such as rodents, sheep, dogs, ovine such as sheep, bovine such as beef cattle and milk cows, and swine such as pigs and hogs. Although the application provides a typical non-human animal (pigs), other animals can similarly be genetically modified.

A "mutation" is a detectable change in the genetic material in the animal that is transmitted to the animal's progeny. A mutation is usually a change in one or more deoxyribonucleotides, such as, for example adding, inserting, deleting, inverting or substituting nucleotides.

By "pig" is intended any pig known to the art including, but not limited to, a wild pig, domestic pig, mini pigs, a *Sus scrofa* pig, a *Sus scrofa domesticus* pig, as well as in-bred pigs. Without limitation the pig can be selected from the group comprising Landrace, Yorkshire, Hampshire, Duroc, Chinese Meishan, Chester White, Berkshire Goettingen, Landrace/York/Chester White, Yucatan, Bama Xiang Zhu, Wuzhishan, Xi Shuang Banna and Pietrain pigs. Porcine organs, tissues or cells are organs, tissues, devitalized animal tissues, or cells from a pig.

The phrase "disrupted gene" is intended to encompass insertion, interruption, or deletion of a nucleotide sequence of interest wherein the disrupted gene either encodes a polypeptide having an altered amino acid sequence that differs from the amino acid sequence of the endogenous sequence, encodes a polypeptide having fewer amino acid residues than the endogenous amino acid sequence or does not encode a polypeptide although the nucleotide sequence of interest encodes a polypeptide.

The present specification provides a transgenic animal with reduced expression of functional ASGR1 genes. The animal can be any mammal suitable for xenotransplantation. In a specific embodiment, the animal is a pig.

Transgenic transplant material. Transplant material encompasses organs, tissue and/or cells from an animal for use as xenografts. Transplant material for use as xenografts may be isolated from transgenic animals with decreased expression of ASGR1 or from transgenic animals lacking ASGR1. Transgenic transplant material from knockout pigs can be isolated from a prenatal, neonatal, immature or fully mature animal. The transplant material may be used as temporary or permanent organ replacement for a human subject in need of an organ transplant. Any porcine organ can be used including, but not limited to, the brain, heart, lungs, eye, stomach, pancreas, kidneys, liver, intestines, uterus, bladder, skin, hair, nails, ears, glands, nose, mouth, lips, spleen, gums, teeth, tongue, salivary glands, tonsils, pharynx, esophagus, large intestine, small intestine, small bowel, rectum, anus, thyroid gland, *thymus* gland, bones, cartilage, tendons, ligaments, suprarenal capsule, skeletal muscles, smooth muscles, blood vessels, blood, spinal cord, trachea, ureters, urethra, hypothalamus, pituitary, pylorus, adrenal glands, ovaries, oviducts, uterus, vagina, mammary glands, testes, seminal vesicles, penis, lymph, lymph nodes and lymph vessels.

In another embodiment, the application provides non-human tissues that are useful for xenotransplantation. In various embodiments, the non-human tissue is porcine tissue rom a single knockout ASGR1−/− pig. Any porcine tissue can be used including but not limited to, epithelium, connective tissue, blood, bone, cartilage, muscle, nerve, adenoid, adipose, areolar, brown adipose, cancellous muscle, cartilaginous, cavernous, chondroid, chromaffin, dartoic, elastic, epithelial, fatty, fibrohyaline, fibrous, Gamgee, gelatinous, granulation, gut-associated lymphoid, skeletal muscle, Haller's vascular, indifferent, interstitial, investing, islet, lymphatic, lymphoid, mesenchymal, mesonephric, multilocular adipose, mucous connective, myeloid, nasion soft, nephrogenic, nodal, osteoid, osseus, osteogenic, retiform, periapical, reticular, smooth muscle, hard hemopoietic and subcutaneous tissue, devitalized animal tissues including heart valves, skin, and tendons, and vital porcine skin.

Another embodiment provides cells and cell lines from ASGR1 knockout animals. In one embodiment these cells or cell lines can be used for xenotransplantation. Cells from any porcine tissue or organ can be used including, but not limited to: epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, granulosa cells, cumulus cells, epidermal cells, endothelial cells, Islet of Langerhans cells, pancreatic insulin secreting cells, bone cells, bone precursor cells, neuronal stem cells, primordial stem cells, hepatocytes, aortic endothelial cells, microvascular endothelial cells, fibroblasts, liver stellate cells, aortic smooth muscle cells, cardiac myocytes, neurons, Kupferr cells, smooth muscle cells, Schwann cells, erythrocytes, platelets, neutrophils, lymphocytes, monocytes, eosinophils, basophils, adipocytes, chondrocytes, pancreatic islet cells, thyroid cells, parathyroid cells, parotid cells, glial cells, astrocytes, red blood cells, white blood cells, macrophages, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, dopaminergic cells, squamous epithelial cells, osteocytes, osteoblasts, osteoclasts, embryonic stem cells, fibroblasts and fetal fibroblasts.

Nonviable derivatives include tissues stripped of viable cells by enzymatic or chemical treatment these tissue derivatives can be further processed through crosslinking or other chemical treatments prior to use in transplantation. In a preferred embodiment, the derivatives include extracellular matrix derived from a variety of tissues, including skin, bone, urinary, bladder or organ submucosal tissues. In addition, tendons, joints, and bones stripped of viable tissue to including but not limited to heart valves and other nonviable tissues as medical devices are provided. In an embodiment, serum or medium suitable for cell culture and isolated from a knockout pig of the invention are provided. Components of porcine knockout organs, tissues or cells are also provided. Components may also be modified through any means known in the art including but not limited to crosslinking and aldehyde crosslinking. Components may vary depending on the larger organ or tissue from which the component is obtained. Skin components may include but are not limited to stripped skin, collagen, epithelial cells, fibroblasts and dermis. Bone components may include but are not limited to collagen and extracellular matrix. Heart components may include but are not limited to valves and valve tissue.

"Xenotransplantation" encompasses any procedure that involves the transplantation, implantation or infusion of cells, tissues or organs into a recipient subject from a different species. Xenotransplantation in which the recipient is a human is particularly envisioned. Thus xenotransplantation includes but is not limited to vascularized xenotransplant, partially vascularized xenotransplant, unvascularized xenotransplant, xenodressings, xenobandages, and xenostructures.

In embodiments, cell culture reagents isolated from a transgenic pig comprising a disrupted ASGR1 gene are provided. Cell culture reagents are reagents utilized for tissue culture, in vitro tissue culture, microfluidic tissue culture, cell culture or other means of growing isolated cells or cell lines. Cell culture reagents may include but are not limited to cell culture media, cell culture serum, a cell culture additive, a feeder cell, and an isolated cell capable of proliferation. By an "isolated cell capable of proliferation" is intended a cell isolated or partially isolated from other cell types or other cells wherein the cell is capable of proliferating, dividing or multiplying into at least one additional clonal cell.

In another embodiment, the invention provides a method of improving a hyperacute rejection related symptom in a patient comprising transplanting porcine organs, tissue or cells having reduced expression of ASGR1 on the porcine organs, tissue or cells into a human, wherein the hyperacute rejection related symptoms are improved as compared to when tissue from a wild-type swine is transplanted into a human. By "improving", "bettering", "ameliorating", "enhancing", and "helping" is intended advancing or making progress in what is desirable. It is also envisioned that improving a hyperacute rejection related symptom may encompass a decrease, lessening, or diminishing of an undesirable symptom. By "hyperacute rejection" we mean rejection of the transplanted material or tissue occurring or beginning within the first 24 hours post-transplant involving one or more mechanisms of rejection. Hyperacute rejection encompasses but is not limited to "acute humoral rejection" and "antibody mediated rejection".

"Hyperacute rejection related symptom" is intended to encompass any symptom known to the field as related to or caused by hyperacute rejection. It is recognized that hyperacute rejection related symptoms may vary depending upon the type of organ, tissue or cell that was transplanted. Hyperacute rejection related symptoms may include, but are not limited to, thrombotic occlusion, hemorrhage of the graft vasculature, neutrophil influx, ischemia, mottling, cyanosis, edema, organ failure, reduced organ function, necrosis, glomerular capillary thrombosis, lack of function, hemolysis, fever, clotting, decreased bile production, asthenia, hypotension, oliguria, coagulopathy, elevated serum aminotransferase levels, elevated alkaline phosphatase levels, jaundice, lethargy, acidosis and hyperbilirubenemia and thrombocytopenia.

Baboon and human platelet uptake by porcine LSEC occurs at similar rates.

In liver transplants, excessively large liver implants result in compartment syndrome resulting in primary graft non-function and recipient death.

The phrase "percent identity confidence" as related to a peptide or peptides is intended to encompass an overall score for each peptide derived from input from observed peptide MS/MS spectra and theoretically derived spectra from a protein database. In various embodiments an algorithm that generates a percent identity confidence overall score for each peptide utilizes additional predictors in generating the overall score. Methods of generating a percent identity confidence score are known in the art and include, but are not limited to, the Higgs Hale algorithm (Higgs et al (2005) *J. Proteome Res* 4:1442-1450); X!Tandem (Craig & Beavis, 2004 *Bioinformatics* 20:1466-1467) and SEQUEST (Eng et al 1994 *J. Am. Soc Mass Spectrom* 5:976-989).

siRNAs are double-stranded ribonucleic acid molecules 20-25 nucleotides in length and containing 5' phosphates and free 3'-hydroxyl groups that may include single-stranded overhangs on one or both ends of the siRNA that may be 1, 2, 3 or 4 nucleotides in length. siRNA may include a hairpin structure or may be a bimolecular species comprising separate sense and antisense strands. siRNA may include nucleotide analogs such as but not limited to thiophosphate and G-clamp nucleotide analogs; alternative base linkages such as but not limited to, phosphorothioate, phosphonoacetate and thiophosphonoacetate, and other modifications. Other modifications may include modifications useful for enhanced nuclease resistance, enhanced duplex stability, enhanced cellular uptake and cell targeting. The nucleotide sequences of the first and second strand of siRNAs are substantially complementary to each other. The nucleotide sequence of the first strand of siRNA is substantially identical to the target molecule. The phrase "substantially identical" with regard to nucleotide sequences pertains to the nitrogenous base rather than the sugar and is intended to encompass nucleotide sequences with a high degree of identity, sequences that are identical, or sequences that are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical. It is recognized that substantially identical RNA and DNA molecules encompass the substitution of the uracil for thymidine. The phrase "substantially complementary" with regard to nucleotide sequences is intended to encompass sequences that hybridize under moderately stringent conditions.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

siRNAs may be chemically synthesized and annealed before delivery to a cell or animal or they may be synthesized in vivo. In vivo synthesis may be from a plasmid expression system (Tuschl & Borkhardt, (2002) *Molec. Interventions* 2:158-167, herein incorporated by reference in its entirety. The siRNA may be used to test inhibition of a nucleotide sequence of interest in a cell, to alter expression of a nucleotide sequence of interest in a cell, to alter expression of the nucleotide sequence of interest in multiple cells of an organ, and to reduce liver sinusoidal endothelial cell platelet uptake. siRNA molecules may be delivered into cells in culture using methods known in the art including, but not limited to, electroporation, lipophilic reagents, transfection, magnetic methods and nanoparticles. siRNA may delivered into animals by various methods including, but not limited to, intravenous injection, direct injection into the target site, targeted delivery systems or in vivo synthesis from an isolated nucleic acid molecule maintained in the cell. An isolated nucleic acid molecule maintained in a cell may be incorporated into the nuclear genome.

The following examples are offered by way of illustration only and are not intended to limit the scope of the present invention in any way. Indeed various modifications in addition to those shown and described herein will become apparent to those skilled in the art from the foregoing description and the following examples and fall within the scope of the appended claims.

EXPERIMENTAL

Example 1

Porcine Liver Procurement

Livers were obtained from domestic or genetically modified pigs. Domestic pigs were predominantly of the Landrace breed and human blood group O positive. Genetically modified pigs included GTKO/hDAF pigs described elsewhere herein. Pigs were premed icated, intu bated and anesthetized with propofol and placed in the supine position. A midline incision to the abdomen was made. Ligamentous attachments to the liver were taken down. The portal vein and hepatic artery were cannulated and flushed with 2 liters of cold histidine-tryptophan-ketoglutarate solution (Essential Pharmaceuticals, LLC). Livers were removed from pigs and stored in histidine-tryptophan-ketoglutarate solution on ice at 4° C. until being placed on the liver perfusion circuit. Cold-ischemia time ranged from 45 minutes to three hours.

In certain experiments, porcine livers were obtained from abbatoirs. Porcine livers from abbatoirs were flushed with histidine-tryptophan-ketoglutarate solution containing heparin (2000U/L) within two minutes of exsanguinations.

Example 2

Platelet Preparation

For in vitro experiments, fresh whole human blood in anticoagulant citrate dextrose was centrifuged at 2000×g for 3 minutes. The platelet enriched supernatant was removed and centrifuged at 5000×g for 5 minutes. The platelet containing pellet was resuspended in phosphate buffered saline (PBS). Platelets were labeled with carboxyfluorescein succinimidyl ester (CFSE) (Invitrogen, Carlsbad Calif.) and counted using a hemocytometer.

Porcine platelets were isolated from fresh porcine blood in anticoagulant citrate dextrose in a manner similar to the human platelet isolation.

For ex vivo experiments, approximately $4 \times 10^{11}$ human platelets, less than 6 days from isolation and stored at 20 to 24° C. with gentle agitation were purchased as platelet-rich plasma from the Indiana Blood Center, Indianapolis, Ind., USA. For ex vivo liver perfusion, approximately $1 \times 10^{11}$ human platelets were washed two times in sterile phosphate-buffered saline (PBS) containing the anticoagulant citrate dextrose. Platelets were labeled with CFSE according to the manufacturer's protocol. Platelets were then counted with a hemocytometer. Porcine platelets were isolated from fresh porcine blood in anticoagulant citrate dextrose in a manner similar to the human platelet isolation.

Example 3

Liver Sinusoidal Endothelial Cell (LSEC) Isolation

Figure 7:
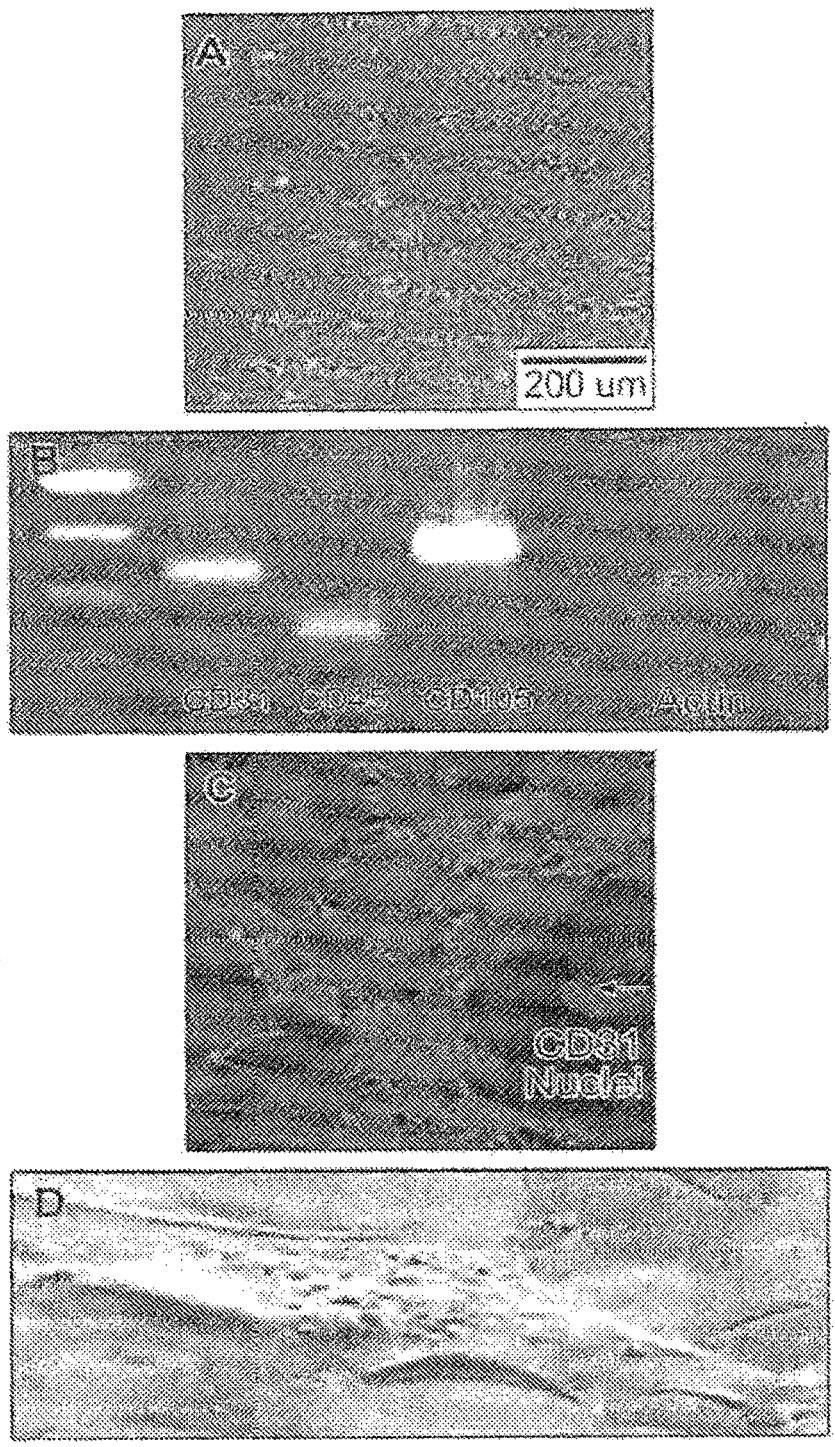
FIG. 7, panel A presents light microscopy of day 3 primary LSEC cultures. Panel B presents a gel with PCR products of markers for endothelial CD31 and CD105 and a marker for Kupffer cells, CD45. Actin is utilized as a control. Panel C presents confocal photomicrographs of day 4 LSEC cultures for CD31 and nuclei. Panel D presents scanning electron micrographs of day 4 LSEC cultures. Sieve plates, indicative of endothelial cells, are present.

Cold porcine livers were kept in a chilled container (4° C.). Livers were perfused with 0.025% of collagenase Type IV from *Clostridium histolyticum* (Sigma®, St. Louis, Mo.) at 37° C. The first 600 ml of perfusate was removed followed by continuous perfusion of the liver with collagenase at 37° C. for 20 minutes. Perfusion was interrupted for 30 minutes to allow removal of collagenase that had pooled around the liver. Perfusion was resumed at 10 ml/min with gentle manipulation of the liver. Digestion was stopped at 45 minutes or when fissures or soft spots were observed on the liver surface. At the end of perfusion, newborn calf serum was used to quench enzyme activity (1/10 volume). The perfusate was centrifuged at 400 g for ten minutes at room temperature. Supernatant was removed. The cell pellet was resuspended in RPMI+0.02% EDTA. The cell suspension was centrifuged at 400 g for 10 minutes at 4° C. The pellet was resuspended in LSEC culture medium (RPMI medium supplemented with 10% fetal bovine serum (v/v), 100 µg/ml endothelial cell specific growth factor, penicillin-streptomycin and amphotericin B). Cells were cultured on attachment factor (Invitrogen™, Carlsbad Calif.)-coated T150 culture flasks at a density of 20-50 million/flask. Medium was changed each day for two days. Cells were harvested for analysis on days 4, 5, or 6 after isolation or as indicated. A light micrograph of adherent porcine LSECs plated on collagen treated plates is shown in FIG. 7.

Example 4

Protein Identification & Glycosylation State Analysis
Method I: Immunoblot and Lectin Blot Assay LSECs were resuspended in Laemmli sample buffer with protease arrest (G-bioscience™, Maryland Heights Mo.). Samples were electrophoresed on SDS-polyacrylamide gels (SDS-PAGE). Polypeptides were transferred to membranes for immunoblot or lectin blot analysis. Membranes were blocked by incubation with 50% Odyssey blocking buffer (LI-COR Biosciences™, Lincoln Nebr.) in phosphate buffered saline (PBS) for approximately one hour. Membranes were incubated with anti-ASGR1 (Santa Cruz Biotechnologies™, Santa Cruz Calif.), anti-GAPDH (Millipore™, Billerica Mass., MAB374), anti-β-actin (Rockland Immunochemicals for Research, Gilbertsville Pa.), or anti-CD42b (Santa Cruz Biotechnologies™, SC-13467) according to the manufacturer's recommended protocol. Membranes were also incubated with ECA-biotin (EY Laboratories San Mateo Calif.) in a calcium containing buffer. Following primary antibody or lectin binding, membranes were washed. Membranes were incubated with the appropriate secondary antibody or streptavidin conjugated to either IRDye 800CW or IRDye680CW (LI-Cor Biosciences™). Membranes were washed and the blots were scanned with a LI-Cor near-infrared Odyssey scanner (LI-Cor Biosciences™). Protein bands were quantified by intensity using the LI-COR software. Results from one such experiment are presented in FIG. 14, panel B.

Example 5

GTKO/hDAF Transgenic Pigs

Somatic cell nuclear transfer methods are known in the art and refer to introducing a full complement of nuclear DNA from one cell to an enucleated cell. See for example Nagashima et al (1997) *Mol. Reprod Dev* 48:339-343; Nagashima et al (1992) *J. Reprod. Devel* 38:73-78; Prather et al (1989) *Biol Reprod.* 41:414-419; Prather et al (1990) *Exp. Zool* 255:355-358; Saito et al (1992) *Assis Reprod Tech Andro.* 259:257-266; and Terlouw et al (1992) *Theriogenology* 37:309; herein incorporated by reference in their entirety.

SCNT was performed using in vitro matured oocytes (Minitube of America, Mt Horeb Wis. and/or ART Madison Wis.). The oocytes were pippeted in 0.1% hyaluronidase to remove cumulus cells. Oocytes with normal morphology and a visible polar body were selected for cloning. Oocytes were enucleated by removing the first polar body and metaphase II plate.

Initial GTKO/hDAF fibroblasts (NSRRC 0009) for somatic cell nuclear transfer (SCNT) were obtained from the National Swine Research and Resource Center (NSRRC). GTKO/hDAF cells were cultured in DMEM medium supplemented with 15% fetal bovine serum (FBS) and harvested when confluent. Single cells were isolated and injected into each enucleated oocyte. Electrical fusion and activation was induced by electrical pulses as described in Estrada et al 2007 Cloning Stem Cells Summer 9(2):229-236, herein incorporated by reference in its entirety. After activation, embryos were transferred into a recipient at her first day of estrous. Homozygous GTKO/hDAF transgenic pigs were produced by SCNT; in some experiments GTKO/hDAF pigs were purchased after weaning from NSRRC. In at least one experimental group SCNT produced pig pregnancies at a 56% success rate. GTKO/hDAF piglets obtained from SCNT are shown in FIG. 12.

Example 6

Flow Cytometry

Formaldehyde fixed albumin conjugated to rhodamine (Sigma™, St. Louis Mo.) was incubated with LSECs for one hour at 37° C. prior to harvest. LSECs were harvested using lidocaine at 37° C. on day 4, 5 and 6 of culture as indicated. The cells were washed with PBS and 0.02% sodium azide, 0.5% bovine serum albumin (BSA) and stained with the following antibodies: anti-CD31 (R&D, Minneapolis Minn. AF3387), anti-CD105 (ABCAM AB53321 Cambridge Mass.), anti-CD45 (ABD Serotec MCA 1222F Raleigh N.C.), anti-ASGR1 (Santa Cruz Biotechnology SC-13467) and appropriate secondary antibodies and isotypes from Jackson Immuno Research (Westgrove Pa.). Data was collected with an Accuri C6 flow cytometer and analyzed with CFlow (Ann Arbor Mich.). Representative results are shown in FIG. 13, panel A.

Example 7

Pig Liver and Cell Pathology Analysis

Cells or CFSE-labeled platelets were incubated with formalin fixed albumin-TRITC (Sigma™, St. Louis Mo.) for 60 minutes at 37° C. Primary cells were fixed in 4% paraformaldehyde. Light microscopy was performed with an Olympus CX41 or CKX41. Confocal microscopy was performed with an Olympus IX81/FV1000 confocal microscope. For confocal analysis, cells were permeabilized with 0.2% Triton-X 100 and blocked with 1% BSA in PBS. Cell were incubated with anti-pig CD31 or anti-ASGR1 (Santa Cruz Biotechnologies) followed by secondary antibodies, bovine anti-goat IgG Dylight 549 (Jackson Immunoresearch Laboratories, West Grove Pa. #IR 805-505-180), donkey anti-mouse IgG Dylight 649 (Jackson Immunoresearch Laboratories, West Grove Pa., #IR 715-496+150), or donkey anti-rabbit IgG (H+L) Alexafluor 647 (Invitrogen™, Carlsbad Calif. #A-21091). Cells were mounted using Prolong Gold or Prolong Gold with DAPI (Invitrogen™, Carlsbad Calif.). Confocal microscopy images were captured using the settings of the negative control for a particular experiment. Images were uniformly cropped or adjusted in Photoshop CS4 software (Adobe™ San Jose Calif.). Representative images are presented in FIG. 14, panel D.

Example 8

Platelet Sequestration Analysis

A normothermic pig liver perfusion system was used. The perfusion system was computer controlled to maintain constant pressure by varying the flow rate. Centrifugal flow through the portal vein and pulsatile flow through the hepatic artery were used. Both flow rates were set at porcine physiological pressure. In ex vivo experiments, the base perfusion solution was an oxygenated Ringers solution with physiologic nutrition and insulin.

The pig livers were perfused for 2 hours prior to the addition of platelets. Duplicate samples of the platelets were obtained prior to addition to the perfusion system and after addition of the platelets at 15 minutes, 30 minutes, 45 minutes, 60 minutes, 75 minutes, 90 minutes, 105 minutes, 120 minutes, 135 minutes, 150 minutes, 165 minutes and 180 minutes. One sample from each time point was centrifuged and the platelets were counted. Duplicate samples from each time point were solubilized in detergent and separated by SDS-PAGE. The proteins were transferred to nitrocellulose membrane and subjected to immunoblotting. The membranes were incubated with antibodies to von Willebrand factor protein (vWF) to identify platelets and GAPDH as a control.

Figure 1:
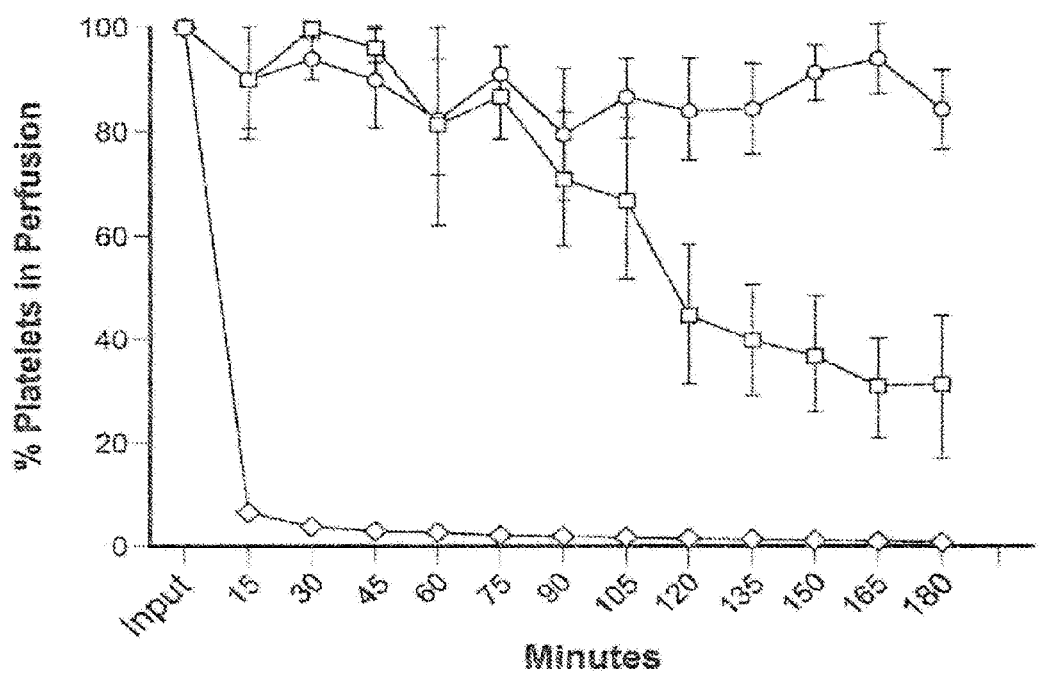
FIG. 1 presents a graph of data from ex vivo pig liver perfusion experiments. Human (squares) and pig (diamonds) platelets were added to a normothermic pig liver perfusion system as described elsewhere herein. Human platelets without a liver (circles) were used as a perfusion control. Time points are indicated on the x-axis and the percent of platelets in the perfusion solution are indicated on the y-axis. Pig platelets remain in circulation longer than human platelets. Human platelets added to the system without a liver show no significant decrease in platelet number. More than 90% of the human platelets perfused through the pig liver are removed from circulation in 15 minutes.
Figure 2:
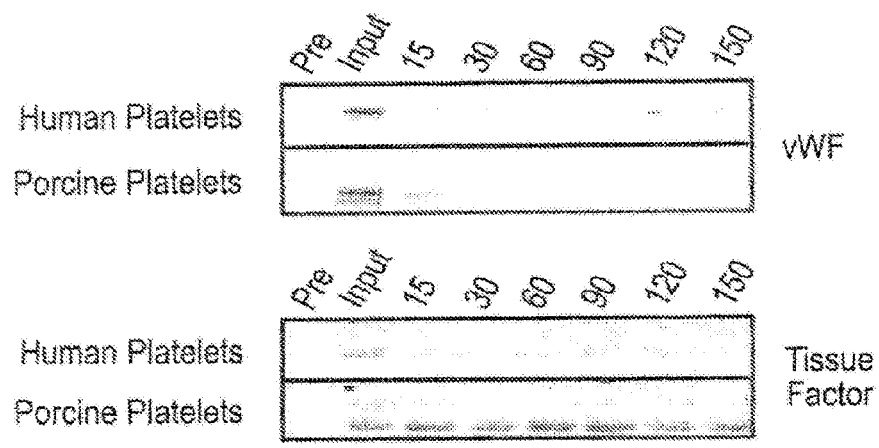
FIG. 2 presents data obtained from ex vivo pig liver perfusion experiments. Panel A and B present immunoblot results of platelet samples obtained at the indicated time points during ex vivo perfusion studies. Individual blots were quantified by density and plotted in panel C. Data from human platelets is indicated with diamonds, data from porcine platelets is indicated with squares. Human platelet Von Willebrand factor (vWF) decreased during the perfusion. Von Willebrand factor protein persists after platelet rupture but vWF protein levels in the sample decreased. Thus the reduction of von Willebrand factor protein indicates that the platelets are not lost to platelet lysis. These results indicate that platelets were removed by the liver.
Figure 2:
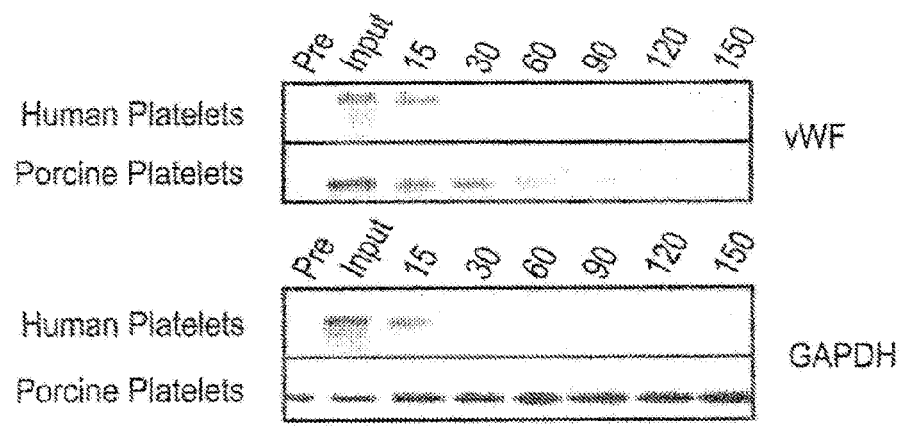
Figure 2:
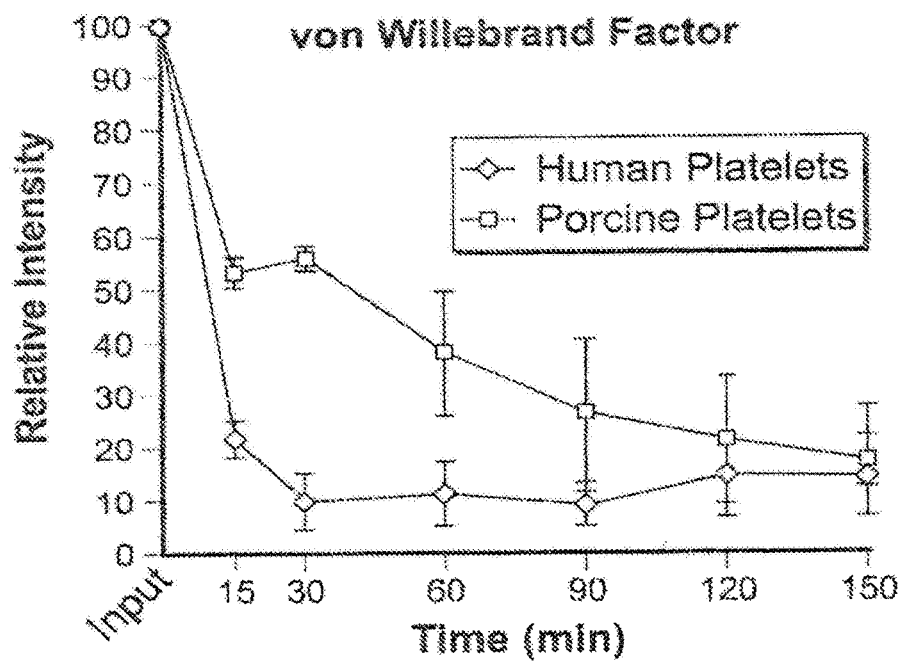
Figure 2:
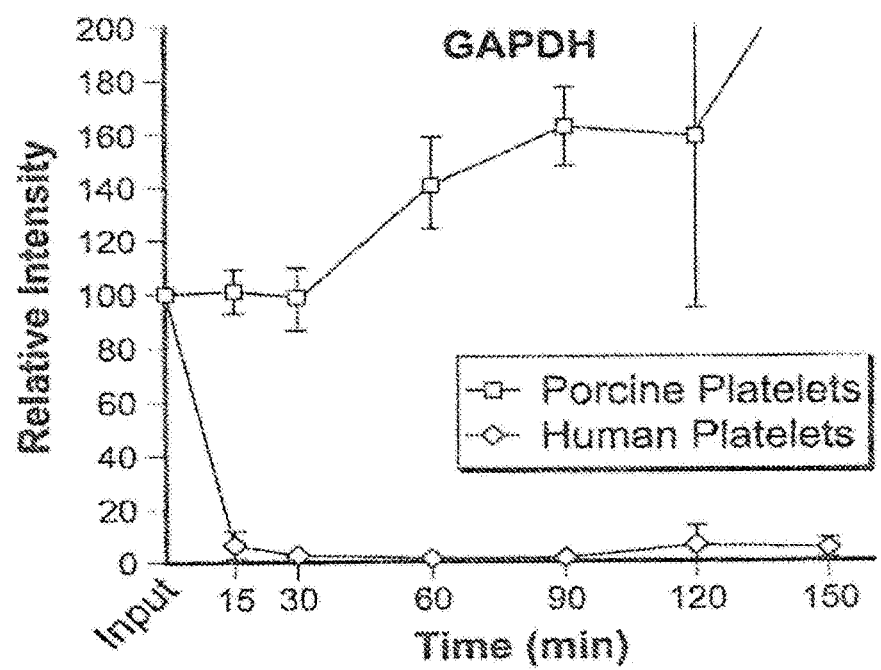

Fifteen minutes after the addition of platelets, greater than 90% of 300 billion human platelets were no longer in circulation. A control experiment involving the perfusion system without a pig liver showed no significant decrease in total platelet numbers. Data from one such experiment are presented in FIGS. 1 and 2.

Example 9

LSEC Platelet Sequestering I

Figure 4:
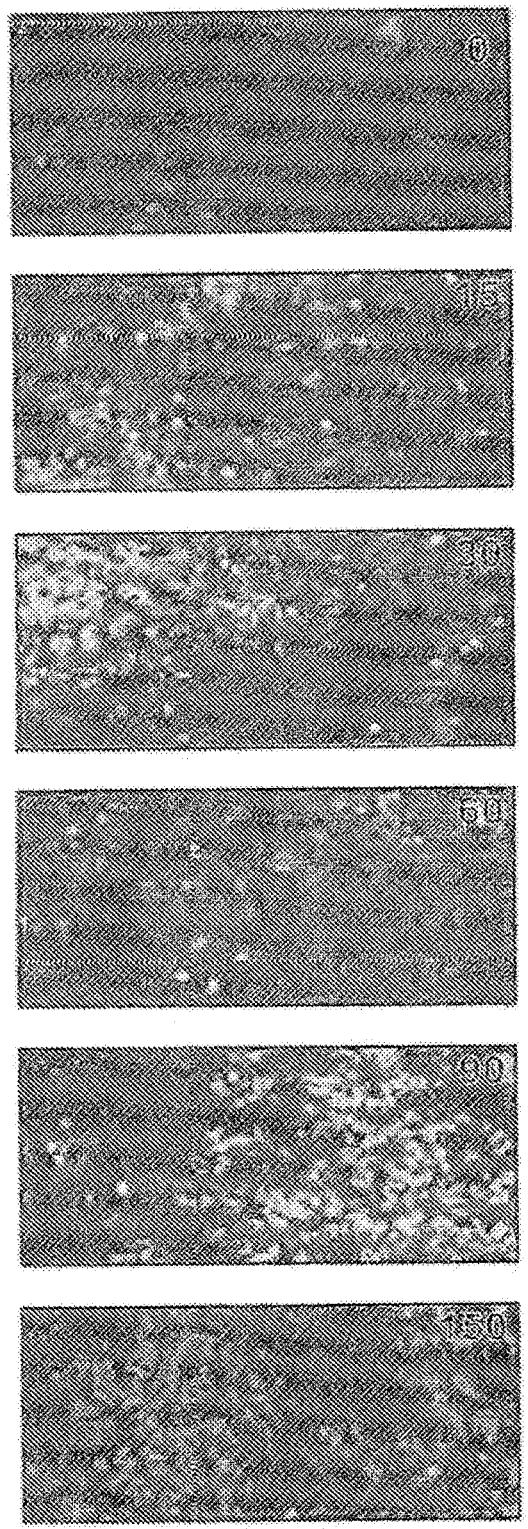
FIG. 4, panel A presents confocal images of biopsies obtained from the ex vivo perfusion system perfused with CFSE labeled human platelets at the indicated time points. Fluorescent intensity peaked at 15 minutes post platelet introduction and then decreased throughout perfusion. The fluorescent label became more diffuse in intracellular compartments. Panel B presents results obtained from a fluorescent ELISA based assay showing binding, phagocytosis, and degradation of human (squares) and baboon (triangles) platelets. Autofluorescence is indicated with circles.
Figure 4:
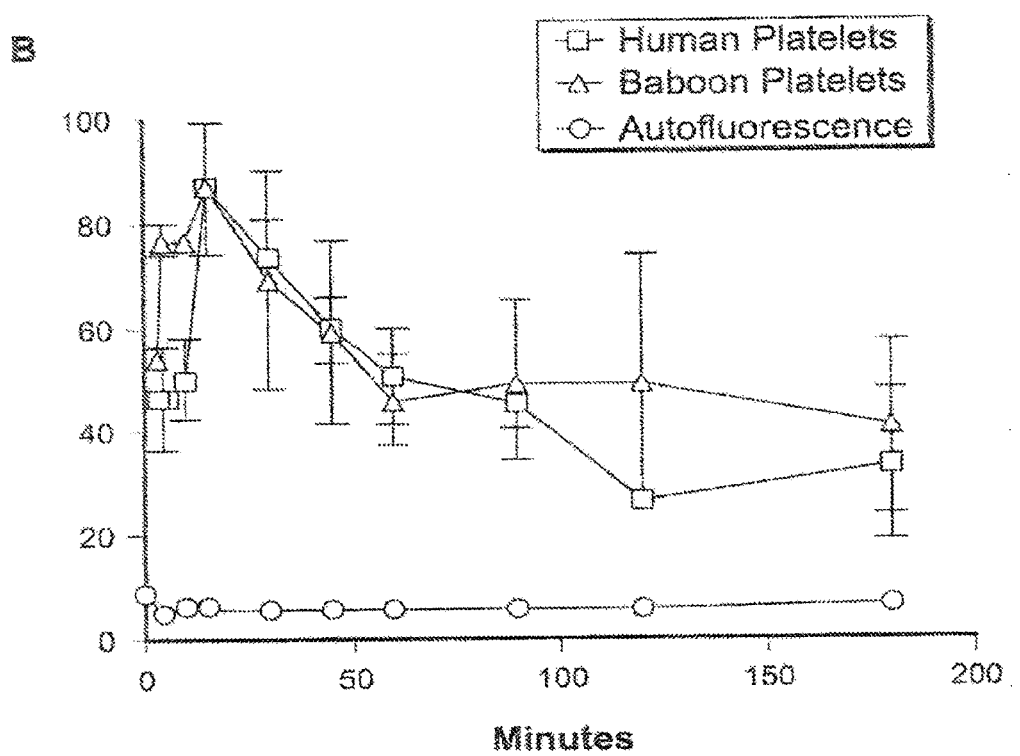

Platelets were labeled with carboxyfluorescein diacetate succinimidyl ester (CFSE), a fluorescent green cytoplasmic marker. A normothermic pig liver perfusion system was used. The pig livers were perfused for 2 hours prior to the addition of platelets. Approximately 300 billion platelets (unlabeled 70%, labeled 30%) were added to the perfusion system. Biopsies were taken from the pig livers at various time points including 15 minutes, 30, 60, 90 and 150 minutes. The biopsies were examined by confocal microscopy. The biopsy samples were also treated with a stain specific for Wieble-Palade bodies. Wieble-Palade bodies specifically occur in platelets and endothelial cells. CFSE stain may diffuse into the hepatocytes late in the perfusion process at approximately 120 and 150 minutes. Representative images are presented in FIG. 4.

Fluorescent ELISA based assays were performed also. Experiments were performed with human platelets or baboon platelets. Data obtained from multiple experiments are presented in FIG. 4.

Example 10

Phagocytosis of Platelets

Figure 5:
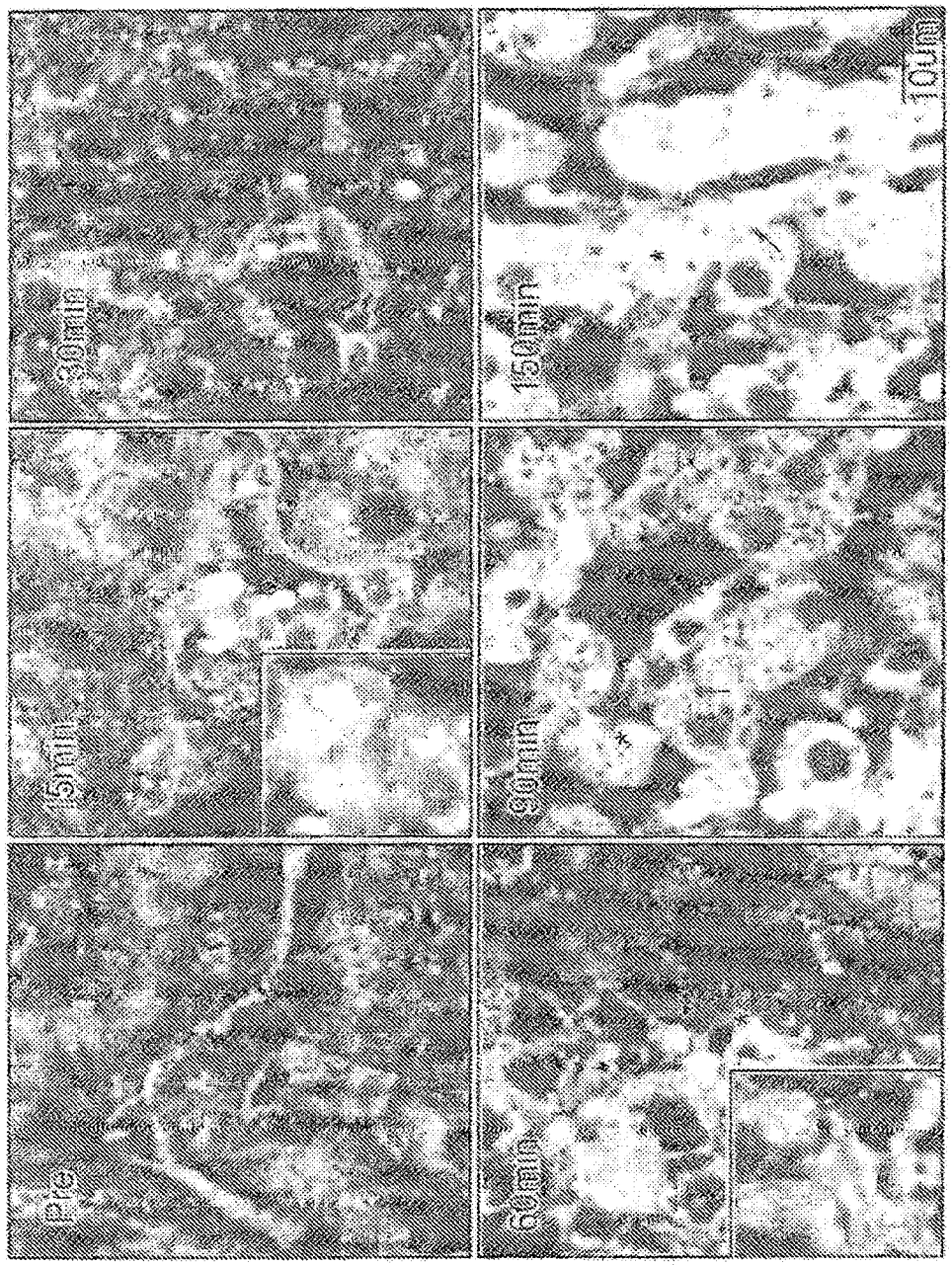
FIG. 5 presents confocal images of phagosome formation in ex vivo perfused pig livers. CFSE labeled human platelets were added to the pig liver perfusion system. Biopsies were taken at the indicated times and prepared for confocal microscopy analysis. Formation of early endosomes in sinusoidal cells is indicated with arrows with solid short arrowheads. Phagosomes are indicated with open short arrowheads. CFSE movement from human platelets to hepatocytes is indicated with asterisks. As shown, endothelial cells contain CFSE-labeled human platelets in developing phagosomes fusing with lysosomes. Large vacuoles in hepatocytes are present that contain platelet fragments, indicating a hepatocyte involvement in thrombocytopenia. Images are representative of multiple experiments.

Platelets were labeled with carboxyfluorescein diacetate succinimidyl ester (CFSE), a fluorescent green cytoplasmic marker. A normothermic pig liver perfusion system was used. The pig livers were perfused for 2 hours prior to the addition of platelets. Biopsies were taken from the pig livers at 15, 30, 60, 90 and 150 minutes. Tissue sections were labeled with endothelial markers and a lysosomal marker. In some experiments, lysosome associated membrane protein-1 (LAMP-1) localization was evaluated. The biopsies were examined by confocal microscopy. A common mechanism of phagocytosis forms phagosomes that are positive for a lysosomal marker. CFSE and the lysosomal marker co localized in phagosomes. Representative images are presented in FIG. 5.

Example 11

LSEC Platelet Sequestering II

Figure 6:
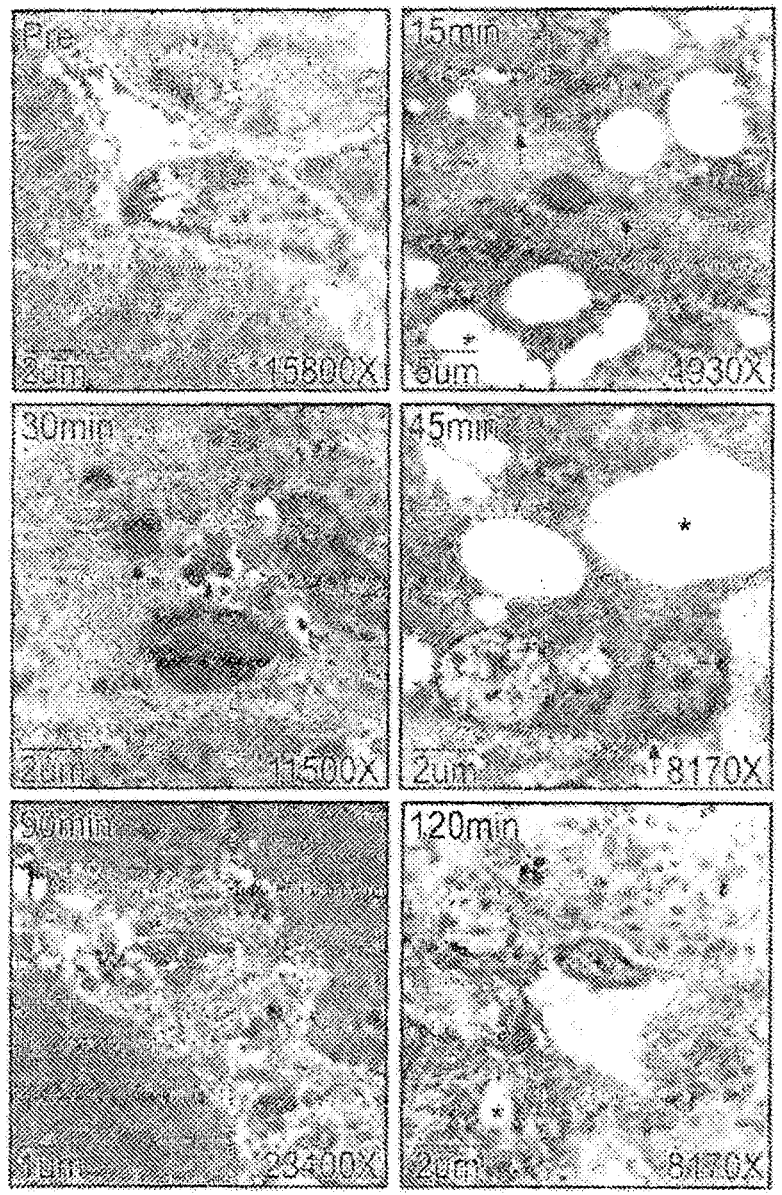
FIG. 6 presents transmission electron micrographs of biopsies of porcine liver after perfusion of human platelets in the ex vivo pig liver system. Biopsies were obtained at the indicated time (0, 15 minutes, 30 minutes, 45 minutes, 90 minutes and 120 minutes). Biopsies were fixed and prepared for TEM. Black arrows indicate bound or phagocytosed platelets. Large, fluid-filled vacuoles form early after the addition of human platelets and contain platelet debris but shrink and diminish by 90-120 minutes after platelet introduction (asterisks).

A normothermic pig liver perfusion system was used. The pig livers were perfused for 2 hours prior to the addition of platelets. Biopsies were taken from the pig livers at various time points (0, 15, 30, 45, 90 and 120). Biopsies were analyzed by transmission electron microscopy (TEM). TEM confirmed that LSECs bind and phagocytose platelets, beginning immediately upon addition of platelets to the system. Platelet binding and phagocytosis peaked around 15-30 minutes followed by a steady decay of fluorescence. TEM revealed that large vacuoles that contain platelet fragments form in hepatocytes. Clearly hepatocytes are involved in the formation of thrombocytopenia. Around 90 minutes and continuing through the 120 minute time point, the hepatocyte phagocytic vacuoles reduce and appear to expel the waste into the sinusoidal space. Representative images are presented in FIG. 6.

Example 12

Platelet Sequestering by Primary LSEC

Figure 8:
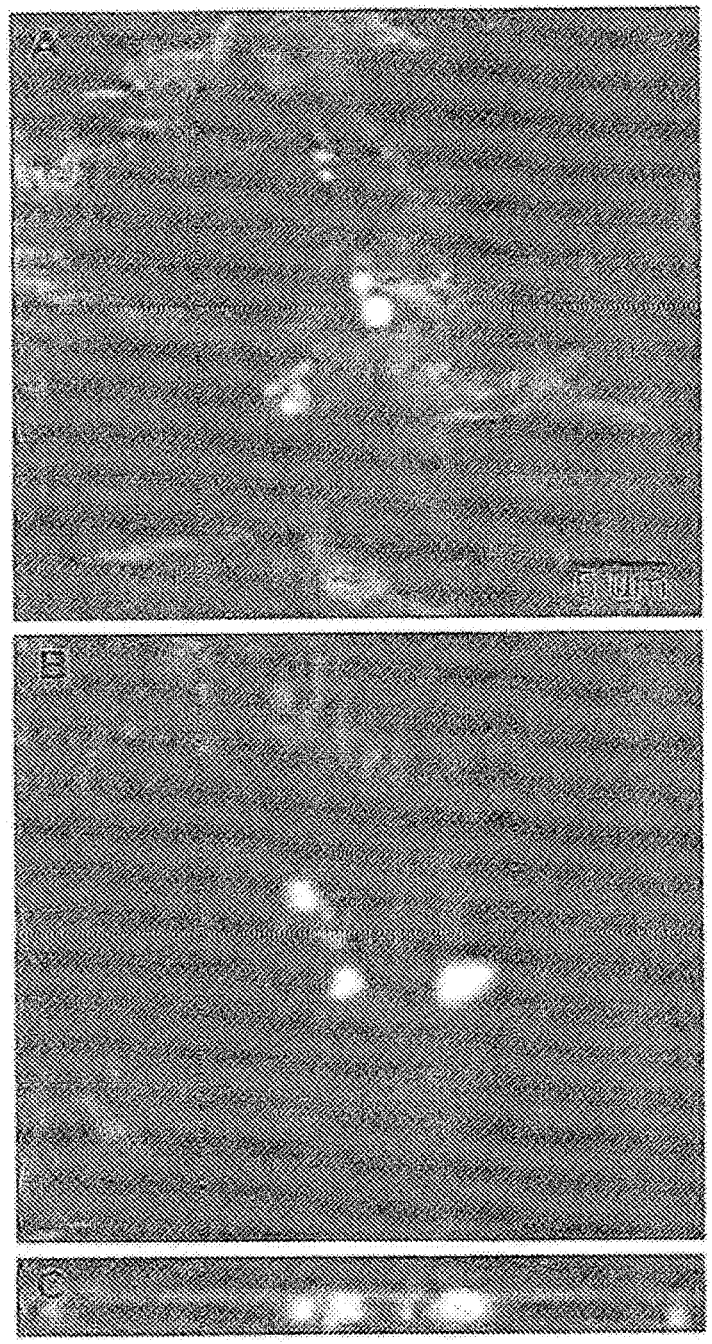
FIG. 8 provides results obtained from confocal microscopy of LSEC in vitro. Cells in Panel A are positive for CD31 and von Willebrand factor, a component of Wieble-Palade bodies.

Primary LSECs were isolated from the sinusoids of the pig liver. The primary LSECs loose phagocytic ability after 5 days in culture; these experiments were performed with day 3 and 4 primary LSECs. The isolated LSECs are positive for CD31 and von Willebrand factor (two endothelial cell markers) or Wieble-Palade bodies. Human platelets were labeled with CFSE as described above herein. Isolated LSECs and labeled human platelets were incubated together. The samples were analyzed by confocal microscopy. LSECs contained labeled human platelets. Further the lysosomal marker CD107a colocalizes with the CFSE labeled platelets. Representative images are presented in FIG. 8.

Example 13

In Vitro Platelet Binding Assay

Primary LSECs were cultured in black walled-clear bottomed, cell culture treated 96-well plates (approximately 100,000 cells/well). The plated cells were incubated at 37° C. and 5% $CO_2$ for four, five or six days as indicated. Four million CFSE-labeled platelets were added to wells in 96 well plates containing primary LSEC and media. Plates were centrifuged at 2000×g to synchronize the wells. At predetermined time points, the incubations were stopped. Duplicate wells for each time point were washed with PBS three times. After washing, the cells were incubated with 4% paraformaldehyde-PBS solution for 20 minutes to fix the cells. The wells were washed with PBS. 50 µl PBS was placed in each well. After obtaining the timepoints, the plates were read for fluorescence using a Spectra Max M2e plate reader (Molecular Devices Co.) set to read 9 different points within each well. Wells with LSECs and without CFSE-labeled platelets were used to determine the auto-fluorescence of LSECs. Data points from at least three separate porcine LSEC experiments were averaged and the standard deviation was obtained. Exemplary results are shown in FIG. 16, panel A.

Example 14

Sequestering of Coated Latex Beads by Primary LSEC

Latex beads were coated with human platelet membranes. Isolated day 3 or 4 LSECs positive for CD31 and vWF or Wieble-Palade bodies were incubated with coated latex beads. LSECs were lysed by nitrogen cavitation; phagosomes containing coated latex beads were separated from the LSEC by centrifugation in a Percoll gradient. Membranes and phagosomes were collected from the beads by ultracentrifugation.

Example 15

Xenotransplant-Induced Thrombocytopenia Analysis: Antibody Involvement

Pig IgG and IgM were incubated with human platelets. IgG and IgM binding to the platelets was evaluated by flow cytometry and by immunoblotting.

Two aliquots of primary porcine LSECs were provided. The first aliquot was incubated with human platelets alone. The second LSEC aliquot was incubated with Fc (an antibody blocking agent) and human platelets. Confocal microscopy was performed on the samples.

Figure 3:
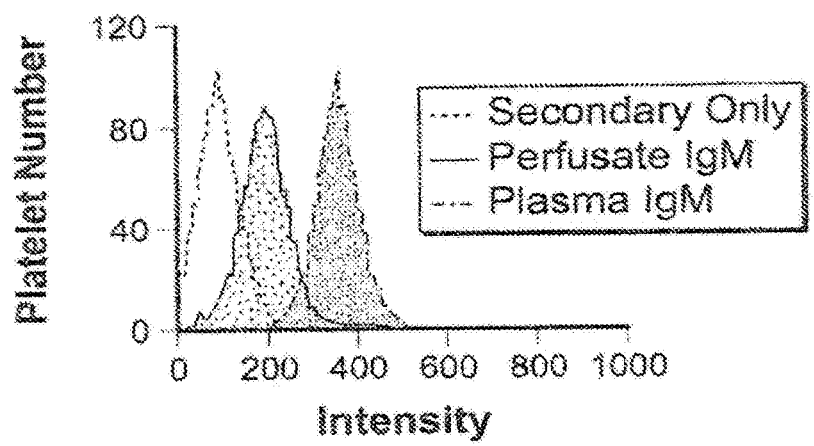
FIG. 3, panel A presents flow cytometry analysis and immunoblots of porcine IgG and IgM bound to platelets. Very small amounts of antibodies were detected on the platelets. Panel B presents confocal images of primary cultures of LSEC untreated (upper) and Fc blocked (lower) incubated with platelets. Panel C presents data obtained from experiments with increasing amounts of Fc (% FC Block, 0 contiguous line, 6.25% short dash-dot line, 12.5% long dash line, 25% short dash line, 50% dot line, 100% long dash-short dash line. Increasing Fc concentration had no significant impact on the results.
Figure 3:
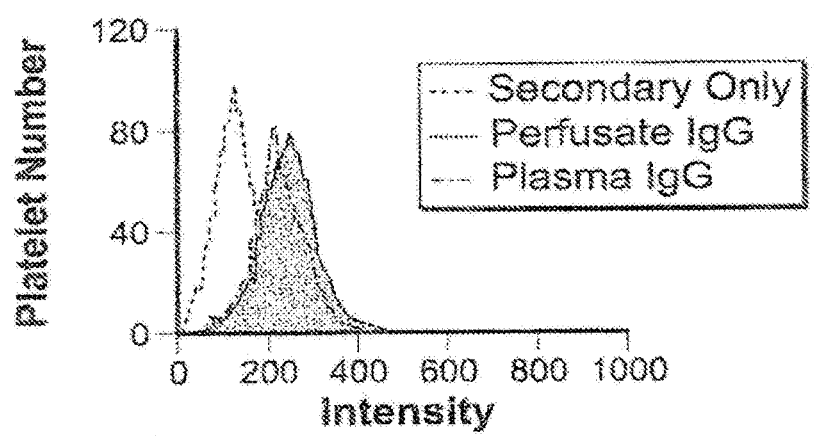
Figure 3:
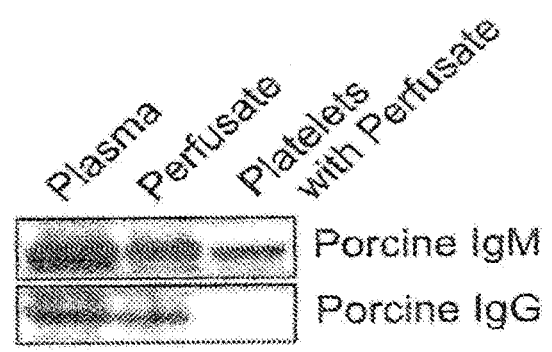
Figure 3:
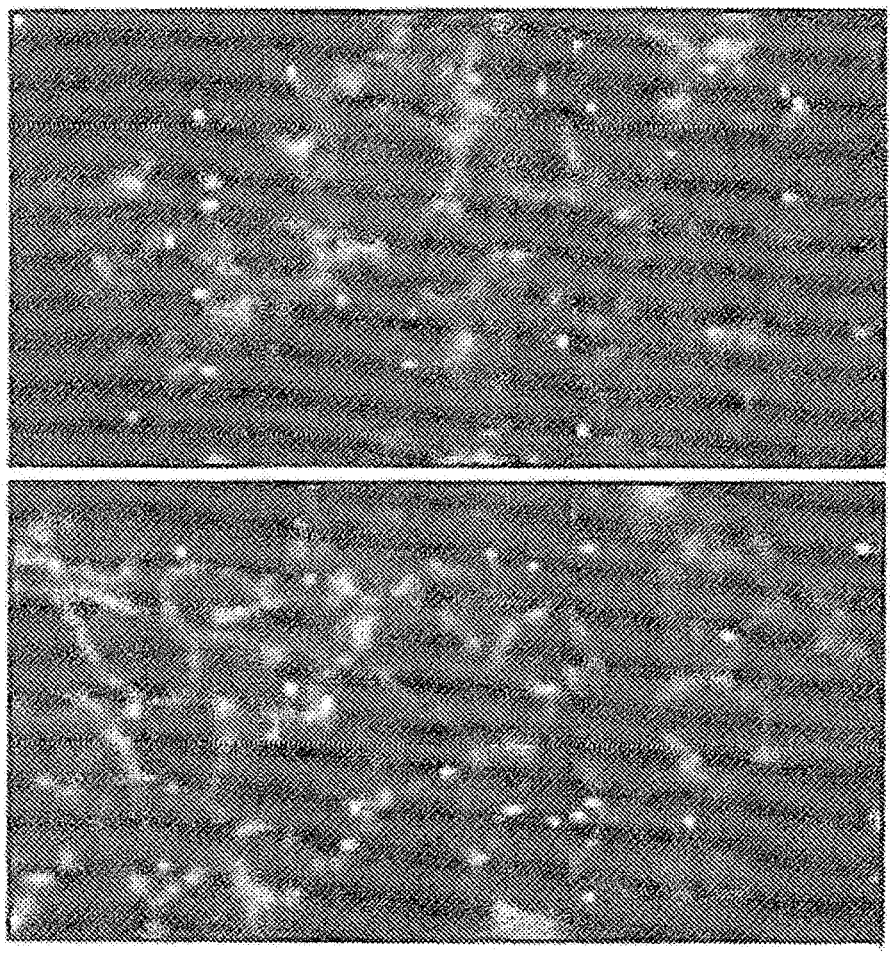
Figure 3:
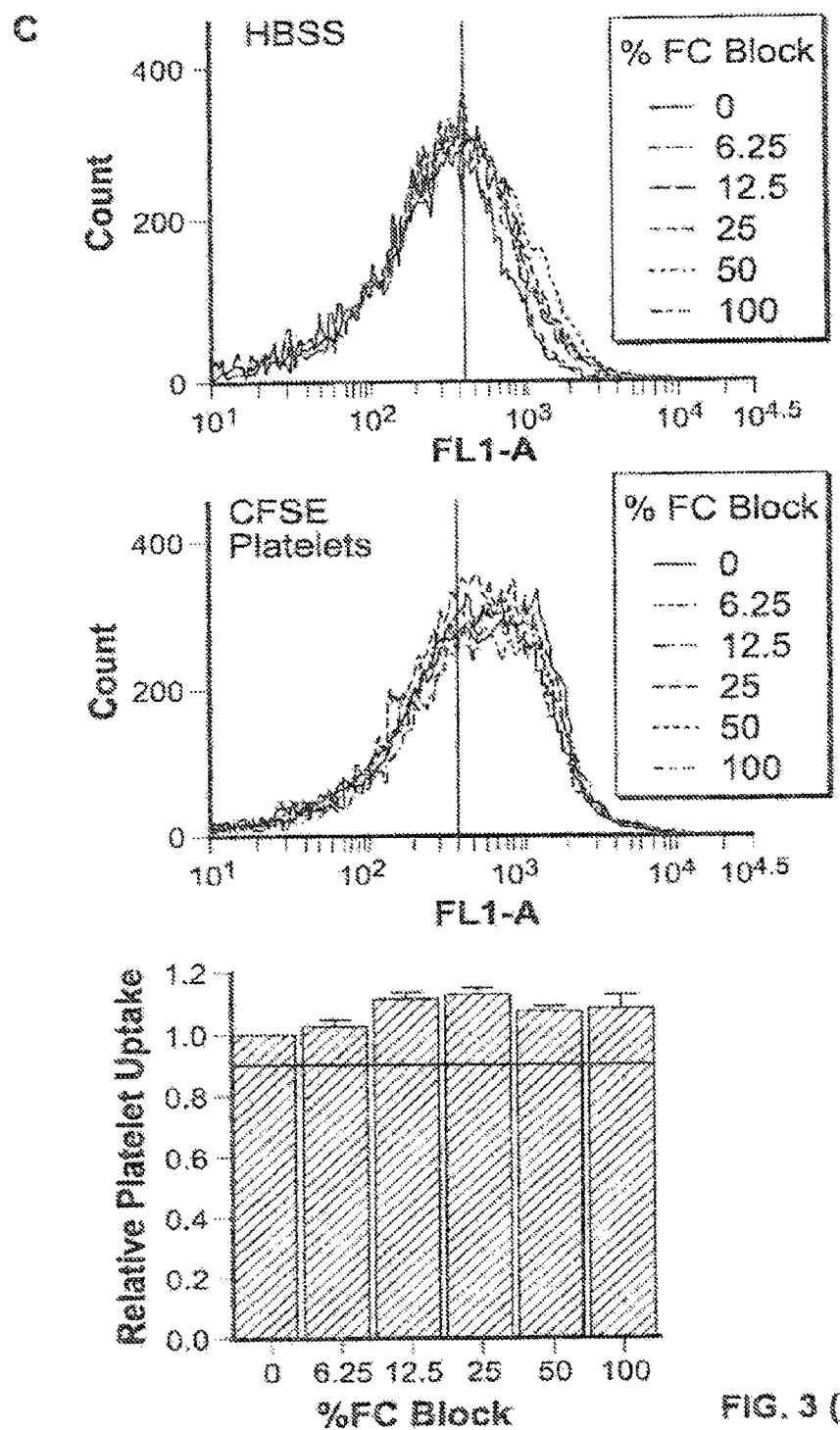

Increasing amounts of Fc were added to platelets in an ex vivo perfusion system. Platelet uptake was monitored. Representative images are presented in FIG. 3.

Example 16

Identification of a Platelet Binding Protein

After five days in culture, primary LSECs no longer bind human or baboon platelets. Gene expression analysis was performed on day 4 and day 5 LSEC and whole liver samples. Gene expression analysis indicated that ASGR1 expression was down-regulated or reduced in day 5 LSEC as compared to ASGR1 expression in day 4 LSECs or whole cell samples. Exemplary results are presented in FIG. 9.

Example 17

Quantitative PCR and Standard PCR

RNA extraction was performed on cultured LSEC and tissues harvested from domestic and GTKO/hDAF pigs. Total RNA was extracted from LSEC and low-fiber tissues using the RNeasy Minikit (Qiagen, Valencia Calif.). RNA from fiber-rich tissue was isolated using the RNeasy fibrous tissue kit (Qiagen, Valencia Calif.). RNA quality was assessed using an Agilent 2100 Bioanalyzer (Biotechnology Research and Training Center IUPUI). Reverse transcription was performed using Quantitect Reverse Transcription kit (Qiagen, Valencia Calif.). Presence/absence experiments of endogenous mRNA were performed on a 9700 Applied Biosystems™ cycler. Products were run using Quantitect Sybr Green (Qiagen, Valencia Calif.). Endogenous mRNA levels were measured by real-time quantitative PCR analysis on a STEP-ONE PLUS (Applied Biosystems™, Carlsbad Calif.) real time PCR system and comparative $C_T$ analysis was performed. Gene expression assays for porcine ASGR1 and β-actin AI6RMY and SSO 3376160-u1 (Applied Biosystems™, Carlsbad Calif.) were used. The primer sets for PCR were as follows: SEQ ID NO:1: ASGR1 forward GCGAG-CACAGACGCCAAGGT; SEQ ID NO:2 ASGR1 reverse GTGGGCACAGTCCTCGCCAC; SEQ ID NO:3: CD31 forward-ACCTGGTCACCGTGAGGGAA; SEQ ID NO:4: CD31 reverse:ATTTCCGGGAACGACTGGGC, SEQ ID NO:5: CD105 forward: ACCAGCTCTTCCTCTGGGCA, SEQ ID NO:6: CD105 reverse CATGTCCTTGCGGGGT-TCCA, SEQ ID NO:7: β-actin forward: TCCCTGGAGAA-GAGCTACGA; and SEQ ID NO:8: β-actin reverse: TGTTG-GCGTAGAGGTCCTTC.

Example 18

Computer Generated Structural Analysis of ASGR1

The human ASGR1 nucleotide sequence was used to identify the porcine ASGR1 sequence (SEQ ID NO:9) in the pig genome database (AK233544.1), gi 115554534. Porcine ASGR1 protein sequence was translated using SIB Expasy from the sequence AK233544.1 in the NCBI database. The porcine and human ASGR1 sequences were aligned and compared. Structural images were created using the Pymol Molecular Graphics System (DeLano, W. L. 2002 obtained on-line). Human ASGR1 binding domain (protein data bank: 1DV8) was superimposed with glunac (protein data bank: 1CBJ). The porcine ASGR1 binding domain was modeled by altering R262 to G262. The human ASGR1 Galβ binding site (SEQ ID NO:13) (Meier et al (2000), *J. Mol. Biol.* 300:857-865, herein incorporated by reference in its entirety) differs from the predicted porcine binding site by three amino acids. See for example FIG. 17B.

Example 19

High-Throughput Phagocytosis Assay

A high-throughput fluorescent 96-well phagocytosis assay was performed using human and baboon platelets and LSEC. The compounds of interest asialofeutin or feutin were added to the samples. Experiments were performed with reduced calcium or in the presence of the chelating agent, EDTA.

Example 20

Kupffer Cell Platelet Uptake Analysis

Biopsies of ex vivo perfusions were performed and prepared for Giemsa staining.

A hybridoma producing an anti-pig MAC1 antibody was grown in serum-free culture. The hybridoma produced a supernatant with approximately 8-9 µg/ml blocking antibody. A pig Mac-1 blocking antibody was perfused into the ex vivo liver perfusion system described elsewhere herein. Human or baboon platelets were perfused through the system. Biopsies were obtained and analyzed by confocal microscopy.

An enriched population of primary Kupffer cells was prepared. The primary Kupffer cells were incubated with baboon platelets and the Mac-1 blocking antibody. Confocal microscopy was performed.

Representative images are presented in FIG. 10. Macrophages lining the liver sinusoids bind platelets at early time points Example 21

Surgical Implantation of Pig to Baboon and Pig to Human Liver Xenotransplants

Pig livers are larger than baboon livers when comparing pigs and baboons of the same. Sizing comparisons were performed. Results from one such analysis are presented in FIG. 11.

The baboon has an intrahepatic retrohepatic vena cava making it difficult to perform a hepatectomy without interrupting the vena cava. Pig to baboon liver xenografts use the bicaval technique. Clinical pig liver xenografts into humans use the piggyback technique.

Example 22 siRNA Reduction of ASGR1 siRNA sense and antisense oligos were designed to the mRNA sequence of ASGR1 (FIG. 17C). SEQ ID NO:11 is the first strand of the siRNA (sense sequence); SEQ ID NO:12 is the second strand of the siRNA (antisense sequence) and complements the first strand having the nucleotide sequence set forth in SEQ ID NO:11. Purple Nimt FeOfection beads (15 µl 1×beads/ml) (Genovis, Sweden) were incubated with 60 pMol ASGR1 siRNA. ASGR1 siRNA-coated Purple Nimt FeOfection beads were incubated with one day old domestic porcine and GTKO/hDAF LSEC cultures for 30 minutes. siGenome non-specific sequences were transfected into LSECs as a negative control. The cells were washed and the media replaced. The cells were incubated for 48 hours before being harvested for analysis. Titrations of oligo and purple Nimt beads and time courses were performed in certain experiments. ASGR1 transcript levels were determined by quantitative PCR. ASGR1 protein levels were analyzed.

siRNA treated LSECs were used in the platelet phagocytosis assay described elsewhere herein. Exemplary results are presented in FIG. 17C.

Example 23

Evaluation of Galβ1,4 glcNAc Concentration on Platelets

Human, domestic porcine and GTKO/hDAF platelets were labeled with Erythrina cristagalli aglutinin (ECA)-PE. After lectin binding, ECA-PE labeled platelets were subjected to flow cytometry analysis. The mean fluorescent index (MFI) of human, domestic porcine and GTKO/hDAF platelets was determined. MFI results of ±standard deviation from triplicate experiments are presented in FIG. 18, panel A.

Example 24

Immunoblot/Lectin Blot Platelet Analysis

Human, domestic porcine and GTKO/hDAF platelets were lysed. The platelet lysates were subjected to immunoblots/lectin blot analysis using ECA, human CD42b, and GAPDH. Experiments were repeated in triplicate. Exemplary results are presented in FIG. 18, panel B.

Example 25

Platelet Desialation and Treatment

Human, domestic porcine and GTKO/hDAF platelets ($5 \times 10^8$/ml PBS) were incubated with 1/8 U sialadase A for 60 minutes at room temperature. Sialadase A removes terminal α2-3 and α2-6 sialic acid residues exposing Galβ epitopes. Cells were centrifuged. The supernatants were harvested and analyzed for sialic acid using the sialic acid quantification kit. Platelets were either labeled with CFSE and utilized in phagocytosis assays or evaluated by flow cytometry. N-glycolyl neuraminic acid, a common neuraminic acid in porcine cells but absent in humans, was measured using flow cytometry to analyze the sialadase treatment efficiency in porcine platelets. Representative results are presented in FIG. 18.

Example 26

LSEC Culture Evaluation: FFA Phagocytosis Assay

Domestic or GTKO/hDAF porcine primary LSEC cultures were established and maintained for four days. LSECs were incubated with fluorescently labeled FFA-TRITC for approximately 60 minutes. FFA-TRITC is preferentially phagocytosed by endothelial cells. Cells were examined for cell surface CD31 expression and FFA-TRITC uptake by flow cytometry. Representative images are shown in FIG. 13, panel A.

Domestic or GTKO/hDAF porcine primary LSEC cultures were established and grown for four days. LSECs were incubated with fluorescently labeled FFA-TRITC for approximately 60 minutes then probed for CD31 and stained with DAPI. Cells were analyzed by confocal microscopy at 600× magnification on the X/Y axis. Approximately 30 X/Y sections were stacked and deconvoluted to yield the Z-axis. Images representative of three experiments are shown in FIG. 13, panel B.

Example 27

Inhibition of Platelet Phagocytosis Assay

Fetuin, a glycoprotein composed of sialic acid terminated galactose β1, –4 N-acetylglucosamine (Galβ) oligosaccharides, and asialofetuin, a derivative of fetuin lacking the terminal sialic acid saccharides and with exposed Galβ oligosaccharides were utilized to evaluate platelet binding. Domestic (n=2-5) and GTKO/hDAF (n=5) LSEC cultures were established. Cultures were incubated with 0.5, 2.5, 5, 10 or 20 µg/ml fetuin or asialofetuin. After incubations, CFSE-labeled human platelets were added to the cultures. Platelet binding and phagocytosis was measured using a spectromax plate reader. The percent of platelet binding was calculated. Results from one such experiment are presented in FIG. 15.

Example 28

Inhibition of Platelet Phagocytosis Assay II: ASGR1 Involvement

Domestic and GTKO/hDAF LSEC cultures were established. Commercially available goat and rabbit polyclonal anti-ASGR1 antibodies and mouse monoclonal anti-ASGR1 antibodies were obtained. The mouse monoclonal anti-ASGR1 antibody preferentially bound ASGR1 and ASGR2. Anti-ASGR1 antibodies and species specific isotype controls were added to the LSEC cultures at 0.5, 1, 2, or 5 µg/ml. CFSE-labeled human platelets were added to the cultures. Platelet binding and phagocytosis was measured using a spectromax plate reader. Inhibition of platelet binding and phagocytosis by species specific isotype controls were utilized as background controls. The percent of platelet binding was calculated. Exemplary results are presented in FIG. 15. n=3.

Example 29

In Vivo Characterization of Thrombocytopenia

Pigs are anesthetized and blood is drawn. Pig tissues and organs are analyzed by quantitative PCR for porcine cytomegalovirus. Tissues and organs without porcine cytomegalovirus are utilized in the experiments.

Baboons have two venous and one arterial line inserted and are fitted with a jacket and tether for blood withdrawal and drug infusion.

Livers are surgically removed from α-galactosyltransferase knockout, human decay accelerating factor (GTKO/hDAF) transgenic pigs (n=4). Liver transplantation into baboons is performed using a bicaval technique. The portal vein and hepatic arteries are anastomosed in an end to end fashion. Donor and recipient bile ducts are anastomosed in an end to end fashion. Doppler ultrasound is performed perioperatively to assess hepatic arterial and portal venous anastomoses.

In non-survival experiments, the duration is 12 hours. Blood is drawn hourly for arterial blood gas, serum electrolytes, liver function panel, complete blood count and sonoclot analysis. Platelet counts and hematocrit analysis are performed hourly. Liver biopsies are performed hourly. The biopsy material is fixed in formalin and snap frozen.

In survival experiments, blood is drawn daily for arterial blood gas, serum electrolytes, liver function panel, complete blood count and sonoclot analysis. Liver biopsies are performed at reperfusion, 60 minutes post reperfusion and daily thereafter. Buprenorphine (0.01 mg/kg) is administered intravenously at 6-12 hourly for at least the first 72 hours after any major surgical procedure. Cefazolin (10 mg/kg, 2×/day) is administered intravenously (i.v.) for 48 hours after any surgical procedure. Blood cultures are drawn weekly. Transfusions of ABO-matched baboon red blood cells are given if the hematocrit falls below 20% or if hemoglobin falls below 8 g/d L.

When liver graft failure develops (lethargy, acidosis, hyperbilirubenemia), the baboon is anesthetized and the liver excised followed by exsanguination.

Example 30

Identification of a Thrombocytopenia Modulating Compound I

A compound of interest is administered to non-immunosuppressed baboons. In various experiments the compound of interest is an asialoglycoprotein receptor modulating compound such as, but not limited, to asialofeutin or siRNA. Asialofeutin inhibits the asialoglycoprotein receptor. The asialofeutin dose is determined from ex-vivo perfusion experiments described above herein.

Livers from GTKO/hDAF transgenic pigs (n=6) are transplanted into treated, non-immunosuppressed baboons. The first two transplants are non-survival studies as described above herein. Four transplants are survival studies as described above herein. A compound of interest that alters the thrombocytopenic course is identified as a thrombocytopenia modulating compound.

Example 31

Identification of a Thrombocytopenia Modulating Compound

Rituximab (150 mg/m$^2$) is administered to baboons to induce immunosuppression (Day –2). After one day (Day –1), an initial dose of thymoglobulin is administered i.v. (10 mg/kg). Thymoglobulin is administered on days 1 and 3 at a dosage to maintain the T cell count between 500-1000 cu·mm. Methylprednisolone is administered before each thymoglobulin dose and on the day of organ transplant (Day 0). Maintenance therapy is tacrolimus 0.05-0.1 mg/kg twice a day intramuscularly (i.m.) starting on Day 1 to maintain twelve hour trough levels of 10-15 ng/ml. All baboons receive levoflaxacin (10 mg/kg/day) and ganciclover (5 mg/kg/day) prophylactically and cimetidine (10 mg/kg×2 daily) to prevent peptic ulceration.

A compound of interest is administered to immunosuppressed baboons. In various experiments the compound of interest is an asialoglycoprotein receptor modulating compound such as, but not limited, to asialofeutin or a MAC1 modulating compound such as, but not limited to, NPC 15669. Asialofeutin inhibits the asialoglycoprotein receptor. The dose is determined from an ex-vivo perfusion experiment such as the perfusion experiments described above herein.

GTKO/hDAF transgenic pig livers (n=6) are transplanted into the immunosuppressed, treated baboons. Blood is drawn daily for arterial blood gas, serum electrolytes, liver function panel, complete blood count, and sonoclot analysis. Liver biopsies are performed at reperfusion, 60 minutes post-reperfusion and daily thereafter. Development of thrombocytopenia is evaluated. A compound that alters the thrombocytopenic course is identified as a thrombocytopenia modulating compound.

Example 32

Identification of a Platelet Binding Related Protein II

Latex beads are coated with human platelet membranes. Primary liver sinusoidal endothelia cells are prepared. Primary liver sinusoidal endothelial cells are harvested from one porcine liver for every phagocytosis experiment. Three experimental groups repeated five times each indicates livers are harvested from 15 pigs. Non-phagocytosing liver sinusoidal endothelial cells from a non-phagocytosing liver sinusoidal endothelial cell line developed by us are utilized.

LSECs phagocytose uncoated latex beads. Therefore the two control groups are LSECs not incubated with latex beads and non-phagocytosing LSECs. An aliquot of primary LSECs is incubated with latex beads coated with human platelet membrane. A second aliquot of primary LSECs is incubated under similar conditions in the absence of latex beads as a control. An aliquot of non-phagocytosing LSECs is incubated with latex beads coated with human platelet membrane. After the incubation, cells are lysed by nitrogen cavitation and phagosomes are isolated on a Percoll gradient. Millions of platelet membrane coated latex beads containing phagosomes are isolated per experiment. Membranes and proteins are stripped from the latex beads.

The membranes and proteins are analyzed by 1D or 2D polyacrylamide gel electrophoresis (PAGE). The 2-D PAGE gels are performed in replicates of 5 each, using high resolution electrophoretic equipment (Bio-Rad, Inc.) and a near infra-red scanner (Licor, Inc.). Protein spots unique to phagosomes containing platelet membranes are excised from the gel. Excised proteins are digested with trypsin. The tryptic fragments are subjected to mass spectrometry using an AB Sciex 5800 MALDITOF/TOF mass spectrometer. Comparisons of 2-D electrophoresis gels are challenging; therefore isolation of primary cells, control cell growth and sample preparation are synchronized so that simultaneous 2-D PAGE analysis may be performed. Mass spectrometry identified proteins are held to the criteria set forth in the HUPO proteomics standards initiative at the time the experiment is performed. The MOWSE score for each I.D. is assessed for statistical significance. The predicted molecular weight (M.W.) and isoelectric points identified proteins are compared with the observed position of the protein on the gel with replicates for consistency. Cell quality, protein quality, similarity of experimental controls and gel and MALDITOF/TOF resolution are assessed throughout the experiment. Gel images and statistical analysis of grouped samples and experimental samples are analyzed by PDQuest Advanced Software.

Example 33

Identification of a Platelet Binding Related Protein from a LSEC

Primary LSECs are isolated as described elsewhere herein. Primary LSECs, immortalized non-phagocytosing LSECs, and late passage (day 5 and beyond) non-phagocytosing primary LSECs are incubated with trypsin. Trypsin cleaves polypeptides at lysine and arginine residues. The tryptic fragments from the primary LSECs contain a platelet binding molecule from the LSEC surface. The tryptic fragments from the non-phagocytosing LSECs do not contain a platelet binding molecule. The tryptic fragments are collected. BioRad Pathfinder 20 liquid chromatography system is calibrated with BioRad standards. Tryptic fragments are separated by reverse phase liquid chromatography using the BioRad Pathfinder 20 liquid chromatography system, followed by in-line column desalting. The reverse phase media is a C18 end-capped media. The end-capping fills in the background media space as well as adds C3 and C4 carbon chains to the resin resulting in retention of weakly hydrophilic peptides. The fractions containing peptides are concentrated and prepared for MALDITOF/TOF analysis. The peptide mixture is analyzed by mass spectroscopy using an Ab Sciex 5800 mass spectrometry system calibrated by verifying and assigning know values to peptides from trypsin autolysis in the sample. Sample variance is further controlled by multiple replicates among the three groups of cells. Peptide lists of the average composition (n=3) of the peptides with the most frequently identified occurring first for primary LSECs, immortalized non-phagocytosing LSECs, and late passage non-phagocytosing primary LSECs are identified. Peptides that occur in one group but not in others or that are identified with a significantly different frequency will be analyzed further.

Example 34

Imaging of Platelet-LSEC Interaction

MALDI imaging is a technology where a laser is focused onto a tissue sample and excites cleaved peptides from the surface. The excited peptides are analyzed for their ID by the time of flight (TOF) stage of the MALDITOF/TOF. Protein ID data gathered from this analysis is recorded as "hits" at a specific location on a slide.

Livers are obtained from wild-type and GTKO transgenic pigs. Normothermic pig liver perfusion is performed as described elsewhere herein. Human platelets are introduced into the perfusion circuit. Biopsies are performed every 15 minutes to obtain samples for MALDI imaging analysis. Mirror sections are cut from the biopsy. One section is subjected to MALDI imaging and the other section to traditional histological staining. Histological staining is performed with hematoxylin and eosin. Replicate samples are analyzed. Statistical analysis is performed by the AB/Sciex Tissue View software and Protein Pilot 3.0.

Example 35

Laboratory Methods

ABO-blood typing in baboons is performed using the saliva or serum (previously adsorbed on human type 0 cells) and human A and B erythrocytes.

Flow cytometry for baboon T, B, and T cell subsets are performed by methods known in the art. Data is acquired using a FACScan fluorescence cytometer (Becton Dickinson) and analyzed using Winlist mode analysis software (Verity Software House, Topsham, Me.).

Pig anti-nonGal IgM and IgG binding to GTKO peripheral blood monocytes (PBMC) and aortic and inferior vena caval (IVC) ECs are monitored by flow cytometry. The median fluorescence intensity (MFI) is determined using FITC-conjugated goat anti-human IgM and IgG polyclonal antibodies.

Serum cytotoxicity to GTKO pig lymphocytes and aortic ECs is assayed by methods known in the art.

Mixed lymphocyte response (MLR) assay: In vitro cellular assays developed for investigation of the allo response in cynomolgus monkeys and of the human anti-pig xeno response have been described. These methods work with baboon cells as well. Briefly, for MLR cultures, baboon responder peripheral blood lymphocytes (PBL) are plated in triplicate in 96-well flat bottom plates at a final concentration of $4 \times 10^5$ cells/well. Stimulator pig PBL5 are irradiated (2500 cGY) and incubated with the baboon responder PBL5. Serum-free medium (AIM) is used for primate anti-pig MLR assays. Cultures are incubated for 5 days at 37° C. in 6% $CO^2$, 100% humidity. $^3$H-thymidine is added and the cells are incubated an additional 6 hours. Wells are harvested onto Betaplate fiber mats using a Tomtec 96 well harvester and counted for β-emission on an LKB Betaplate counter.

Liver biopsies are prepared for light microscopy (hematoxylin and eosin, periodic acid-Schiff) and for direct immunofluorescence (for IgM, IgG, C3, C5b-9, and fibrin). For conventional histology, tissues are fixed in 10% formalin and embedded in paraffin. Sections are cut to a 5 micron thickness and are stained. Immunohistochemical staining (for CD3, CD4, CD8, CD20, CD31, CD55, CD68, NK cells, TF, vWF, CD39, and CD63p (p-selectin)) is performed on paraffin and frozen sections. Electronmicroscopy is performed on glutaraldehyde-fixed tissues.

Baboon platelets were obtained as platelet rich plasma and used at a near physiological concentration in a 3-liter perfusion system.

Example 36

Platelet Binding Analysis

Non-phagocytosing, immortalized LSECs are transformed with an expression cassette comprising the ASGR1, ASGR2, or MAC1 gene nucleotide sequence with or without an epitope tag. Transcription and translation are verified. Protein products are confirmed with a Sciex/AB 5800 MALDITOF/TOF. Baboon platelet binding by the exogenous ASGR1, ASGR2, or MAC1 expressing immortalized LSECs is evaluated in the high-throughput assay.

Example 37 siRNA Inhibition of Platelet Binding

ASGR2 or MAC1 specific siRNA are designed using Sigma/Rosetta and the siRNA Design Algorithm-Mission siRNA software. siRNAs are delivered into cultured LSECs using N-TER nanoparticles.

Example 38

ASGR1 Antibody Formation

A ASGR1 peptide is produced using an extracellular epitope in the N-terminus bearing a limited number of glycosylation sites. The peptide is used as an antigenic fragment to obtain an antibody. New antibodies are screened for specificity, binding, and blocking ability by immunoblot, ELISA, platelet binding ELISA or confocal microscopy.

Example 39

Kupffer Cell Platelet Uptake Inhibition Analysis

An enriched population of primary Kupffer cells is prepared. A compound of interest such as NPC-15669 or an anti-Mac1 antibody is incubated with enriched Kupffer cells in vitro. The primary Kupffer cells are incubated with platelets. Platelet binding ELISA is performed.

Example 40

Liver Transplant into Baboon Recipients

*Papio hamadryas* baboons from an admixed population of *P.h. anubis* and *P.h. cynocephalus* are used in the studies. Baboons are moved from a group housing outdoor cage into a single cage. Health checks on the baboons are performed. Baboons are adapted to a sham tether system for 5 days prior to surgical implant of catheters for blood collection and drug administration. Subjects are euthanized when graft failure is confirmed.

Animals are assigned to one of six groups. Group 1 are normal baboons with GTKO/hDAF pig liver transplantation (12 hour non-survival surgery), group 2 are recipients with GTKO/hDAF livers treated with asialofeutin, group 3 are normal baboon recipients with GTKO/hDAF livers treated with asialofeutin and immunosuppression. Group 4 recipients receive a GTKO/hDAF liver and are treated with NPC-15669; Group 5 recipients receive a GTKO/hDAF and are treated with NPC-15669 and immunosuppression; Group 6 recipients receive GTKO/hDAF livers and are treated with asialofeutin, NPC-15669, and immunosuppression. Reperfusion biopsies are taken prior to skin closure. Animals remain intubated until recovered in an intensive care unit. Animals are returned to cages upon extubation. Blood samples are drawn every 8 hours for the first 24 hours then once daily thereafter.

Ten days after surgery animals are euthanized and recovered for histology. Animals with early graft failure are euthanized and subjected to a standard necroscopy protocol. Euthanasia is performed after the animal is immobilized with ketamine hydrochloride (10 mg/kg), intubated and moved to necroscopy. It is anesthetized with pentobarbital (25 mg/kg, IV) and exsanguinated.

Prior to and during surgery baboons are immobilized with ketamine (10 mg/kg, IM) and valium (5 mg, IV) and anesthetized with isoflurane (1.5% V/V inhalation). Analgesia is accomplished by morphine 0.1 mg/kg/hr drip.

Example 41

Porcine Care

Pigs are kept in same sex pairs in a custom large animal pen. Pigs undergo an initial health check and daily health monitoring. Pigs are tested for porcine cytomegalovirus. Pigs are socialized for two days prior to surgery or blood collection and administration of drugs. During surgery pigs are immobilized with ketamine (10 mg/kg, IM) and anesthetized with isoflurane (1.5% v/v inhalation) prior to and during surgery.

Euthanasia is performed after the animal is immobilized with ketamine hydrochloride (10 mg/kg), intubated and moved to necroscopy. It is anesthetized with pentobarbital (25 mg/kg, IV) and exsanguinated.

Example 42

DNA Sequencing Analysis of the Targeted ASGR1 Region

Genomic DNA from a cloned fetus and a cloned pig was extracted. PCR amplification of the ASGR1 region was performed. Primers were used to sequence the targeted ASGR1 regions.

Pwo Master (Roche, Indianapolis Ind.) was used, and PCR conditions were as follows: 94° C., 2 min; 94° C. 15 s, 57° C. 30 s, and 72° C. 30 s for 40 cycles; and a final extension step of 72° C. for 5 min. A total of 200-400 ng of PCR product was denatured and annealed using the following program on a Mycycler (BioRad): 95° C., 10 min; 95° C. to 85° C., −2° C./s; 85° C. to 25° C., −0.1° C./s. One microliter of enhancer and 1 µl of Nuclease S (Transgenomic Omaha Nebr.) was added to each reaction and incubated at 42° C. for 40 minutes. The product was separated on a 10% polyacrylamide gel and stained with SYBR Safe (Invitrogen USA Eugene Oreg.).

Results from an exemplary DNA sequence analysis are summarized in FIG. 19. DNA sequence analysis confirmed a homozygous alteration of the ASGR1 gene in at least one fetus and one pig. The ASGR1 gene is disrupted by a 26 base pair deletion; the nucleotide sequence of the deleted region is AGGTCTAGCCAGCCTTAGCATGACAA (SEQ ID NO:15).

Example 43

Production of Knockout Pigs

Somatic cell nuclear transfer (SCNT) was performed using in vitro matured oocytes (DeSoto Biosciences Inc., St. Seymour Tenn. and Minitube of America (Mount Horeb Wis.). Cumulus cells were removed from the oocytes by pipetting in 0.1% hyaluronidase. Oocytes with normal morphology and a visible polar body were selected and incubated in manipulation media (calcium-free NCSU-23 with 5% fetal bovine serum (FBS) containing 5 µg/ml bizbenzimide and 7.5 µg/ml cytochalasin B for 15 minutes. Following this incubation period, oocytes were enucleated by removing the first polar body and metaphase II plate. For the single knockout pigs, an ASGR1 single knockout cell line was established and then used in SCNT. Electrical fusion was induced with a BTX electroporator (Harvard Apparatus, Holliston Mass.). Enucleated oocytes injected with a cell (couples) were exposed to two DC pulses of 140 V fo 50 µs in 280 mM mannitol, 0.001 mM $CaCl_2$ and 0.05 mM $MgCl_2$. After activation the oocytes were placed in NCSU-23 medium with 0.4% bovine serum albumin (BSA) and incubated at 38.5° C., 5% $CO_2$ in a humidified atmosphere for less than one hour. Within an hour after activation, oocytes were transferred into a recipient pig. Recipient pigs were synchronized occidental pigs on their first day of estrus. Pregnancies were verified by ultrasound at day 25 or day 26 after embryo transfer. At least one experimental round with ASGR1 single knockouts yielded a single knockout fetus; fetal fibroblasts from a single knockout pig were used for SCNT to make pregnant pigs. One such pregnancy yielded 5 ASGR1 single knockout piglets.

All animals used in this study were approved by the Institutional Biosafety Committee (IBC) and Institutional Animal Care and Use Committee (IACUC).

Example 44

Ex Vivo Perfusion of Human Platelets Through Knockout Liver

A knockout ASGR1 pig was anesthetized and intubated. A midline abdominal incision was made. The liver was removed and placed in a perfusion device under normothermic conditions. Humidity, temperature and air flow were maintained in the perfusion device. Human platelets obtained from healthy volunteer subjects were circulated through the knockout liver. Platelet levels in the pre-perfusion and post-perfusion samples were evaluated. Pre and post-perfusion evaluation of the pig liver were performed. Wild-type pig livers were obtained, and the livers were perfused under similar conditions. Data from one experimental series are summarized in FIG. 20.

Example 45

Ex Vivo Perfusion of Human Platelets Through Knockout Liver

A knockout ASGR1 pig is anesthetized and intubated. A midline abdominal incision is made. The liver is removed and placed in a perfusion device under normothermic conditions. Humidity, temperature and air flow are maintained in the perfusion device. The perfusion device maintains constant pressure by varying the flow rate. Centrifugal flow through the portal vein and pulsatile flow through the hepatic artery are used. Both flow rates are set at porcine physiological pressure. The base perfusion solution is an oxygenated Ringers solution with physiologic nutrition nad insulin.

Human platelets are obtained from healthy volunteer subjects or purchased commercially less than six days from isolation and are stored at 20-24° C. Approximately $1 \times 10^{11}$ human platelets are washed in sterile phosphate buffered saline (PBS) containing the anticoagulant citrate dextrose. Platelets may be labeled with CFSE according to the manufacturer's protocol.

Pig livers are perfused two hours prior to the addition of platelets. Platelet samples are obtained prior to addition to the perfusion system and after the addition of the platelets at predetermined time points. Platelet levels in the pre-perfusion and post-perfusion samples are evaluated. Pre and post-perfusion evaluation of the pig liver are performed. Wild-type pig livers are obtained, and the livers are perfused under similar conditions.

Example 46

Evaluation of Response to a Knockout Xenograft

Porcine livers are obtained from a single knockout (ASGR1KO) pig. The livers are surgically transplanted into a recently deceased human cadaver using the piggyback method. After the surgery, biological samples are obtained from the human cadaver. Clinical indicia of a rejection related response are monitored.

Example 47

Evaluation of Response to a Knockout Xenograft

Porcine kidneys are obtained from a single knockout (ASGR1KO) pig. A highly sensitized human subject is administered compounds to manage preexisting and de novo donor-specific antibodies. The porcine kidneys are surgically transplanted into the subject. After the surgery, biological samples are obtained from the human cadaver. Clinical indicia of a graft rejection are monitored.

Example 48

Flow Cytometry of Red Blood Cells (RBCs)

Fetal livers are removed from porcine knockout fetuses and incubated in RPMI1640 for 24 hours at 37° C. RBCS are collected from cells released into the media after incubation of the fetal livers. RBC's are also obtained from adult human donors, six month old wild-type pigs and other pigs of interest (fetal or six month old). Porcine and human peripheral blood monocytes (PBMCs) are prepared using Ficoll-Paque Plus from whole blood collected in anticoagulant citrate dextrose (ACD).

Cells are stained with anti-ASGR1 antibodies. A negative control antibody for comparison is also used (Sialix Vista Calif.). Cells stained with anti-ASGR1 antibody are washed before and after secondary antibody with blocking agent diluted in PBS. Unstained RBC or PBMC may be used as negative controls. An Accuri C6 flow cytometer and CFlow Software (Accuri, Ann Arbor Mich.) are used for analysis.

Example 49

Confocal Microscopy Analysis

Piglets (single ASGR1 knockouts, wild type or other piglets of interest) are euthanized. Liver, heart and kidney tissue are obtained from the pig. Frozen sections of each tissue are prepared. Mounted tissues are blocked in Odyssey blocking buffer (Li-Cor Biosciences, Lincoln Nebr.) in HBSS for one hour. The slides are fixed in 4% paraformaldehyde for 10 minutes. To visualize ASGR1, tissues are stained with an ASGR1 antibody or with a control antibody for an hour. Tissues are washed three times with HBSS. Secondary antibody is incubated with the tissue for approximately an hour. Tissues are washed three times with 0.1% HBSS Tween. To stain the nucleus, DAPI stain (Invitrogen, Grand Island N.Y.) is added to all the slides for 1 minute followed by two 0.1% HBSS Tween washes. Tissues are mounted in ProLong Gold (Invitrogen, Grand Island N.Y.). Confocal microscopy is performed using an Olympus FV1000.

Example 50

Crossmatch of Human Sera with Knockout PBMCs

Porcine whole blood from knockout (single ASGR1) and wild-type pigs are collected in ACD. Porcine peripheral blood monocytes (PBMCs) are prepared from the whole blood using Ficoll-Paque Plus. Cell viability is assessed microscopically with Trypan Blue. Sera are obtained from healthy human volunteers. Twenty-five percent heat inactivated serum is prepared. Approximately $2\times10^6$/ml porcine PBMCs are incubated with each human serum sample for two hours at 4° C. After incubation of the serum and PBMCs, the PBMCs are washed three times in 0.5% PBS Sialix Blocking agent. PBMCs are stained with DyLight 649-conjugated donkey anti-human IgM or DyLight 488 donkey anti-human IgG (Jackson Immunoresearch Laboratories Inc., West Grove Pa.) for 1 hour at 4° C. PBMCs are washed three times using 0.5% PBS Sialix blocking agent. Analyses are performed using an Accuri C6 flow cytometer and BD CFlow Plus Software (Accuri, Ann Arbor Mich.). Overlays are produced using Kaluza software from Beckman Coulter (Brea Calif.).

Example 51

Antibody-Mediated Complement-Dependent Cytotoxicity

Antibody-mediated complement dependent cytotoxic assays are known in the art. A method of Diaz et al (Diaz et al., 2004 *Transplant Immunology* 13(4):313-317) is performed. Human serum is obtained from healthy volunteers. Twenty-five percent heat inactivated serum is prepared. Heat-inactivated human sera are serially diluted and 100 µl of each concentration is placed in a 96 well v-bottom assay plate. The sera is mixed with a 100 µl aliquot of PBMC obtained from a pig of interest (ASGR1 single or other). PBMC final concentrations are either $5\times10^6$/ml or $1\times10^6$/ml. Serum concentrations vary from 50%, 17%, 2%, 0.6%, 0.2%, and 0.07%. The mixtures are incubated for 30 minutes at 4° C. After 30 minutes, the plates are centrifuged for 4 minutes at 400×g. The plates are decanted and washed with HBSS. Rabbit complement (150 µl of a 1:15 dilution) is added to each well and incubated for 30 minutes at 37° C. PBMC are labeled with a fluorescein diacetate (FDA) stock solution, prepared fresh daily in HBSS (1 µg/ml) from a 1 mg/ml stock solution in acetone and with propidium iodide (PI), prepared at 50 µg/ml in phosphate buffered saline (PBS). After incubation in complement, the samples are transferred by pipette to tubes containing 250 µl of HBSS and 10 µl of FDA/PI for analysis using an Accuri C6 flow cytometer.

The percentage of dead cells (PI+/FDA−), damaged cells (PI+/FDA+) and live cells is determined. Double negative events (PI−/FDA−) are excluded from calculations. The percentage of cytotoxicity in cells not exposed to serum is considered spontaneous killing. Values for cytotoxicity are corrected for spontaneous killing.

Example 52

Platelet Uptake Analysis I

Platelets are labeled with carboxyfluorecein diacetate succinimidyl ester (CFSE), a fluorescent green cytoplasmic marker. A normothermic pig liver perfusion system is used. Pig livers from knockout pigs of interest or wild-type pigs are perfused for two hours prior to the addition of platelets. Approximately 300 billion platelets (unlabeled 70%, labeled 30%) are added to the perfusion system. Biopsies are taken from the pig livers at various predetermined time points. Biopsies are examined by confocal microscopy. Biopsies are treated with a stain specific for Wieble-Palade bodies. Wieble-Palade bodies occur in platelets and endothelial cells. Fluorescent ELISA based assays are performed. Platelets are human or baboon. Alternatively biopsies are labeled with endothelial markers and a lysosomal marker, prior to confocal microscopy.

Example 53

Platelet Uptake Analysis II

Platelets are labeled with carboxyfluorecein diacetate succinimidyl ester (CFSE), a fluorescent green cytoplasmic marker. A normothermic pig liver perfusion system is used.

Pig livers from knockout pigs of interest or wild-type pigs are perfused for two hours prior to the addition of platelets. Biopsies are analyzed by transmission electron microscopy (TEM).

Example 54

In Vitro Platelet Uptake

Primary liver sinusoidal endothelial cells (LSECs) are isolated from the sinusoid of a pig liver or livers of interest. Primary wild-type porcine LSECs loos phagocytic ability after 5 days in culture; these experiments are performed with day 3 and 4 primary LSECs. Human or baboon platelets are labeled with CFSE as described elsewhere herein. Isolated LSECs and labeled platelets are incubated together. Samples are analyzed by confocal microscopy.

All publications, patents, and patent applications mentioned in the specification are indicative of the level of those skilled in the art to which this invention pertains. All publications, patents, and patent applications are herein incorporated by reference to the same extent as if each individual publication or patent application was specifically and individually incorporated by reference.

The invention is not limited to the embodiments set forth herein for illustration but includes everything that is within the scope of the claims. Having described the invention with reference to the exemplary embodiments, it is to be understood that it is not intended that any limitations or elements describing the exemplary embodiment set forth herein are to be incorporated into the meanings of the patent claims unless such limitations or elements are explicitly listed in the claims. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not be explicitly discussed herein.

Although the foregoing invention has been described in some detail by way of illustration and example for purposes of clarity of understanding, it will be obvious that certain changes and modifications may be practiced within the scope of the appended claims.

We claim:

1. A transgenic pig whose genome comprises a homozygous disruption of the ASGR1 gene wherein no detectable level of ASGR1 protein is present, and wherein the liver from said pig exhibits reduced human platelet uptake as compared to the liver from a wild-type pig when the livers are exposed to human platelets.

2. A porcine organ, tissue or cell isolated from said transgenic pig of claim 1.

3. The porcine organ, tissue or cell of claim 2, wherein said porcine organ, tissue or cell is selected from the group consisting of skin, heart, liver, kidneys, lung, pancreas, thyroid, small bowel and components thereof.

4. The transgenic pig of claim 1 wherein when tissue from said pig is transplanted into a human, thrombocytopenia is decreased as compared to when tissue from a wild-type pig is transplanted into a human.

5. The transgenic pig of claim 1, wherein the disruption of said ASGR1 gene is a homozygous deletion of 26 base pairs.

6. The knockout pig of claim 5 wherein said homozygous deletion disrupts said ASGR1 gene at a region of the wild-type gene having the nucleotide sequence set forth as AGGTCTAGCCAGCCTTAGCATGACAA (SEQ ID NO: 15).

* * * * *